US012747208B2

(12) United States Patent
Iliopoulos et al.

(10) Patent No.: US 12,747,208 B2
(45) Date of Patent: Sep. 29, 2026

(54) PHARMACEUTICAL COMPOUNDS AND METHODS OF MAKING AND USING THE SAME

(71) Applicant: Athos Therapeutics, Inc., Torrance, CA (US)

(72) Inventors: Dimitrios Iliopoulos, Los Angeles, CA (US); David G. Ho, Monterey Park, CA (US); Iordanis Karagiannidis, North Hollywood, CA (US); Phithi Nguyen, Anaheim, CA (US); Dimitra Chalkia, Fullerton, CA (US)

(73) Assignee: Athos Therapeutics, Inc., Torrance, CA (US)

( * ) Notice: Subject to any disclaimer, the term of this patent is extended or adjusted under 35 U.S.C. 154(b) by 327 days.

(21) Appl. No.: 18/262,676

(22) PCT Filed: Jan. 24, 2022

(86) PCT No.: PCT/US2022/070319
§ 371 (c)(1),
(2) Date: Jul. 24, 2023

(87) PCT Pub. No.: WO2022/159980
PCT Pub. Date: Jul. 28, 2022

(65) Prior Publication Data

US 2025/0042850 A1 Feb. 6, 2025

Related U.S. Application Data

(60) Provisional application No. 63/141,326, filed on Jan. 25, 2021.

(51) Int. Cl.

| | |
|---|---|
| ***C07D 207/333*** | (2006.01) |
| ***A61K 9/00*** | (2006.01) |
| ***A61K 9/02*** | (2006.01) |
| ***A61K 9/20*** | (2006.01) |
| ***A61K 9/48*** | (2006.01) |
| ***A61K 31/401*** | (2006.01) |
| ***A61K 31/4025*** | (2006.01) |
| ***A61K 31/407*** | (2006.01) |
| ***A61K 31/4439*** | (2006.01) |
| ***A61K 31/695*** | (2006.01) |
| ***A61K 47/02*** | (2006.01) |
| ***A61K 47/12*** | (2006.01) |
| ***A61K 47/14*** | (2017.01) |
| ***A61K 47/26*** | (2006.01) |
| ***C07D 401/06*** | (2006.01) |
| ***C07D 403/06*** | (2006.01) |
| ***C07D 491/107*** | (2006.01) |
| ***C07F 7/18*** | (2006.01) |

(52) U.S. Cl.
CPC ........ *C07D 207/333* (2013.01); *A61K 9/0019* (2013.01); *A61K 9/0053* (2013.01); *A61K 9/02* (2013.01); *A61K 9/2013* (2013.01); *A61K 9/2018* (2013.01); *A61K 9/2054* (2013.01); *A61K 9/2059* (2013.01); *A61K 9/4825* (2013.01); *A61K 9/4858* (2013.01); *A61K 31/401* (2013.01); *A61K 31/4025* (2013.01); *A61K 31/407* (2013.01); *A61K 31/4439* (2013.01); *A61K 31/695* (2013.01); *A61K 47/02* (2013.01); *A61K 47/12* (2013.01); *A61K 47/14* (2013.01); *A61K 47/26* (2013.01); *C07D 401/06* (2013.01); *C07D 403/06* (2013.01); *C07D 491/107* (2013.01); *C07F 7/1804* (2013.01); *C07F 7/1892* (2013.01)

(58) Field of Classification Search
CPC ......................... C07D 207/333; C07D 401/06; C07D 403/06; C07D 491/107; A61K 9/0019; A61K 9/0053; A61K 9/02; A61K 9/2013; A61K 9/2018; A61K 9/2054; A61K 9/2059; A61K 9/4825; A61K 9/4858; A61K 31/401; A61K 31/4025; A61K 31/407; A61K 31/4439; A61K 31/695; A61K 47/02; A61K 47/12; A61K 47/14; A61K 47/26; C07F 7/1804; C07F 7/1892
See application file for complete search history.

(56) References Cited

U.S. PATENT DOCUMENTS

| | | | |
|---|---|---|---|
| 5,332,736 | A | 7/1994 | Carmosin et al. |
| 6,057,456 | A | 5/2000 | Hartwig et al. |

FOREIGN PATENT DOCUMENTS

| | | |
|---|---|---|
| EP | 0 714 895 | 6/1996 |
| WO | WO 03/057219 | 7/2003 |
| WO | WO 04/014368 | 2/2004 |

(Continued)

OTHER PUBLICATIONS

CAS Registry No. 1094749-76-4 (which entered STN on Jan. 21, 2009) (Year: 2009).*

(Continued)

*Primary Examiner* — Kamal A Saeed
*Assistant Examiner* — Quincy Mckoy
(74) *Attorney, Agent, or Firm* — Knobbe, Martens, Olson & Bear, LLP

(57) ABSTRACT

Disclosed herein are compounds (e.g., pyrrole compounds, carboxy pyrroles, etc.), including pharmaceutical compositions that include one or more of such compounds (e.g., carboxy pyrroles). Also disclosed are methods of making carboxy pyrrole compounds. Also disclosed herein are methods of treating diseases and/or conditions (e.g., inflammation and/or cancer) with the carboxy pyrrole compounds disclosed herein.

20 Claims, 2 Drawing Sheets

(56) References Cited

FOREIGN PATENT DOCUMENTS

| | | | |
|---|---|---|---|
| WO | WO 15/002994 | 1/2015 | |
| WO | WO-2016042341 A1 * | 3/2016 | ........... C07D 405/14 |
| WO | WO 20/176863 | 9/2020 | |

OTHER PUBLICATIONS

CAS Registry No. 1094648-97-1 (which entered STN on Jan. 21, 2009) (Year: 2009).*
Papireddy, Kancharla, et al. "Antimalarial activity of natural and synthetic prodiginines." Journal of medicinal chemistry 54.15 (2011): 5296-5306. (Year: 2011).*
CAS Registry No. 936832-06-3 (which entered STN on Jun. 8, 2007) (Year: 2007).*
Halder, Nyancy, et al. "meso-Aryl substituted stable unorthodox 5, 10-porphodimethenes with α, β and β, β-N-methyl pyrrole connectivities: synthesis and spectroscopic, solid state and theoretical characterization." Organic & Biomolecular Chemistry 17.25 (2019): 6131-6135. (Year: 2019).*
Kumar, Togiti Uday, et al. "Application of Polyphosphoric Acid-Mediated Acyl Migration for Regiospecific Synthesis of Diverse 2-Acylpyrroles from Chalcones." Journal of Heterocyclic Chemistry 56.4 (2019): 1283-1290. (Year: 2019).*
Carson et al., 1997, Aroyl(aminoacyl)pyrroles, a new class of anticonvulsant agents, J. Med. Chem., 40:1578-1584.
Myers et al., 2016, High-throughput screening and hit validation of extracellular-related kinase 5 (ERK5) inhibitors, ACS Comb. Sci., 18:444-455.
Xing et al., 2012, Palladium-catalyzed mono- and double-carbonylation of indoles with amines controllably leading to amides and α-ketoamides, Chem. Commun., 48:11023-11025 and supplementary information.
International Search Report and Written Opinion dated Mar. 17, 2022 in application No. PCT/US2022/070319.

* cited by examiner

PHARMACEUTICAL COMPOUNDS AND METHODS OF MAKING AND USING THE SAME

CROSS REFERENCE TO RELATED APPLICATIONS

The present application is a U.S. National Phase of international Application No. PCT/US2022/070319, filed on Jan. 24, 2022, and published on Jul. 28, 2022, as WO 2022/159980, which claims the benefit of priority to U.S. Provisional Patent Application No. 63/141,326, filed Jan. 25, 2021. The disclosures of the foregoing applications are hereby incorporated by reference in their entireties. Any and all applications for which a foreign or domestic priority claim is identified in the Application Data Sheet as filed with the present application are hereby incorporated by reference under 37 CFR 1.57.

FIELD

Disclosed herein are compounds (e.g., pyrrole compounds, carboxy pyrroles, etc.), including pharmaceutical compositions that include one or more of such compounds (e.g., carboxy pyrroles). Also disclosed are methods of making carboxy pyrrole compounds.

BACKGROUND

The enzyme vascular non-inflammatory molecule-1 (vanin 1) is prominent in many organs, such as the liver, intestine, and kidney. Its major function is the metabolization of pantetheine into cysteamine and pantothenic acid. Vanin 1 plays a complex role in disease, having a protective effect or acting a sensitizer, depending on with which organ it is associated.

SUMMARY

Several embodiments disclosed herein pertain to pyrrole compounds (e.g., carboxy pyrrole compounds), their use as inhibitors of the enzymatic activity of vanin 1. Some embodiments pertain to methods of manufacturing pyrrole compounds, and methods of using pyrrole compounds as therapeutics for treating inflammatory disease states. In several embodiments, the pyrrole compound comprises a substituted pyrrole attached to a carboxy group (e.g., a carboxy pyrrole). Several embodiments comprise, consist of, or consist essentially of a carboxy pyrrole compound of Formula (I) (or any other structure disclosed herein), their pharmaceutically acceptable salts, enantiomers, methods of manufacture, and/or their methods of use in treating disease states. In several embodiments, by using one or more compounds of Formula (I) (or any other structure disclosed herein) to inhibit the activity of vanin 1 in a subject, a disease state can be treated. In several embodiments, the disease state is associated with inflammation. In several embodiments, the disease state is associated with an autoimmune disorder. In several embodiments, the disease state is a cancer mediated at least in part through vanin 1.

Several embodiments pertain to vanin 1 inhibitors. In several embodiments, a vanin 1 inhibitor comprises a compound, or a pharmaceutically acceptable salt thereof, having a structure represented by Formula I:

(I)

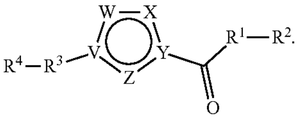

In several embodiments, V, W, X, Y, and Z are each independently selected from the group consisting of C, C($R^5$), N, and $NR^6$ where at least one instance of V, W, X, Y, and Z is N or $NR^6$ with the remaining variables being C or C($R^5$). In several embodiments, $R^1$ is either not present or, where present, is selected from the group consisting of optionally substituted $C_{1-3}$ alkylene, optionally substituted 3-12 membered heterocyclyl, 5-10 optionally substituted heteroaryl, and —$NR^7$—. In several embodiments, $R^2$ is either not present or, where present, is selected from the group consisting of —H, —OH, optionally substituted alkyl, optionally substituted N-amido, optionally substituted $C_{6-10}$ aryl, 5-10 optionally substituted heteroaryl, optionally substituted $C_{6-10}$ aryl, optionally substituted 3-10 membered carbocyclyl, and optionally substituted 3-12 membered heterocyclyl. In several embodiments, $R^3$ is either not present or, where present, is selected from the group consisting of optionally substituted $C_{1-3}$ alkylene, —$NR^7$—, —C(═O)—, —C(═O) NH—, and —C(═O) $NR^7$—. In several embodiments, $R^4$ is either not present or, where present, is selected from the group consisting of optionally substituted $C_{6-10}$ aryl, optionally substituted 5-10 membered heteroaryl, optionally substituted 3-10 membered heterocyclyl, and optionally substituted $C_{1-6}$ alkyl. In several embodiments, each instance of $R^5$, $R^6$ and $R^7$, where present, is independently selected from the group consisting of —H, halogen, hydroxy, $C_{1-6}$ alkyl, $C_1$-$C_6$ alkoxy, $C_{1-6}$ haloalkyl, optionally substituted $C_{6-10}$ aryl, optionally substituted $C_{6-10}$ benzyl, and optionally substituted $C_{3-7}$ carbocyclyl.

Some embodiments pertain to a compound of Formula (I) or a pharmaceutically acceptable salt thereof:

(I)

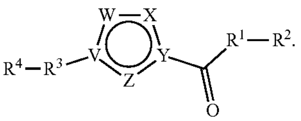

In several embodiments, V, W, X, Y, and Z are each independently selected from the group consisting of C, C($R^5$), N, and $NR^6$. In several embodiments, at least one instance of V, W, X, Y, and Z is N or $NR^6$ with the remaining variables being C or C($R^5$). In several embodiments, $R^1$ is selected from the group consisting of optionally substituted $C_{1-3}$ alkylene, 3-10 membered heterocyclyl, —$NR^7$—, and a single bond. In several embodiments, $R^1$ is not present. In several embodiments, $R^2$ is selected from the group consisting of —H, optionally substituted $C_{1-6}$ alkyl, optionally substituted $C_{6-10}$ aryl, 5-10 optionally substituted heteroaryl, optionally substituted 5-10 membered heteroaryl, optionally substituted 3-10 membered carbocyclyl, and optionally substituted 3-10 membered heterocyclyl. In several embodiments, $R^3$ is selected from the group consisting of optionally substituted $C_{1-3}$ alkylene, —$NR^7$—, —C(═O)—, —C(═O) NH—, —C(═O) $NR^7$—, and a single bond. In several embodiments, $R^4$ is selected from the group consisting of —H, optionally substituted $C_{6-10}$ aryl, optionally substituted 5-10 membered heteroaryl, optionally substituted 3-10 membered heterocyclyl, and optionally substituted $C_1$-6 alkyl. In several embodiments, each instance of $R^5$, $R^6$ and $R^7$, where present, is independently selected from the group consisting of —H, halogen (e.g., —F, —Cl, etc.), hydroxy, $C_{1-6}$ alkyl, $C_1$-$C_6$ alkoxy, $C_{1-6}$ haloalkyl, optionally substituted $C_{6-10}$ aryl, optionally substituted $C_{6-10}$ benzyl, and optionally substituted $C_{3-7}$ carbocyclyl.

Several embodiments pertain to a compound of Formula (I), or a pharmaceutically acceptable salt thereof, further represented by one or more of Formulae (Ia), (Ib), (Ic), (Id), or (Ie):

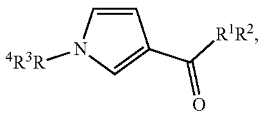
(Ia)

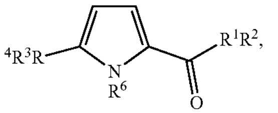
(Ib)

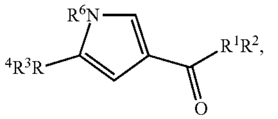
(Ic)

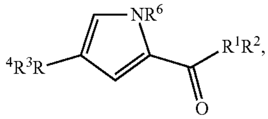
and
(Id)

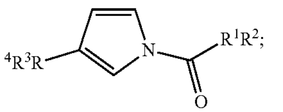
(Ie)

where the variables are as disclosed elsewhere herein (e.g., the variables may be as defined for Formula (I) or any other formula comprising the same variable). In several embodiments, $R^1$ is selected from the group consisting of —NH—, —$CH_2$—, —$CHR^8$, —$C(R^8)_2$, and a single bond. In several embodiments, each instance of $R^8$, where present, is independently selected from the group consisting of —H, halogen, hydroxy, optionally substituted $C_{1-6}$ alkyl, optionally substituted $C_1$-$C_6$ alkoxy, optionally substituted $C_{1-6}$ haloalkyl, optionally substituted $C_{6-10}$ aryl, optionally substituted $C_{6-10}$ aralkyl, optionally substituted $C_{6-10}$ haloaralkyl, and optionally substituted $C_{3-7}$ carbocyclyl. In several embodiments, $R^1$ is selected from the group consisting of:

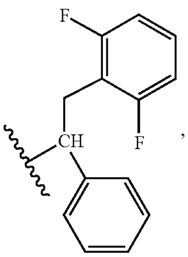
,
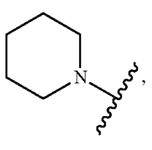

-continued

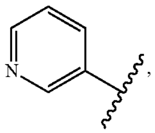
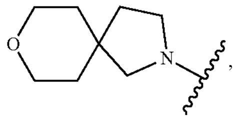
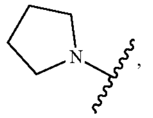
and
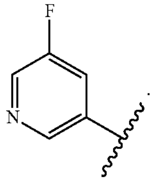

Any one of the directly preceding structures may be further optionally substituted by replacing one or more-H atoms of any carbon or nitrogen atom present within the structure. In several embodiments, $R^2$ is selected from the group consisting of optionally substituted $C_{6-10}$ aryl, optionally substituted 5-10 membered heteroaryl, optionally substituted 3-10 membered heterocyclyl, optionally substituted N-amido, and optionally substituted C-amido. In several embodiments, $R^2$ is selected from the group consisting of:

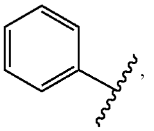
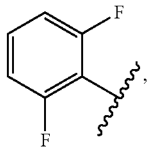
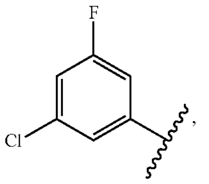
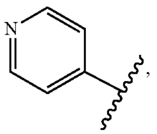
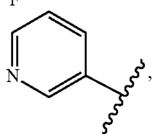
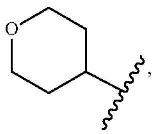
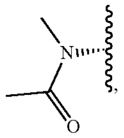
and
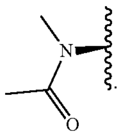

Any one of the directly preceding structures may be further optionally substituted by replacing one or more-H atoms of any carbon or nitrogen atom present within the structure. In several embodiments, N-amido is represented by:

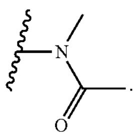 [SMILES: *N(C)C(C)=O]

In several embodiments, $R^3$ is —$C(R^6)_2$—, —C(O)—, or —C(O) $NR^6$—. In several embodiments, each instance of $R^6$, where present, is independently selected from the group consisting of —H, halogen, hydroxy, $C_{1-6}$ alkyl, $C_1$-$C_6$ alkoxy, $C_{1-6}$ haloalkyl, and $C_{6-10}$ aryl. In several embodiments, $R^3$ is selected from the group consisting of —$CH_2$— and —C(═O)—. In several embodiments, $R^3$ is selected from the group consisting of —$CH_2$—, —C(═O)—, and —C(═O) NH—. In several embodiments, $R^4$ is selected from the group consisting of optionally substituted $C_{6-10}$ aryl, optionally substituted 5-10 membered heteroaryl, optionally substituted 3-10 membered heterocyclyl, and optionally substituted $C_{1-6}$ alkyl. In several embodiments, $R^4$ is selected from the group consisting of:

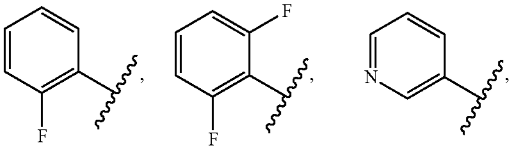

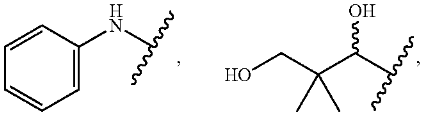

and

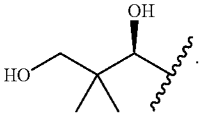

Any one of the directly preceding structures may be further optionally substituted by replacing one or more-H atoms of any carbon or nitrogen atom present within the structure.

In several embodiments, when any one or more of $R^1$, $R^2$, $R^3$, or $R^4$ is optionally substituted, one or more optional substitutions of $R^1$, $R^2$, $R^3$, or $R^4$ are independently selected from the group consisting of halogen (e.g., —F, —Cl, etc.), hydroxy, $C_{1-6}$ alkyl (e.g., —Me), $C_{1-6}$ alkoxy (e.g., —OMe, —OEt, etc.), aryl (optionally substituted with halogen), and heteroaryl. In several embodiments, when $R^2$ is optionally substituted, one or more optional substitutions of $R^2$ are independently selected from the group consisting of halogen, hydroxy, $C_{1-6}$ alkyl, $C_{1-6}$ alkoxy, aryl, heteroaryl, N-amido, and C-amido. In several embodiments, N-amido is:

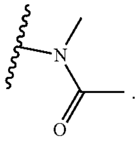 [SMILES: *N(C)C(C)=O]

In several embodiments, like variables for different formulae ($R^1$ for Formula (I) and $R^1$ for Formula (Ia); $R^2$ for Formula (I) and $R^2$ for Formula (Ib), etc.) maybe used to define that like variable for any other formula. Thus, any variable for Formula (I) may be defined using the same variables for any one or more of Formula (Ia), (Ib), (Ic), (Id), (Ie), (Ia1), (Ib1), (Ia2), (Ib2), (Ia3), (Ib3), (Ia4), (Ib4), (Ia5), and (Ib5) (or vice versa).

Several embodiments pertain to a compound of Formula (I), or a pharmaceutically acceptable salt thereof, further represented by Formulae (Ia1) or (Ib1):

(Ia1)

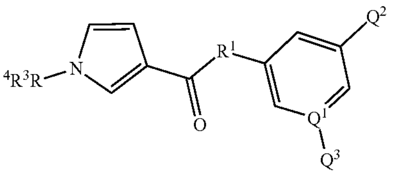

-continued (Ib1)

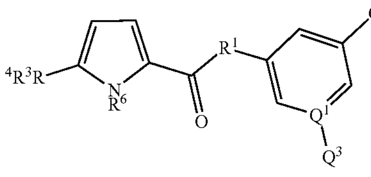

where the variables are as disclosed elsewhere herein (e.g., as for any one of Formulae (I), (Ia), (Ib), (Ic), (Id), (Ie), etc.). In several embodiments, $R^1$ is —$CH_2$— or —NH—. In several embodiments, $Q^1$ is C or N. In several embodiments, each instance of $Q^2$ and $Q^3$, when present, is independently selected from the group consisting of —H, halogen, hydroxy, $C_{1-6}$ alkyl, $C_1$-$C_6$ alkoxy, $C_{1-6}$ haloalkyl, and nitro; with the proviso that when $Q^1$ is N, then $Q^3$ is absent. In several embodiments, $R^3$ is selected from the group consisting of —$CH_2$—, —C(=O)—, and —C(=O) NH—. In several embodiments, $R^4$ is optionally substituted $C_{6-10}$ aryl or optionally substituted 5-10 membered heteroaryl. In several embodiments, $R^6$ is selected from the group consisting of —H, $C_{1-6}$ alkyl, $C_{1-6}$ haloalkyl, and $C_{6-10}$ aryl. In several embodiments, $R^6$ is $C_{1-6}$ alkyl. In several embodiments, $R^6$ is methyl.

Several embodiments pertain to a compound of Formula (I), or a pharmaceutically acceptable salt thereof, further represented by Formulae (Ia2) or (Ib2):

(Ia2)

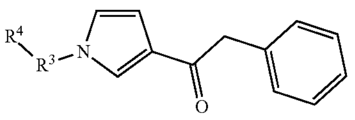

(Ib2)

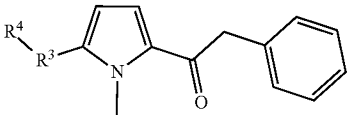

where the variables are as disclosed elsewhere herein (e.g., as for any one of Formulae (I), (Ia), (Ib), (Ic), (Id), (Ie), (Ia1), (Ib1), etc.). In several embodiments, $R^4$ is selected from the group consisting of:

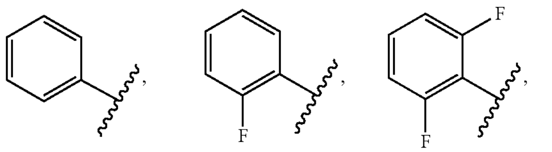

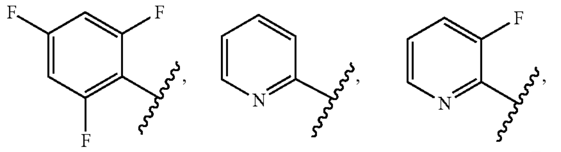

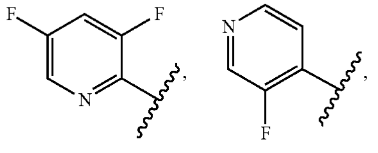

and

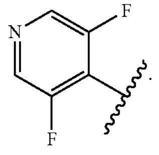

Any one of the directly preceding structures may be further optionally substituted by replacing one or more-H atoms of any carbon or nitrogen atom present within the structure.

Several embodiments pertain to a compound of Formula (I), or a pharmaceutically acceptable salt thereof, further represented by Formulae (Ia3), (Ia4), (Ib3), or (Ib4):

(Ia3)

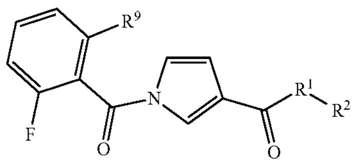

(Ib3)

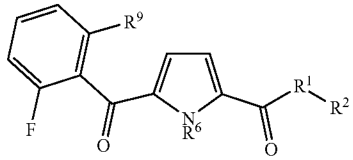

(Ia4)

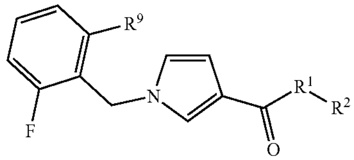

(Ib4)

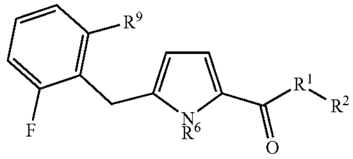

where the variables are as disclosed elsewhere herein (e.g., as for any one of Formulae (I), (Ia), (Ib), (Ic), (Id), (Ie), (Ia1), (Ib1), etc.). In several embodiments, $R^1$ is selected from the group consisting of —$CH_2$—, —$CHCH_2$-(optionally substituted with phenyl by replacing an H-atom for phenyl), —NH—, and a single bond. In several embodiments, $R^2$ is selected from the group consisting of optionally substituted $C_{6-10}$ aryl, optionally substituted 6 membered heteroaryl, and optionally substituted 6-10 membered heterocyclyl (including a 10 member heterocyclyl). In several embodiments, $R^6$ is selected from the group consisting of —H, $C_{1-6}$ alkyl, $C_{1-6}$ haloalkyl, and $C_{6-10}$ aryl. In several embodiments, $R^9$ is selected from the group consisting of —H, halogen, and nitro. In several embodiments, $R^1$ is —$CHCH_2R^{10}$ where $R^{10}$ is selected from the group consisting of:

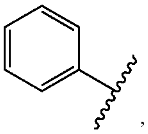
,
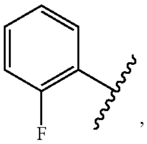
,
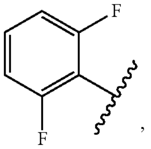
,
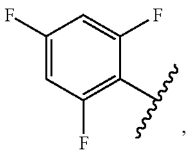
,
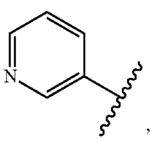
,
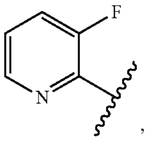
,

-continued

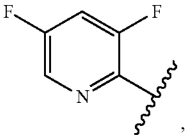
,
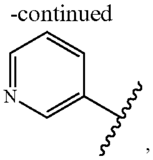
,
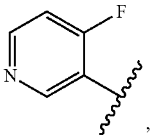
,
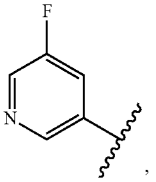
,
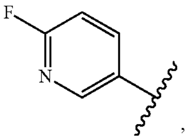
,
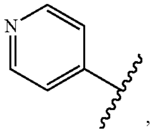
,
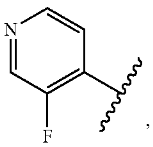
, and
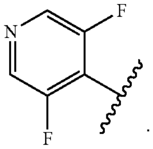
.

Any one of the directly preceding structures may be further optionally substituted by replacing one or more-H atoms of any carbon or nitrogen atom present within the structure. In several embodiments, $R^1$ is —$CH_2$—. In several embodiments, $R^2$ is selected from the group consisting of:

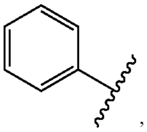
,
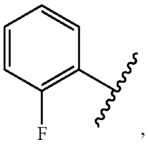
,
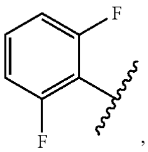
,
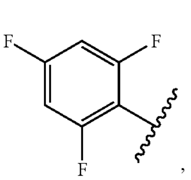
,
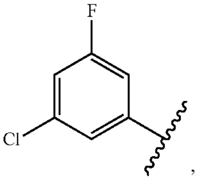
,
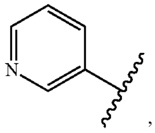
,
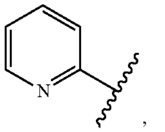
,
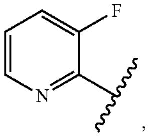
,
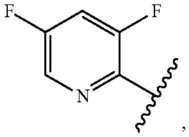
,
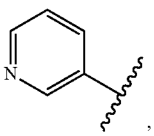
,
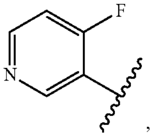
,
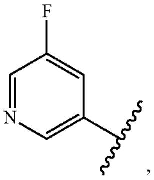
,
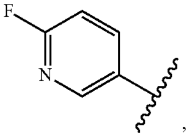
,
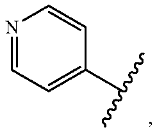
,
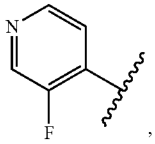
, and
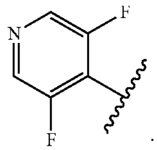
.

Any one of the directly preceding structures may be further optionally substituted by replacing one or more-H atoms of any carbon or nitrogen atom present within the structure. In several embodiments, $R^1$ is —NH— or a single bond. In several embodiments, $R^2$ is selected from the group consisting of:

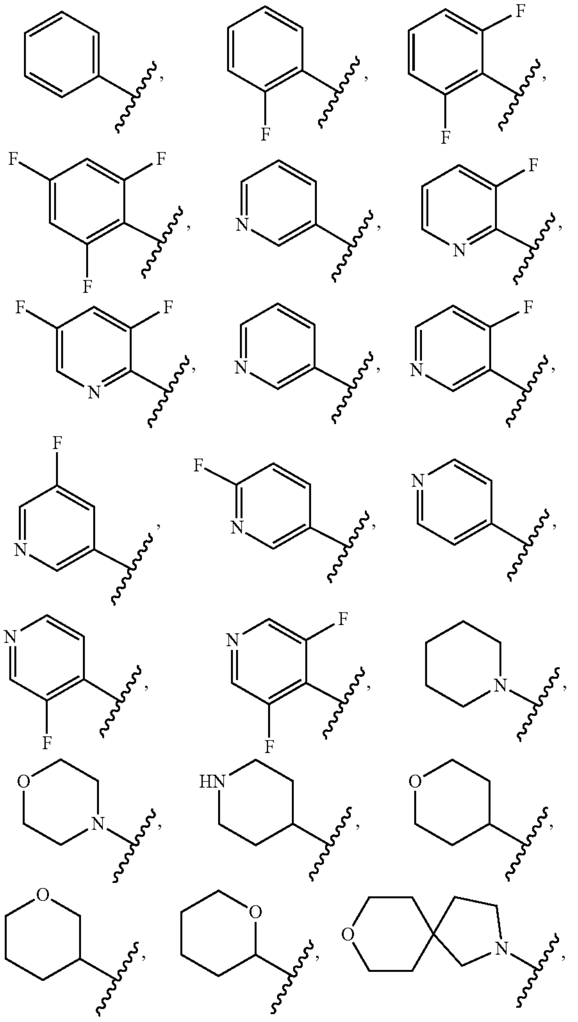

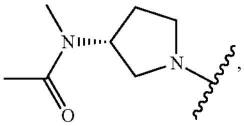

and

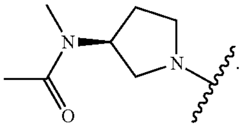

Any one of the directly preceding structures may be further optionally substituted by replacing one or more-H atoms of any carbon or nitrogen atom present within the structure. In several embodiments, $R^6$ is $C_{1-6}$ alkyl. In several embodiments, $R^6$ is methyl. In several embodiments, $R^9$ is halogen. In several embodiments, $R^9$ is F.

Several embodiments pertain to a compound of Formula (I), or a pharmaceutically acceptable salt thereof, further represented by Formulae (Ia5) or (Ib5):

(Ia5)

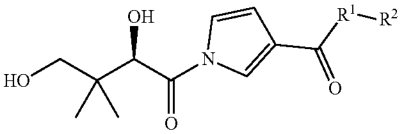

-continued (Ib5)

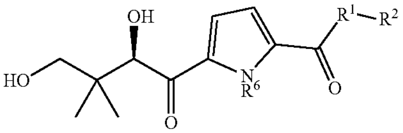

where the variables are as disclosed elsewhere herein. In several embodiments, $R^1$ is —$CH_2$— or single bond. In several embodiments, $R^2$ is selected from the group consisting of optionally substituted $C_{6-10}$ aryl, optionally substituted 6 membered heteroaryl, and optionally substituted 6-10 membered heterocyclyl. In several embodiments, $R^6$ is selected from the group consisting of —H, $C_{1-6}$ alkyl, $C_{1-6}$ haloalkyl, and $C_{6-10}$ aryl. In several embodiments, Re is $C_{1-6}$ alkyl. In several embodiments, $R^6$ is methyl. In several embodiments, $R^2$ is selected from the group consisting of:

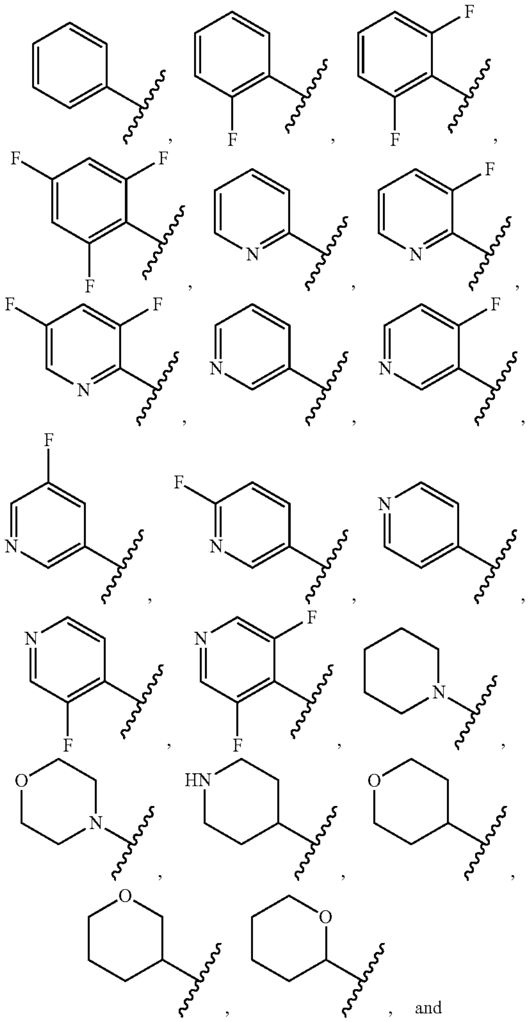

and

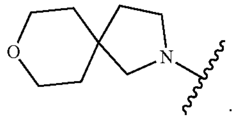

Any one of the directly preceding structures may be further optionally substituted by replacing one or more-H atoms of any carbon or nitrogen atom present within the structure.

In several embodiments, the structure of Formula (I) is further represented by a formula selected from any one of Formulae Compound 1, Compound 2, Compound 3, or Compound 80:

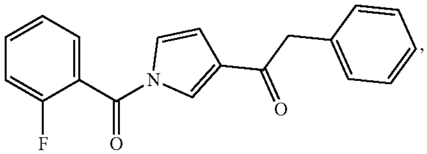,

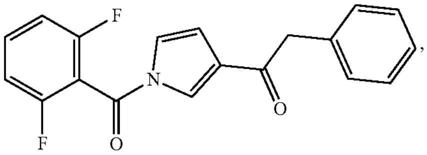,

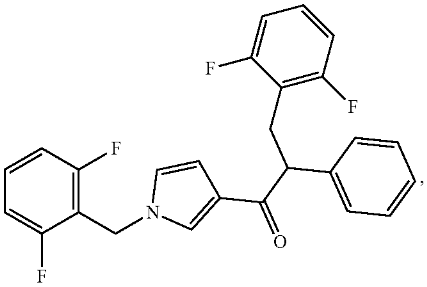, and

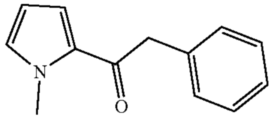

In several embodiments, the compound with the structure of Formula (I) does not comprise one or more groups selected from any one of Formulae (IIa), (IIb), or (IIc):

(IIa)

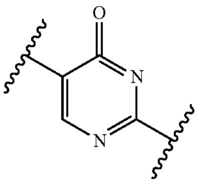

(IIb)

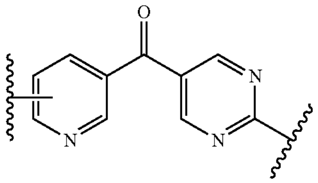

(IIc)

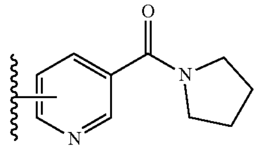.

Several embodiments pertain to a compound of Formula (I), or a pharmaceutically acceptable salt thereof, further represented by one of Compounds 1 to 79. Several embodiments pertain to a compound of Formula (I), or a pharmaceutically acceptable salt thereof, further represented by one of the following structures:

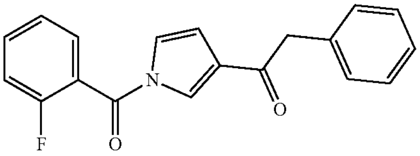

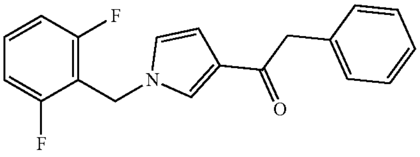

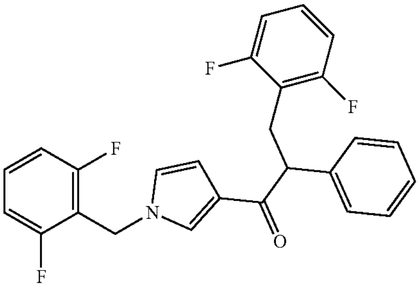

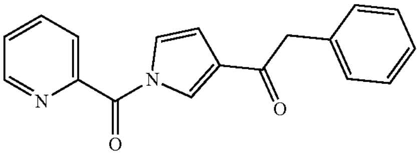

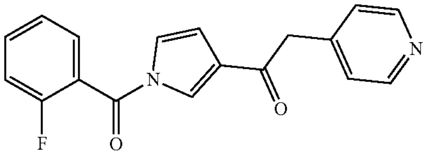

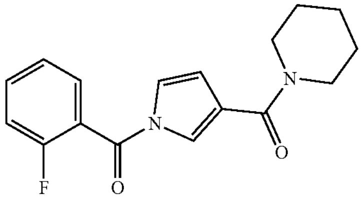

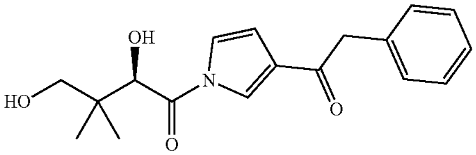

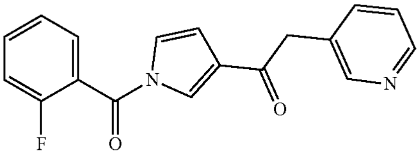

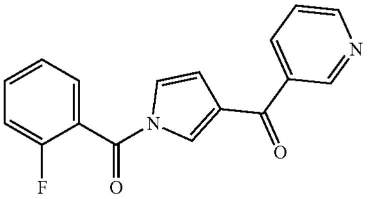

-continued
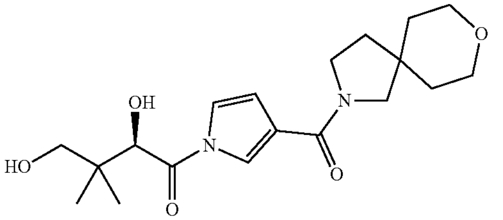
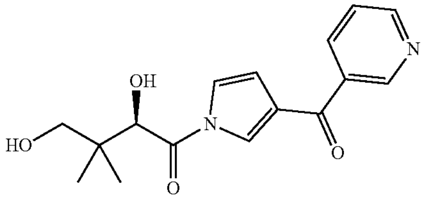
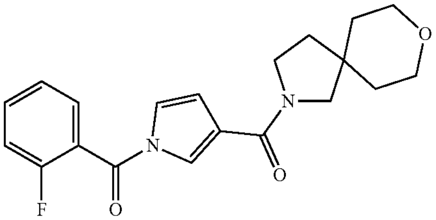
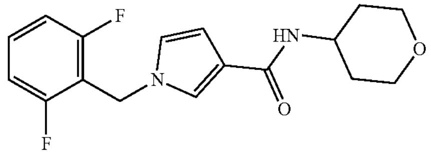
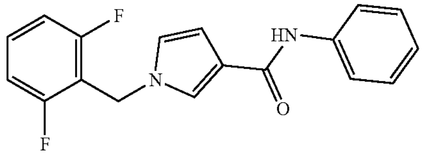
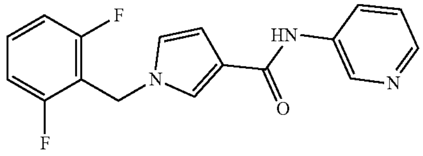
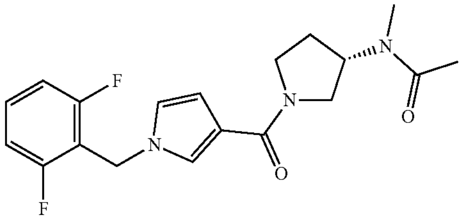
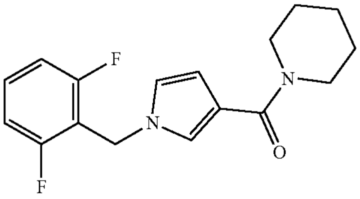
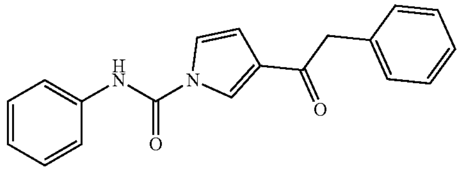
-continued
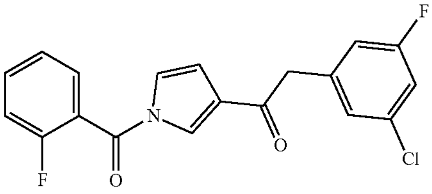
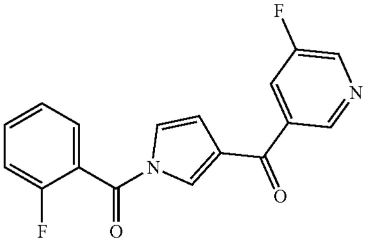
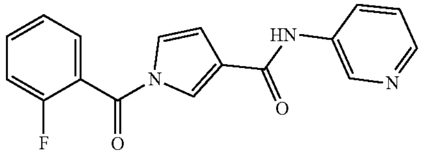
Several embodiments pertain to a compound of Formula (I), or a pharmaceutically acceptable salt thereof, further represented by one of the following structures:
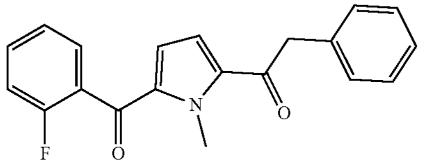
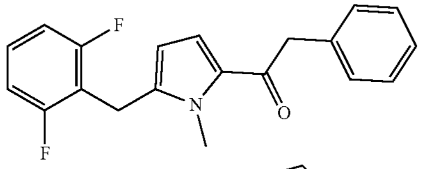
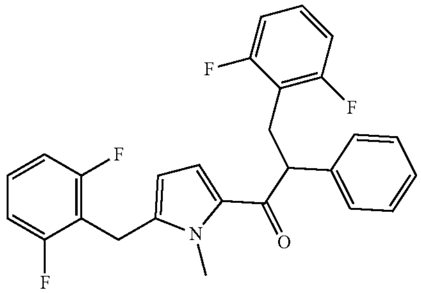
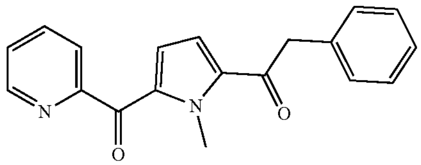
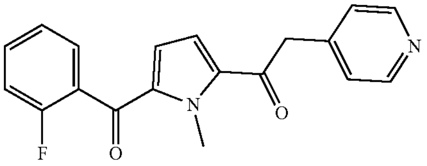

-continued

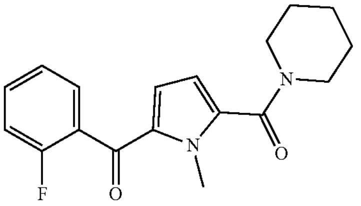

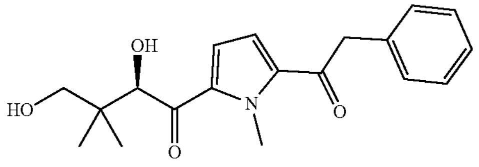

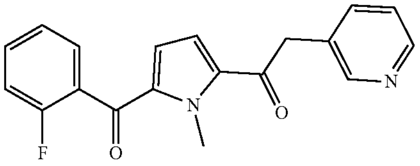

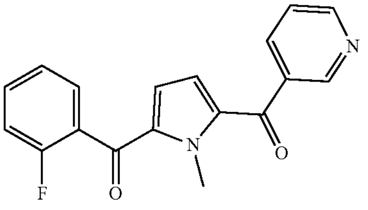

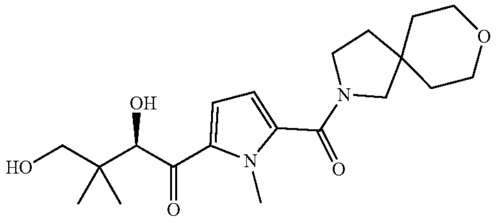

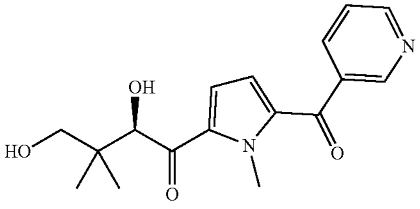

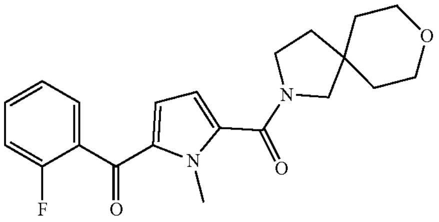

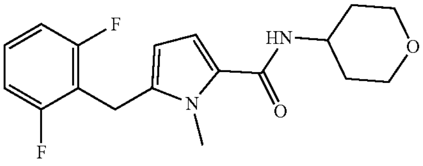

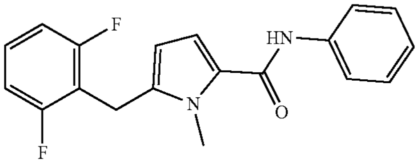

-continued

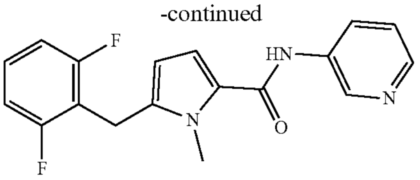

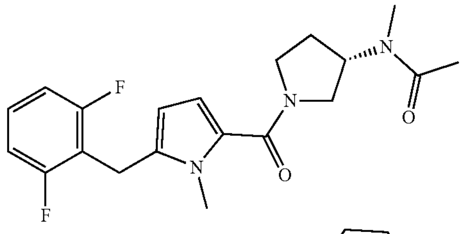

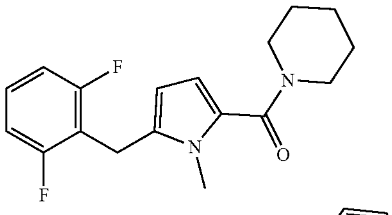

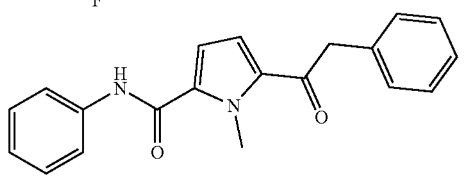

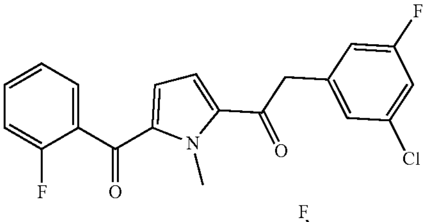

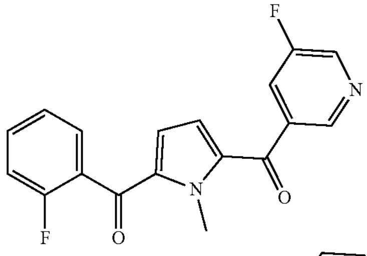

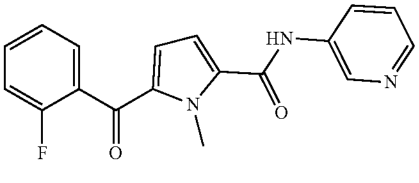
.

Several embodiments pertain to a method of inhibiting the enzymatic activity of the enzyme vascular non-inflammatory molecule. In several embodiments, the method pertains to the inhibition of the enzymatic activity of the enzyme vascular non-inflammatory molecule-1 (vanin 1). In several embodiments, the method comprises administering a compound as disclosed herein (e.g., a carboxy pyrrole) to a patient in need of treatment thereby treating the patient. In several embodiments, the method comprises administering an effective amount of a compound as disclosed herein to a patient in need of treatment. In several embodiments, in response to a determination of the presence of inflammatory and autoimmune disease in a sample from a subject, the subject is administered an effective amount the compound, thereby treating the inflammatory and autoimmune disease in the subject. In several embodiments, the subject is suffering from an autoimmune or inflammatory disorder. In several embodiments, the subject is suffering from a form of cancer.

DETAILED DESCRIPTION

Figure 1A:
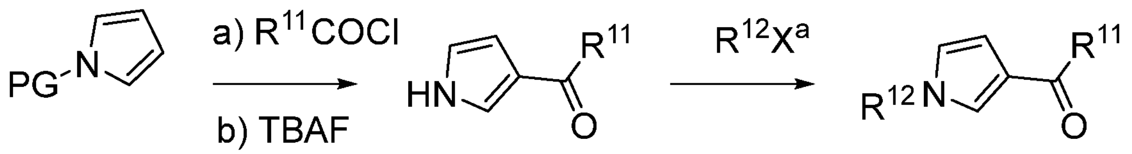
FIG. 1A provides a reaction pathway for the preparation of several embodiments of compounds of Formula (I).

Several embodiments disclosed herein provide compounds useful in inhibiting the activity of vanin 1 in a subject. Several embodiments also provide methods of treating diseases utilizing these compounds or pharmaceutical compositions comprising these compounds. In several embodiments, the compounds are carboxy pyrrole compounds. In several embodiments, multiple functionalities are bound to a core pyrrole structure including a carboxy (e.g., a carbonyl that bonded to the pyrrole ring). In several embodiments, the disclosed carboxy pyrrole can be used in methods of treating inflammatory and autoimmune diseases. The following description provides context and examples, but should not be interpreted to limit the scope of the inventions covered by the claims that follow in this specification or in any other application that claims priority to this specification. No single component or collection of components is essential or indispensable. For example, in some embodiments where a structure is disclosed, one or more variables of that structure may be omitted (such as $R^1$, $R^2$, $R^3$, $R^4$, Y or Y and Q). Any feature, structure, component, material, step, or method that is described and/or illustrated in any embodiment in this specification can be used with or instead of any feature, structure, component, material, step, or method that is described and/or illustrated in any other embodiment in this specification.

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. Conventional procedures for the selection and preparation of suitable prodrug derivatives are described, for example, in Design of Prodrugs, (ed. H. Bundgaard, Elsevier, 1985), which is hereby incorporated herein by reference in its entirety.

The term "pro-drug ester" refers to derivatives of the compounds disclosed herein formed by the addition of any of several ester-forming groups that are hydrolyzed under physiological conditions. Examples of pro-drug ester groups include pivoyloxymethyl, acetoxymethyl, phthalidyl, indanyl and methoxymethyl, as well as other such groups known in the art, including a (5-R-2-oxo-1,3-dioxolen-4-yl)methyl group. Other examples of pro-drug ester groups can be found in, for example, T. Higuchi and V. Stella, in "Pro-drugs as Novel Delivery Systems", Vol. 14, A.C.S. Symposium Series, American Chemical Society (1975); and "Bioreversible Carriers in Drug Design: Theory and Application", edited by E. B. Roche, Pergamon Press: New York, 14-21 (1987) (providing examples of esters useful as prodrugs for compounds containing carboxyl groups). Each of the above-mentioned references is herein incorporated by reference in their entirety.

"Metabolites" of the compounds disclosed herein include active species that are produced upon introduction of the compounds into the biological milieu.

"Solvate" refers to the compound formed by the interaction of a solvent and a compound described herein, a metabolite, or salt thereof. Suitable solvates are pharmaceutically acceptable solvates including hydrates.

The term "pharmaceutically acceptable salt" refers to salts that retain the biological effectiveness and properties of a compound, which are not biologically or otherwise undesirable for use in a pharmaceutical. In many cases, the compounds herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297. Johnston et al., published Sep. 11, 1987 (incorporated by reference herein in its entirety).

When referring to numerical values, the terms "or ranges including and/or spanning the aforementioned values" (and variations thereof) is meant to include any range that includes or spans the aforementioned values. For example, when the temperature of a reaction is expressed as "20° C., 30° C., 40° C., 50° C., or ranges including and/or spanning the aforementioned values." this includes the particular temperature provided or temperature ranges spanning from 20° C. to 50° C., 20° C. to 40° C., 20° C. to 30° C., 30° C. to 50° C., 30° C. to 40° C., or 40° C. or 50° C.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, cycloalkynyl, aryl, or heteroaryl group. That is, the alkyl, alkenyl, alkynyl, ring of the cycloalkyl, ring of the cycloalkenyl, ring of the cycloalkynyl, ring of the aryl, or the ring of the heteroaryl can contain from "a" to "b", inclusive, carbon atoms. Thus, for example, a "$C_1$ to $C_4$ alkyl" group refers to all alkyl groups having from 1 to 4 carbons (e.g., 1, 2, 3, or 4), that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. A "$C_1$ to $C_6$ alkyl" group refers to all alkyl groups having from 1 to 6 carbons (e.g., 1, 2, 3, 4, 5, or 6). If no "a" and "b" are designated with regard to an alkyl, alkenyl, alkynyl, cycloalkyl cycloalkenyl, cycloalkynyl, aryl, or heteroaryl group, the ranges described in these definitions are included (including the broadest ranges).

As used herein, "alkyl" refers to a straight or branched hydrocarbon chain that is fully saturated (i.e., contains no double or triple bonds). The alkyl moiety may be branched or straight chain. Examples of branched alkyl groups include, but are not limited to, iso-propyl, sec-butyl, t-butyl and the like. Examples of straight chain alkyl groups include, but are not limited to, methyl, ethyl, n-propyl, n-butyl, n-pentyl, n-hexyl, n-heptyl and the like. The alkyl group may have 1 to 20 carbon atoms (as disclosed elsewhere herein, whenever it appears herein, a numerical range such as "1 to 20" refers to each integer in the given range; for example, "1 to 20 carbon atoms" means that the alkyl group may consist of 1, 2, 3, 4, 5, 6, 7, 8, 9, 10, 11, 12, 13, 14, 15, 16, 17, 18, 19, or 20 carbon atoms, although the present definition also covers the occurrence of the term "alkyl" where no numerical range is designated). The "alkyl" group may also be a medium size alkyl having 1 to 12 carbon atoms. The "alkyl" group could also be a lower alkyl having 1 to 6 carbon atoms. The alkyl group of the compounds may be designated as "$C_{1-6}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. By way of example only, "$C_1$-$C_8$ alkyl" indicates that there are one to five carbon atoms in the alkyl chain, i.e., the alkyl chain is selected from methyl, ethyl, n-propyl, isopropyl, n-butyl, isobutyl, tert-butyl, pentyl (branched and straight-chained), etc. Typical alkyl groups include, but are in no way limited to, methyl ("Me" or —$CH_3$), ethyl, propyl, isopropyl, butyl, isobutyl, tertiary butyl, pentyl, hexyl, and the like. An alkyl group may be unsubstituted or substituted.

As used herein, "alkenyl" refers to an alkyl group that contains in the straight or branched hydrocarbon chain one or more double bonds. As noted in the definition of "alkyl", an alkenyl group may be unsubstituted or substituted.

As used herein, "alkynyl" refers to an alkyl group that contains in the straight or branched hydrocarbon chain one or more triple bonds. As noted in the definition of "alkyl", an alkynyl group may be unsubstituted or substituted.

As used herein, the term "alkylene" refers to a bivalent fully saturated straight chain aliphatic hydrocarbon group. Examples of alkylene groups include, but are not limited to, methylene, ethylene, propylene, butylene, pentylene, hexylene, heptylene and octylene. An alkylene group may be represented by , followed by the number of carbon atoms, followed by a "*". For example,

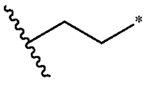 [SMILES: *CC*]

to represent ethylene. The alkylene group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkylene" where no numerical range is designated). The alkylene group may also be a medium size alkyl having 1 to 12 carbon atoms. The alkylene group could also be a lower alkyl having 1 to 6 carbon atoms. For example, a lower alkylene group can be substituted by replacing one or more hydrogen of the lower alkylene group and/or by substituting both hydrogens on the same carbon with a $C_{3-6}$ monocyclic cycloalkyl group (e.g., 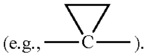 ).

It also is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —$CH_2$—, —$CH_2CH_2$—, —$CH_2CH(CH_3)$ $CH_2$—, and the like. Other radical naming conventions clearly indicate that the radical is a di-radical such as "alkylene" or "alkenylene." An alkylene group may be substituted or unsubstituted.

The term "halogen" or "halo," as used herein, means any one of the radio-stable atoms of column 7 of the Periodic Table of the Elements, e.g., fluorine (—F), chlorine (—Cl), bromine (—Br), or iodine (—I).

As used herein, "haloalkyl" refers to a straight- or branched-chain alkyl group, substituting one or more hydrogens with halogens. Examples of haloalkyl groups include, but are not limited to, —$CF_3$, —$CHF_2$, —$CH_2F$, —$CH_2CF_3$, —$CH_2CHF_2$, —$CH_2CH_2F$, —$CH_2CH_2Cl$, —$CH_2CF_2CF_3$ and other groups that in light of the ordinary skill in the art and the teachings provided herein, would be considered equivalent to any one of the foregoing examples. The haloalkyl may be a medium sized or lower haloalkyl. An haloalkyl group may be substituted or unsubstituted.

As used herein, "alkoxy" refers to the formula —OR wherein R is an alkyl as is defined above, such as "$C_{1-9}$ alkoxy", including but not limited to methoxy, ethoxy, n-propoxy. 1-methylethoxy (isopropoxy), n-butoxy, iso-butoxy, sec-butoxy, and tert-butoxy, and the like. An alkoxy group may be substituted or unsubstituted.

As used herein, "polyethylene glycol" refers to the formula

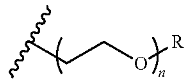

wherein n is an integer greater than one and R is a hydrogen or alkyl. The number of repeat units "n" may be indicated by referring to a number of members. Thus, for example, "2- to 5-membered polyethylene glycol" refers to n being an integer selected from two to five. In some embodiments, R is selected from methoxy, ethoxy, n-propoxy, 1-methylethoxy (isopropoxy), n-butoxy, iso-butoxy, sec-butoxy, and tert-butoxy.

As used herein, "heteroalkyl" refers to a straight or branched hydrocarbon chain (e.g., alkyl) containing one or more heteroatoms. A heteroatom is given its plain and ordinary meaning in organic chemistry, which includes an element other than carbon, including but not limited to, nitrogen (e.g., amino, etc.), oxygen (e.g., alkoxy, ether, hydroxyl, etc.), sulfur, and halogens. The heteroalkyl group may have 1 to 20 carbon atoms although the present definition also covers the occurrence of the term "heteroalkyl" where no numerical range is designated. The heteroalkyl group may also be a medium size heteroalkyl having 1 to 12 carbon atoms. The heteroalkyl group could also be a lower heteroalkyl having 1 to 6 carbon atoms. In various embodiments, the heteroalkyl may have from 1 to 4 heteroatoms, from 1 to 3 heteroatoms, 1 or 2 heteroatoms, or 1 heteroatom. The heteroalkyl group of the compounds may be designated as "$C_{1-4}$ heteroalkyl" or similar designations. The heteroalkyl group may contain one or more heteroatoms. By way of example only, "$C_{1-4}$ heteroalkyl" indicates that there are one to four carbon atoms in the heteroalkyl chain and additionally one or more heteroatoms in the backbone of the chain. A heteroalkyl group may be substituted or unsubstituted.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl." "$C_6$ or $C_{10}$ aryl," or similar designations. For example, the aryl group can be a $C_6$-$C_{14}$ aryl group, a $C_6$-$C_{10}$ aryl group, or a $C_6$ aryl group. Examples of aryl groups include, but are not limited to, phenyl, naphthyl, azulenyl, and anthracenyl. An aryl group may be substituted or unsubstituted.

As used herein, "aryloxy" and "arylthio" refers to RO— and RS—, in which R is an aryl as is defined above, such as "$C_{6-10}$ aryloxy" or "$C_{6-10}$ arylthio" and the like, including but not limited to phenyloxy. An aryloxy or arylthio group may be substituted or unsubstituted.

An "aralkyl" or "arylalkyl" is an aryl group connected, as a substituent, via an alkylene group, such "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-6}$ alkylene group). An aralkyl or arylalkyl group may be substituted or unsubstituted.

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system can be aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. For example, the heteroaryl group can contain 4 to 14 ring members (atoms in the ring(s)), 5 to 10 ring members (atoms in the ring(s)), 5 to 7 ring members (atoms in the ring(s)), 5 to 6 ring members (atoms in the ring(s)). The heteroaryl group may be designated as "5-7 membered heteroaryl," "5-10 membered heteroaryl." or similar designations. In various embodiments, a heteroaryl contains from 1 to 4 heteroatoms, from 1 to 3 heteroatoms, from 1 to 2 heteroatoms, or 1 heteroatom. For example, in various embodiments, a heteroaryl contains 1 to 4 nitrogen atoms, 1 to 3 nitrogen atoms, 1 to 2 nitrogen atoms, 2 nitrogen atoms and 1 sulfur or oxygen atom, 1 nitrogen atom and 1 sulfur or oxygen atom, or 1 sulfur or oxygen atom. Examples of heteroaryl rings include, but are not limited to, furan (e.g., furyl), furazan (e.g., furazanyl), thiophene (e.g., thienyl), benzothiophene (e.g., benzothienyl), phthalazine (e.g., phthalazinyl), pyrrole (e.g., pyrrolyl), oxazole (e.g., oxazolyl), benzoxazole (e.g., benzoxazolyl), 1,2,3-oxadiazole, 1,2,4-oxadiazole, thiazole (e.g., thiazolyl), 1,2,3-thiadiazole, 1,2,4-thiadiazole, benzothiazole (e.g., benzothiazolyl), imidazole (e.g., imidazolyl), benzimidazole (e.g., benzimidazolyl), indole (e.g., indolyl), isoindole (e.g., isoindolyl), indazole, pyrazole (e.g., pyrazolyl), benzopyrazole, isoxazole (e.g., isoxazolyl), benzoisoxazole, isothiazole (e.g., isothiazolyl), triazole (e.g., triazolyl), benzotriazole, thiadiazole (e.g., thiadiazolyl), tetrazole, pyridine (e.g., pyridinyl), pyridazine (e.g., pyridazinyl), pyrimidine (e.g., pyrimidinyl), pyrazine (e.g., pyrazinyl), purine, pteridine, quinoline (e.g., quinolinyl), isoquinoline (e.g., isoquinlinyl), quinazoline, quinoxaline, cinnoline, and triazine (e.g., triazinyl). Heteroaryl rings may also include bridge head nitrogen atoms. For example but not limited to: pyrazolo[1,5-a]pyridine, imidazo[1,2-a]pyridine, and pyrazolo[1,5-a]pyrimidine. A heteroaryl group may be substituted or unsubstituted.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. A heteroaralkyl group may be substituted or unsubstituted.

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl. A carbocyclyl group may be substituted or unsubstituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s), or as otherwise noted herein. A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

A "(carbocyclyl)alkyl" is a carbocyclyl group connected, as a substituent, via an alkylene group, such as "$C_{4-10}$ (carbocyclyl)alkyl" and the like, including but not limited to, cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

As used herein, "cycloalkenyl" means a carbocyclyl ring or ring system having at least one double bond, wherein no ring in the ring system is aromatic. An example is cyclohexenyl, cycloalkenyl groups can contain 4 to 10 atoms in the ring(s). A cycloalkenyl group may be substituted or unsubstituted.

As used herein, "heterocyclyl" or "heteroalicyclyl" refers to three-, four-, five-, six-, seven-, eight-, nine-, ten-, eleven-, twelve-, thirteen-, up to 20-membered monocyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) may be present in either a non-aromatic or aromatic ring in the ring system. The heteroatom(s) is an element other than carbon including, but not limited to, oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heteroalicyclic may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, malcimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, 3,4-methylenedioxyphenyl). The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. A heterocyclyl group may be substituted or unsubstituted.

In various embodiments, a heterocyclyl contains from 1 to 4 heteroatoms, from 1 to 3 heteroatoms, from 1 to 2 heteroatoms, or 1 heteroatom. For example, in various embodiments, a heterocyclyl contains 1 to 4 nitrogen atoms, 1 to 3 nitrogen atoms, 1 to 2 nitrogen atoms, 2 nitrogen atoms and 1 sulfur or oxygen atom, 1 nitrogen atom and 1 sulfur or oxygen atom, or 1 sulfur or oxygen atom. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline. A sulfur of the heterocyclyl ring may be provided as a dioxide (e.g., $—S(O)_2—$).

A "(heterocyclyl)alkyl" is a heterocyclyl group connected, as a substituent, via an alkylene group. Examples include, but are not limited to, imidazolinylmethyl and indolinylethyl.

A "(heterocyclyl)alkynyl" is a heterocyclyl group connected, as a substituent, via an alkynylene group.

As used herein, "acyl" refers to —C(═O)R, wherein R is hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein. Non-limiting examples include formyl, acetyl, propanoyl, benzoyl, and acryl. An acyl group may be substituted or unsubstituted.

An "O-carboxy" group refers to a "—OC(═O) R" group in which R is selected from hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein. An O-carboxy can be substituted or unsubstituted.

A "C-carboxy" group (or "ester") refers to a "—C(═O) OR" group in which R is selected from hydrogen, $—NH_2$, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein. A non-limiting example includes carboxyl (i.e., —C(═O) OH). A C-carboxy can be substituted or unsubstituted.

As used herein, the term "hydroxy" refers to a —OH group.

A "cyano" group refers to a "—CN" group.

A "cyanato" group refers to an "—OCN" group.

An "isocyanato" group refers to a "—NCO" group.

A "thiocyanato" group refers to a "—SCN" group.

An "isothiocyanato" group refers to an "—NCS" group.

A "sulfinyl" group refers to an "—S(═O) R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. A sulfinyl can be substituted or unsubstituted.

A "sulfonyl" group refers to an "—$SO_2$R" or "—$SO_2$—" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. A sulfonyl can be provided in a heterocyclyl ring. A sulfonyl can be substituted or unsubstituted.

An "S-sulfonamido" group refers to a "—$SO_2NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. $R_A$ and $R_B$ may be taken together to provide a heteroaryl or heterocycle. A S-sulfonamido can be substituted or unsubstituted.

An "N-sulfonamido" group refers to a "—N($R_A$) $SO_2R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. An N-sulfonamido can be substituted or unsubstituted.

An "O-carbamyl" group refers to a "—OC(═O) $NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. $R_A$ and $R_B$ may be taken together to provide a heteroaryl or heterocycle. An O-carbamyl can be substituted or unsubstituted.

An "N-carbamyl" group refers to an "—N($R_A$) OC(═O) $R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. An N-carbamyl can be substituted or unsubstituted.

An "O-thiocarbamyl" group refers to a "—OC(═S) $NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. $R_A$ and $R_B$ may be taken together to provide a heteroaryl or heterocycle. An O-thiocarbamyl can be substituted or unsubstituted.

An "N-thiocarbamyl" group refers to an "—N($R_A$) OC(═S) $R_B$" group in which $R_A$ and $R_B$ are each independently selected from hydrogen, $C_{1-6}$ alkyl, $C_{2-6}$ alkenyl, $C_2$-6 alkynyl, $C_{3-7}$ carbocyclyl, $C_{6-10}$ aryl, 5-10 membered heteroaryl, and 5-10 membered heterocyclyl, as defined herein. An N-thiocarbamyl can be substituted or unsubstituted.

A "C-amido" group refers to a "—C(═O) $NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl. $C_{6-10}$ aryl, 5-10 membered heteroaryl, and 5-10 membered heterocyclyl, as defined herein. $R_A$ and $R_B$ may be taken together to provide a heteroaryl or heterocycle. A C-amido can be substituted or unsubstituted.

An "N-amido" group refers to a "—N($R_A$) C(═O) $R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. $R_A$ and $R_B$ may be taken together to provide a heteroaryl or heterocycle. An N-amido can be substituted or unsubstituted.

A "carbamido" or "carbamide" group refers to a "(RARB) NC(═O) N(RC)" group in which $R_A$, $R_B$, and RC can be independently hydrogen, alkyl, alkenyl, alkynyl, carbocyclyl, aryl, heteroaryl, heterocyclyl, aralkyl, or heterocyclyl (alkyl), as defined herein. A carbamido may be substituted or unsubstituted.

An "amino" group refers to a "—$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl. 5-10 membered heteroaryl, and 5-10 membered heterocyclyl, as defined herein. $R_A$ and $R_B$ may be taken together to provide a heteroaryl or heterocycle. An amino can be substituted or unsubstituted.

An "alkamino" group refers to a "—$NR_AR_B$" group in which $R_A$ is alkyl and $R_B$ is independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. An alkamino can be substituted or unsubstituted.

An "aminoalkyl" group refers to an amino group connected via an alkylene group. An aminoalkyl can be substituted or unsubstituted.

An "alkoxyalkyl" group refers to an alkoxy group connected via an alkylene group, such as a "$C_{2-8}$ alkoxyalkyl" and the like. An alkoxyalkyl can be substituted or unsubstituted.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl (optionally substituted with—OH or C-carboxy), $C_1$-$C_6$ alkenyl, $C_1$-$C_6$ alkynyl, $C_1$-$C_6$ heteroalkyl, $C_3$-$C_7$ carbocyclyl (optionally substituted with halo, —OH, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with N-amido, —OH, halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl ($C_1$-$C_6$)alkyl (optionally substituted with halo, $C_1$-$C_6$ alkyl, $C_1$-$C_6$ alkoxy. $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl ($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), haloalkoxy, cycloalkenyl, halo, cyano, hydroxy, $C_1$-$C_6$ alkoxy, $C_1$-$C_6$ alkoxy ($C_1$-$C_6$)alkyl (i.e., ether), aryloxy, sulfhydryl (mercapto), halo($C_1$-$C_6$)alkyl (e.g., $CF_3$), halo($C_1$-$C_6$)alkoxy (e.g., —$OCF_3$), $C_1$-$C_6$ alkylthio, arylthio, amino, amino ($C_1$-$C_6$)alkyl, a mono-substituted amine group, a di-substituted amine group, a mono-substituted amine (alkyl), a di-substituted amine (alkyl), nitro, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfenyl, sulfinyl, sulfonyl, —O—$NH_2$, oxo (=O), a diamino-group, a polyamino, a diether-group, and a polyether (e.g., diethylene glycol, triethylene glycol, oligoethylene glycol, polyethylene glycol, etc.). Wherever a group is described as "optionally substituted" (or other similar language) or as comprising one or more "optional substitutions," that group can be substituted with the above substituents or can be unsubstituted.

In some embodiments, substituted group(s) is (are) substituted with one or more substituent(s) individually and independently selected from $C_1$-$C_4$ alkyl, amino, hydroxy, and halogen.

Two substituents may come together with the atom or atoms to which they are attached to form a ring that is spiro or fused with the rest of the compound.

As used herein, any "R" group(s) such as, without limitation, $R^1$, $R^2$, $R^3$, etc., represent substituents that can be attached to the indicated atom. An R group may be substituted or unsubstituted. If two "R" groups are described as being "taken together" (or similar language), the R groups and the atoms they are attached to can form a cycloalkyl, aryl, heteroaryl or heterocycle. When two R groups are said to form a ring (e.g., a carbocyclyl, heterocyclyl, aryl, or heteroaryl ring) "together with the atom to which they are attached," it is meant that the collective unit of the atom and the two R groups are the recited ring. The ring is not otherwise limited by the definition of each R group when taken individually. For example, when the following substructure is present:

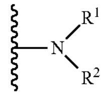

and $R^1$ and $R^2$ are defined as selected from the group consisting of hydrogen and alkyl, or $R^1$ and $R^2$ together with the nitrogen to which they are attached form a heterocyclyl, it is meant that $R^1$ and $R^2$ can be selected from hydrogen or alkyl, or alternatively, the substructure has structure:

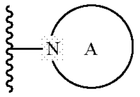

where ring A is a heterocyclyl ring containing the depicted nitrogen. As further illustration, without limitation, if $R^{1a}$ and $R^{1b}$ of an $NR^{1a}$ $R^{1b}$ group are indicated to be "taken together," it means that they are covalently bonded to one another to form a ring:

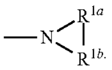

A cyclic structure may be shown using provided using the following structure (or a similar structure with a different ring size, heteroatoms, etc.):

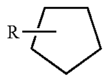

When a cyclic structure is illustrated using this type of structure, what is meant is that the R group may be attached to any position of the ring by replacing an —H of the ring with —R. For example, for the following ring:

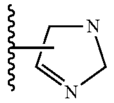

includes any of the following ring structures:

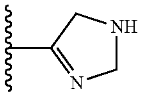

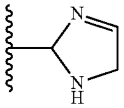

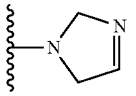

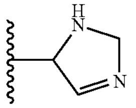

where "⌇" indicates a bond to a remaining portion of the structure. Likewise, the following structure:

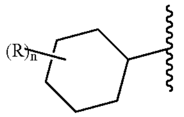

where "⌇" indicates a bond to a remaining portion of the structure and n is 1 to 5, any of the following structures are envisioned or other variations (as would be readily appreciated by the one of skill in the art):

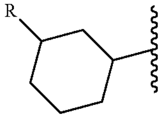

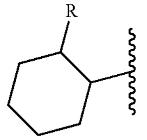

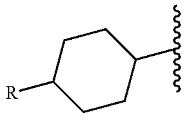

-continued

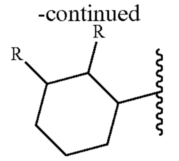

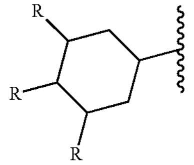

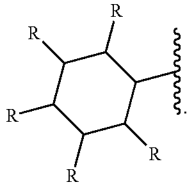

When two "adjacent" R groups are said to form a ring "together with the atoms to which they are attached," it is meant that the collective unit of the atoms, intervening bonds, and the two R groups are the recited ring. For example, when the following substructure is present:

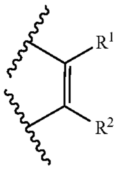

and $R^1$ and $R^2$ are defined as selected from the group consisting of hydrogen and alkyl, or $R^1$ and $R^2$ together with the atoms to which they are attached form an aryl or carbocyclyl, it is meant that $R^1$ and $R^2$ can be selected from hydrogen or alkyl, or alternatively, the substructure has structure:

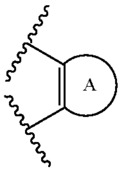

where A is an aryl ring or a carbocyclyl containing the depicted double bond.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

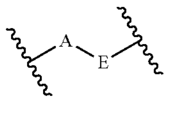

includes the substituent being oriented such that the "A" is attached at the leftmost attachment point of the molecule as well as the case in which "A" is attached at the rightmost attachment point of the molecule.

As noted in the definition for alkylene, it also is to be understood that certain radical naming conventions can include either a mono-radical or a di-radical, depending on the context. For example, where a substituent (e.g., in a genus structure) requires two points of attachment to the rest of the molecule, it is understood that the substituent is a di-radical. For example, a substituent identified as aminoalkyl that requires two points of attachment includes di-radicals such as $—NHCH_2—$, $—NHCH_2CH_2—$, $—NHCH_2CH(CH_3)\ CH_2—$, and the like. Other examples a substituent may require two points of attachment include alkoxy, aryl, heteroaryl, carbocyclyl, heterocyclyl, etc.

As used herein, a radical indicates species with a single, unpaired electron such that the species containing the radical can be covalently bonded to another species. Hence, in this context, a radical is not necessarily a free radical. Rather, a radical indicates a specific portion of a larger molecule.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof. It is understood that, in any compound described herein having one or more chiral centers, all possible diastereomers are also envisioned. It is understood that, in any compound described herein all tautomers are envisioned. It is also understood that, in any compound described herein, all isotopes of the included atoms are envisioned. For example, any instance of hydrogen, may include hydrogen-1 (protium), hydrogen-2 (deuterium), hydrogen-3 (tritium) or other isotopes; any instance of carbon may include carbon-12, carbon-13, carbon-14, or other isotopes; any instance of oxygen may include oxygen-16, oxygen-17, oxygen-18, or other isotopes; any instance of fluorine may include one or more of fluorine-18, fluorine-19, or other isotopes; any instance of sulfur may include one or more of sulfur-32, sulfur-34, sulfur-35, sulfur-36, or other isotopes.

As used herein, the term "inhibitor" means any compound, molecule or composition that inhibits or reduces the activity of a target biomolecule. The inhibition can be achieved by, for example, blocking phosphorylation of the target (e.g., competing with adenosine triphosphate (ATP), a phosphorylating entity), by binding to a site outside the active site, affecting its activity by a conformational change, or by depriving kinases of access to the molecular chaperoning systems on which they depend for their cellular stability, leading to their ubiquitylation and degradation.

As used herein, the term "vanin 1" is an enzyme with pantetheinase activity, which catalyzes the hydrolysis of pantetheine into pantothenic acid and cysteamine. Vanin-1 is member of a larger vanin family, consisting of three human (VNN1, VNN2 and VNN3) and two mouse (Vnn1 and Vnn3) orthologous genes. Vanins play a role in inflammation, oxidative stress and cell migration processes that are mediated via vanin-dependent cysteamine production.

As used herein, "subject," "host." "patient," and "individual" are used interchangeably and shall be given its ordinary meaning and shall also refer to an organism that has VNN1 proteins. This includes mammals, e.g., a human, a non-human primate, ungulates, canines, felines, equines, mice, rats, and the like. The term "mammal" includes both human and non-human mammals.

"Diagnosis" as used herein shall be given its ordinary meaning and shall also include determination of a subject's susceptibility to a disease or disorder, determination as to whether a subject is presently affected by a disease or disorder, prognosis of a subject affected by a disease or disorder (e.g., identification of cancer or cancerous states, stages of cancer, or responsiveness of cancer to therapy), and use of therametrics (e.g., monitoring a subject's condition to provide information as to the effect or efficacy of therapy).

The term "sample" or "biological sample" shall be given its ordinary meaning and also encompasses a variety of sample types obtained from an organism and can be used in an imaging, a diagnostic, a prognostic, or a monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

As used herein, a "natural amino acid side chain" refers to the side-chain substituent of a naturally occurring amino acid. Naturally occurring amino acids have a substituent attached to the α-carbon. Naturally occurring amino acids include Arginine, Lysine, Aspartic acid, Glutamic acid, Glutamine, Asparagine, Histidine, Serine, Threonine, Tyrosine, Cysteine, Methionine, Tryptophan, Alanine, Isoleucine, Leucine, Phenylalanine, Valine, Proline, and Glycine.

As used herein, a "non-natural amino acid side chain" refers to the side-chain substituent of a non-naturally occurring amino acid. Non-natural amino acids include β-amino acids ($\beta^3$ and $\beta^2$), Homo-amino acids, Proline and Pyruvic acid derivatives, 3-substituted Alanine derivatives, Glycine derivatives, Ring-substituted Phenylalanine and Tyrosine Derivatives, Linear core amino acids and N-methyl amino acids. Exemplary non-natural amino acids are available from Sigma-Aldridge, listed under "unnatural amino acids & derivatives." See also, Travis S. Young and Peter G. Schultz, "Beyond the Canonical 20 Amino Acids: Expanding the Genetic Lexicon," J. Biol. Chem. 2010 285:11039-11044, which is incorporated by reference in its entirety.

The term "agent" or "test agent" includes any substance, molecule, element, compound, entity, or a combination thereof. It includes, but is not limited to, e.g., protein, polypeptide, peptide or mimetic, small organic molecule, polysaccharide, polynucleotide, and the like. It can be a natural product, a synthetic compound, or a chemical compound, or a combination of two or more substances. Unless otherwise specified, the terms "agent", "substance", and "compound" are used interchangeably herein.

The term "analog" is used herein to refer to a molecule that structurally resembles a reference molecule but which has been modified in a targeted and controlled manner, by replacing a specific substituent of the reference molecule with an alternate substituent. Compared to the reference molecule, an analog would be expected, by one skilled in the art, to exhibit the same, similar, or improved utility. Synthesis and screening of analogs, to identify variants of known compounds having improved characteristics (such as higher binding affinity for a target molecule) is an approach that is well known in pharmaceutical chemistry.

The "patient" or "subject" treated as disclosed herein is, in some embodiments, a human patient, although it is to be understood that the principles of the presently disclosed subject matter indicate that the presently disclosed subject matter is effective with respect to all vertebrate species, including mammals, which are intended to be included in the terms "subject" and "patient." Suitable subjects are generally mammalian subjects. The subject matter described herein finds use in research as well as veterinary and medical applications. The term "mammal" is used in its usual biological sense. Thus, it specifically includes, but is not limited to, primates, including simians (chimpanzees, apes, monkeys) and humans, cattle, horses, sheep, goats, swine, rabbits, dogs, cats, rats and mice but also includes many other species.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

An "effective amount" or a "therapeutically effective amount" as used herein refers to an amount of a therapeutic agent that is effective to relieve, to some extent, or to reduce the likelihood of onset of, one or more of the symptoms of a disease or condition, and includes curing a disease or condition. "Curing" means that the symptoms of a disease or condition are eliminated; however, certain long-term or permanent effects may exist even after a cure is obtained (such as extensive tissue damage).

"Treat," "treatment," or "treating." as used herein refers to administering a pharmaceutical composition for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject.

As used herein, the term "weight percent," when referring to a component, is the weight of the component divided by the weight of the composition that includes the component, multiplied by 100%. For example, the weight percent of component A when 5 grams of component A is added to 95 grams of component B is 5% (e.g., 5 g A/(5 g A+95 g B)×100%).

The term "control" refers shall be given its ordinary meaning and shall also include a sample or standard used for comparison with a sample which is being examined, processed, characterized, analyzed, etc. In several embodiments, the control is a sample obtained from a healthy patient or a non-tumor tissue sample obtained from a patient diagnosed with a tumor. In several embodiments, the control is a historical control or standard reference value or range of values. In several embodiments, the control is a comparison to a wild-type VNN1 arrangement or scenario.

Terms and phrases used in this application, and variations thereof, especially in the appended claims, unless otherwise expressly stated, should be construed as open ended as opposed to limiting. As examples of the foregoing, the term "including" should be read to mean "including, without limitation," "including but not limited to," or the like; the term "comprising" as used herein is synonymous with "including." "containing," or "characterized by," and is inclusive or open-ended and does not exclude additional, unrecited elements or method steps; the term "having" should be interpreted as "having at least;" the term "includes" should be interpreted as "includes but is not limited to;" the term "example" is used to provide exemplary instances of the item in discussion, not an exhaustive or limiting list thereof; and use of terms like "preferably." "preferred." "desired," or "desirable," and words of similar meaning should not be understood as implying that certain features are critical, essential, or even important to the structure or function of the invention, but instead as merely intended to highlight alternative or additional features that may or may not be utilized in a particular embodiment of the invention. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Additionally, the phrase "consisting essentially of" will be understood to include those elements specifically recited and those additional elements that do not materially affect the basic and novel characteristics of the claimed technology. The phrase "consisting of" excludes any element not specified.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

The section headings used herein are for organizational purposes only and are not to be construed as limiting the subject matter described. Features disclosed under one heading (such as a composition) can be used in combination with features disclosed under a different heading (a method of treating).

Introduction

Vanin 1's enzymatic activity is associated with several inflammatory diseases, including ulcerative colitis, Crohn's disease, lupus, atherosclerosis, Type 1 diabetes, atopic dermatitis and psoriasis. Various small molecules inhibitors have been developed in the past to regulate and/or block the activity of vanin 1. Small molecule inhibitors of the enzyme vascular non-inflammatory molecule-1 (vanin 1), have been used to treat inflammatory and autoimmune disease. However, despite the fact that various inhibitors of vanin 1 are known, there remains a need for selective inhibitors to be used for the treatment of diseases which offer one or more advantages over current compounds. Those advantages include: improved activity and/or efficacy; beneficial target selectivity profile according to the respective therapeutic need; improved side effect profile, such as fewer undesired side effects, lower intensity of side effects; improved targeting of mutant receptors in diseased cells; improved physicochemical properties, such as solubility/stability in water, body fluids, and/or pharmaceutical formulations; improved pharmacokinetic properties, allowing e.g. for dose reduction or an easier dosing scheme; easier drug substance manufacturing e.g. by shorter synthetic routes or easier purification. Several embodiments disclosed herein pertain to compounds that achieve one or more of these advantages (or others). Several embodiments disclosed herein pertain to compounds that address one or more deficiencies of known drug substances.

Compounds of Formula (I)

Several embodiments pertain to pyrrole compounds. Several embodiments pertain to carboxy pyrrole compounds. In several embodiments, the carboxy pyrrole is a compound having the structure of Formula (I) (or a pharmaceutically acceptable salt thereof):

(I)

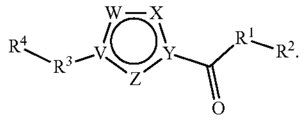

In several embodiments, V, W, X, Y, and Z are each independently selected from the group consisting of C, $C(R^5)$, N, and $NR^6$. In several embodiments, at least one instance of V, W, X, Y, and Z is N or $NR^6$ with the remaining variables being C or $C(R^5)$.

In several embodiments, $R^1$ is selected from the group consisting of optionally substituted $C_{1-3}$ alkylene, optionally substituted 3-12 membered heterocyclyl, and —$NR^7$—, or R' is not present. In several embodiments, where an intermediate variable (e.g., a variable that is between two other structural features) is described as optionally being "not present," when not present, the variable can be expressed as a single bond between two adjacent groups. For example, where $R^1$ is not present, $R^2$ may be directly connected to the Y-adjacent carbonyl (C═O) shown in Formula (I).

In several embodiments, $R^2$ is either not present or, where present, is selected from the group consisting of —H, —OH, optionally substituted alkyl, optionally substituted N-amido, optionally substituted $C_{6-10}$ aryl. 5-10 optionally substituted heteroaryl, selected from the group consisting of optionally substituted $C_{6-10}$ aryl, optionally substituted 5-10 membered heteroaryl, optionally substituted 3-10 membered carbocyclyl, and optionally substituted 3-12 membered heterocyclyl. In several embodiments, where a terminal variable (e.g., a variable providing a terminal end of a structure, such as $R^2$) is described as optionally being "not present," when not present, the variable can be expressed as a hydrogen atom on the next structural feature that is present. For example, if $R^2$ is not present and $R^1$ is —$NR^7$-then $R^1R^2$ may be expressed together as —$NR^7H$ (e.g., —$NH_2$). In several embodiments, $R^2$ is optionally substituted 3-10 membered heterocyclyl (e.g., a 3—, 4-, 5-, 6-, 7-, 8-, 9-, or 10-membered heterocyclyl). In several embodiments, where $R^2$ is a heterocyclyl, as disclosed elsewhere herein, the heterocyclyl may comprise more than one ring and the rings may provide a spirocyclic arrangement.

In several embodiments, $R^3$ selected from the group consisting of optionally substituted $C_{1-3}$ alkylene, —$NR^7$—, —C(═O)—, —C(═O) NH—, and —C(═O) $NR^7$—, or $R^3$ is not present.

In several embodiments. $R^4$ is selected from the group consisting of optionally substituted $C_{6-10}$ aryl, optionally substituted 5-10 membered heteroaryl, optionally substituted 3-10 membered heterocyclyl, and optionally substituted $C_{1-6}$ alkyl, or $R^4$ is not present.

In several embodiments, each instance of $R^5$, $R^6$ and $R^7$, where present, is independently selected from the group consisting of —H, halogen, hydroxy, optionally substituted $C_{1-6}$ alkyl, optionally substituted $C_1$-$C_6$ alkoxy, $C_{1-6}$ haloalkyl, optionally substituted $C_{6-10}$ aryl, optionally substituted $C_{6-10}$ benzyl, and optionally substituted $C_{3-7}$ carbocyclyl. As disclosed herein, where more than one instance of a variable is present and those variables are described as being independently selected from a group of possible structures, each instance of that variable may be a different structure in the group. Thus, for illustration, where more than one instance of $R^5$ is present and $R^5$ is described as independently selected from—H, halogen, and hydroxy, each instance of $R^5$ may be selected from the group consisting of —H, halogen, and hydroxy.

In several embodiments, as disclosed elsewhere herein, the variables defined for one structural formula may be also be used for any other formula having that same variable. For example, when a variable has the same alphanumeric designation (e.g., $R^2$) for one formula (e.g., Formula I), that definition of the variable can be used in other formulae (e.g., Formula Ic) having that variable, even where the variable is not specifically defined for those other formulae.

In several embodiments, $R^1$ is alkylene optionally substituted with $C_{6-10}$ aryl. In several embodiments, $R^1$ is heterocyclyl optionally substituted with $C_{1-6}$ alkyl (e.g., methyl). In several embodiments, $R^1$ is alkylene optionally substituted with phenyl.

In several embodiments, $R^2$ is optionally substituted with one or more (e.g., 1, 2, 3, 4, or 5) halogen atoms (e.g., —F or —Cl). In several embodiments, $R^2$ is —N(Me) C(═O) $C_1$-6 alkyl.

In several embodiments, $R^4$ is optionally substituted with one or more (e.g., 1, 2, 3, 4, or 5) halogen atoms (e.g., —F or —Cl), one or more hydroxyl atoms, or one or more $C_{1-3}$ alkyl groups.

In several embodiments, $R^6$ is —H or methyl.

In several embodiments, $R^7$ is —H or methyl.

In several embodiments, Formula (I) may be represented by one or more of the following compounds (or others):

Compound 1

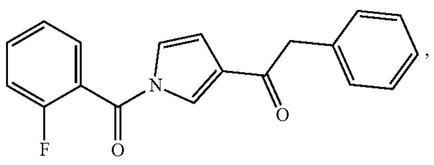

-continued

Compound 2

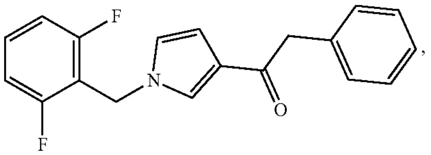

Compound 3

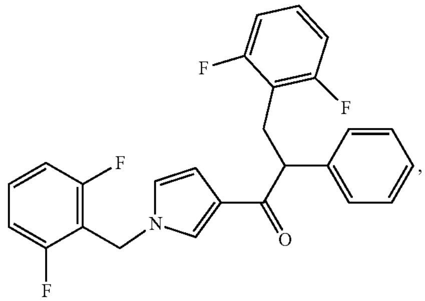

Compound 4

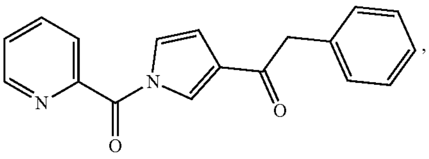

Compound 5

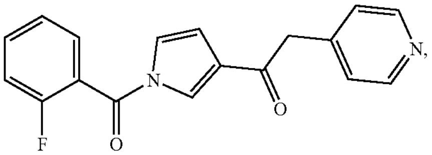

Compound 6

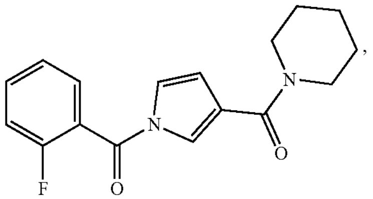

Compound 7

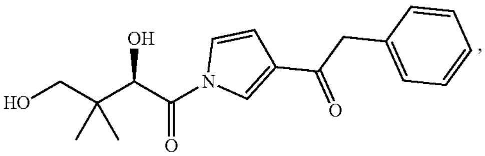

Compound 8

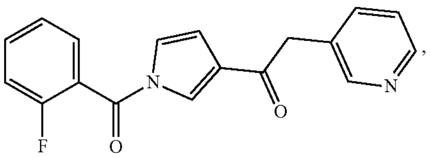

Compound 9

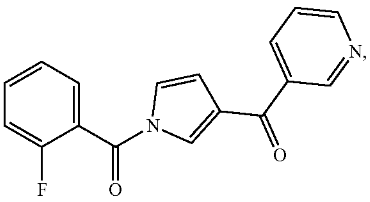

-continued
Compound 10
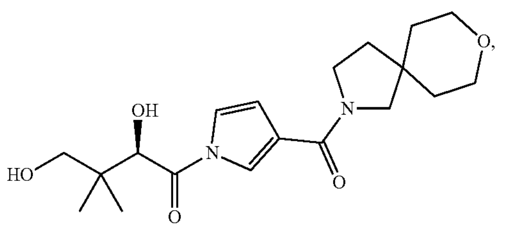
Compound 11
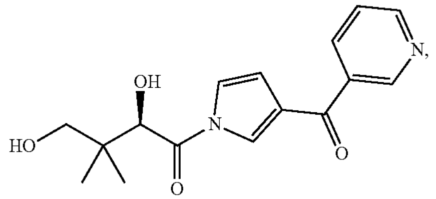
Compound 12
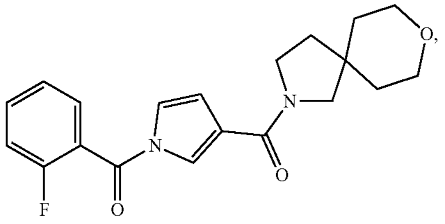
Compound 13
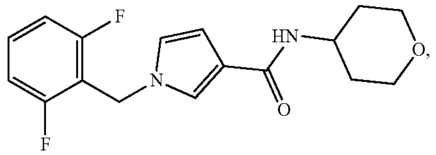
Compound 14
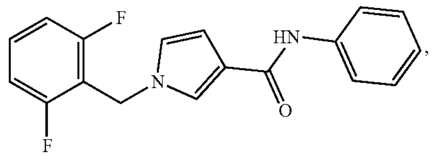
Compound 15
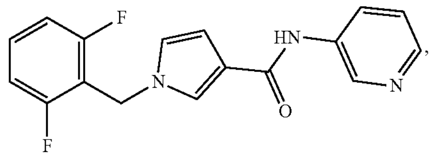
Compound 16
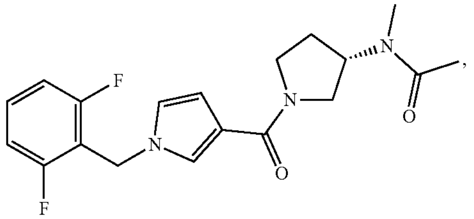
-continued
Compound 17
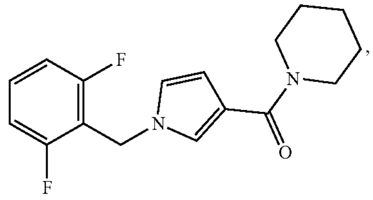
Compound 18
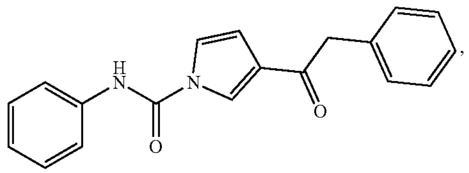
Compound 19
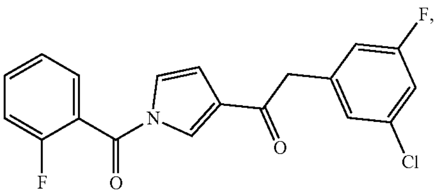
Compound 20
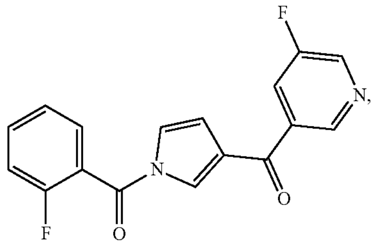
Compound 21
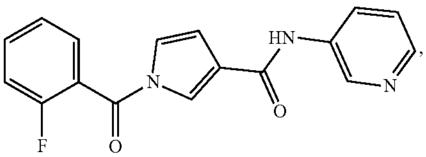
Compound 22
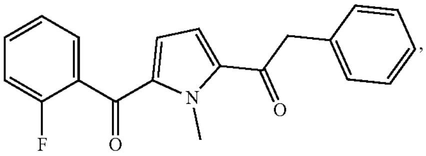
Compound 23
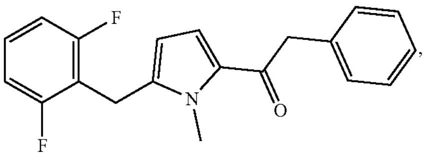

-continued
Compound 24
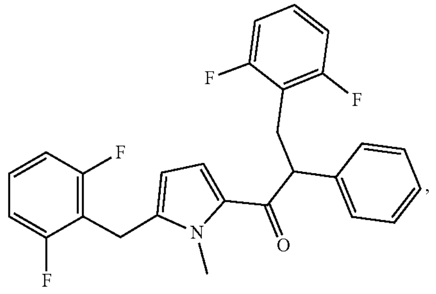
Compound 25
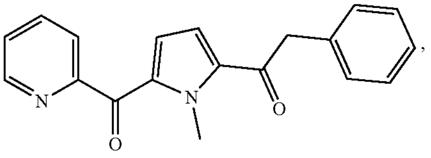
Compound 26
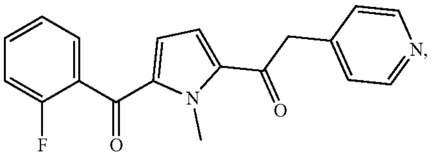
Compound 27
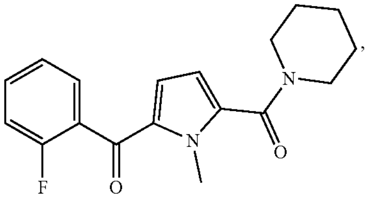
Compound 28
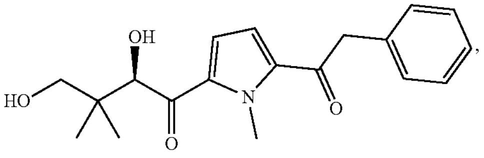
Compound 29
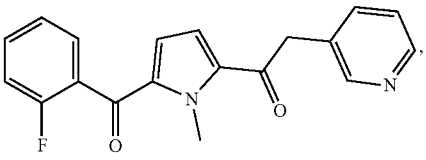
Compound 30
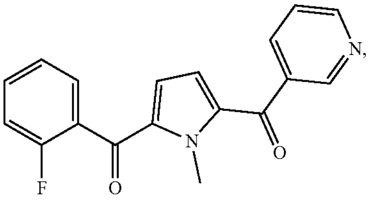
-continued
Compound 31
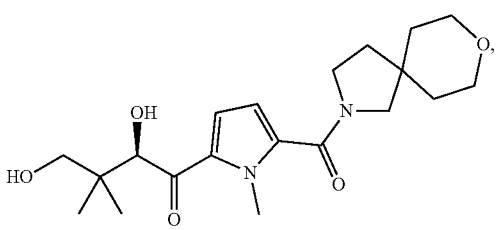
Compound 32
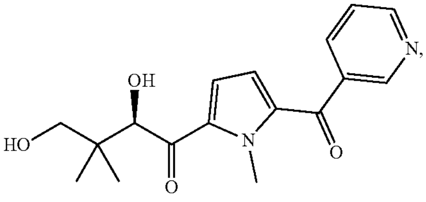
Compound 33
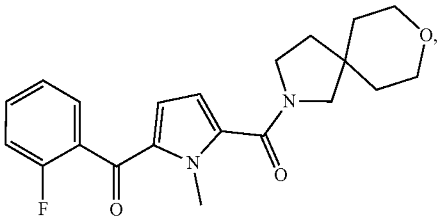
Compound 34
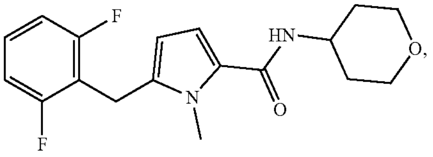
Compound 35
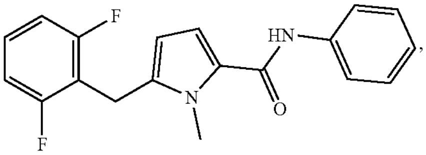
Compound 36
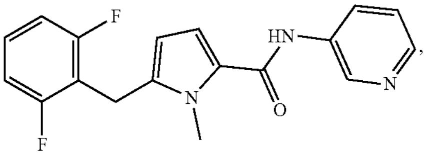
Compound 37
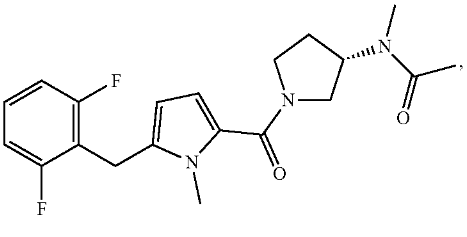

-continued
Compound 38
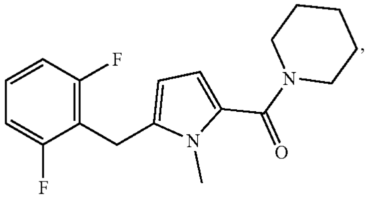
Compound 39
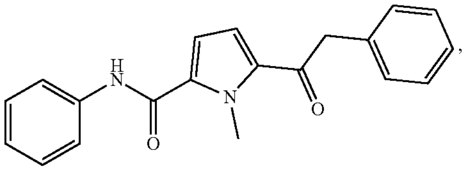
Compound 40
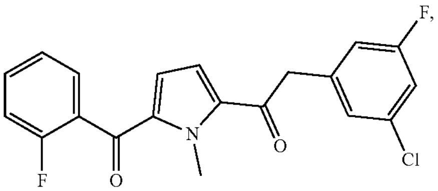
Compound 41
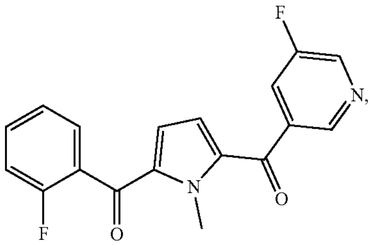
Compound 42
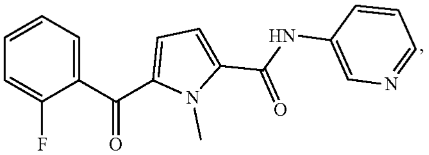
Compound 43
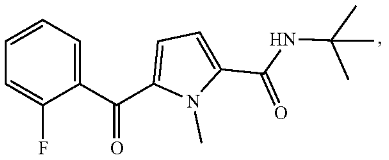
Compound 44
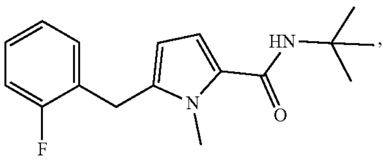
Compound 45
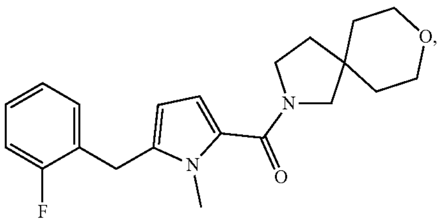
-continued
Compound 46
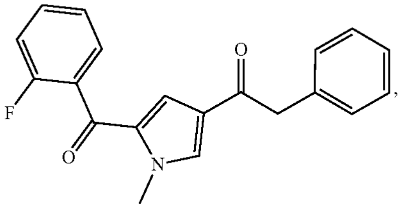
Compound 47
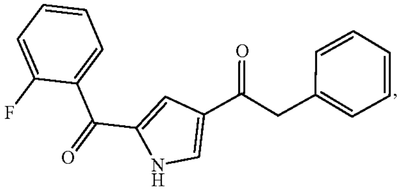
Compound 48
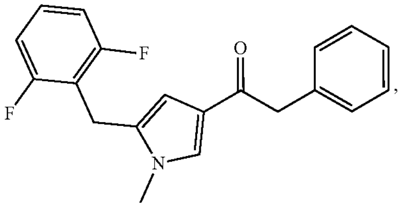
Compound 49
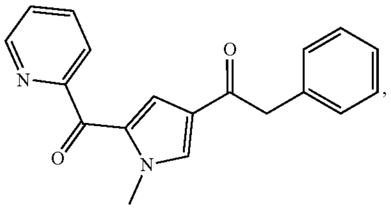
Compound 50
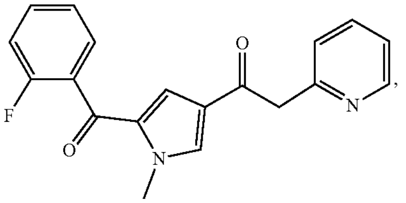
Compound 51
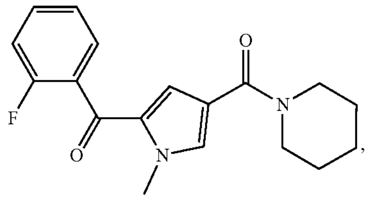
Compound 52
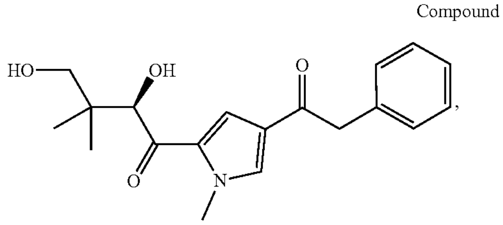

-continued
Compound 53
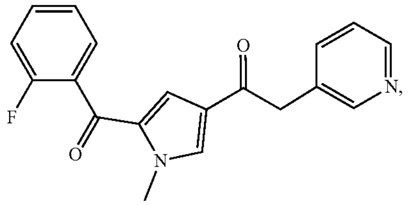
Compound 54
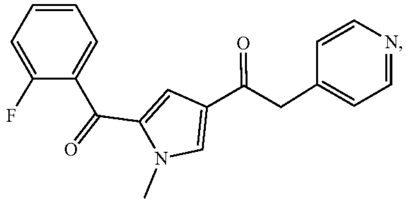
Compound 55
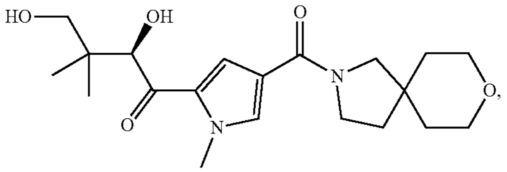
Compound 56
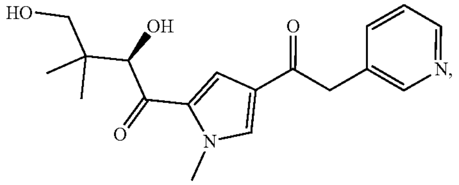
Compound 57
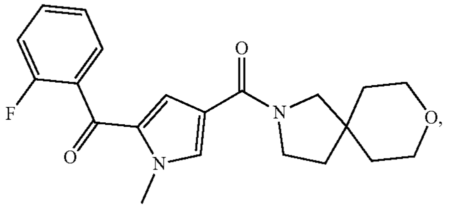
Compound 58
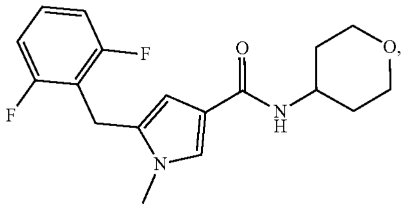
Compound 59
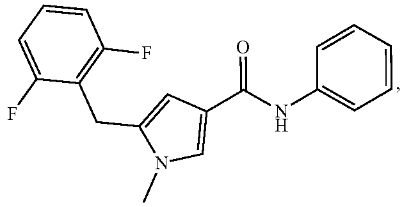
-continued
Compound 60
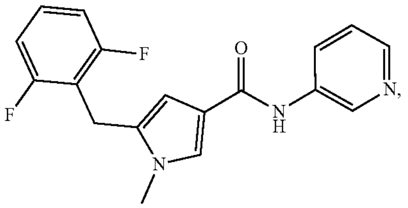
Compound 61
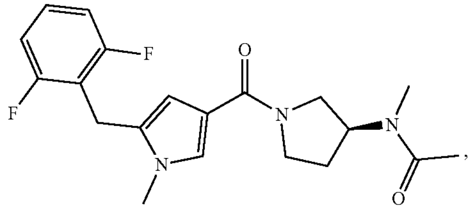
Compound 62
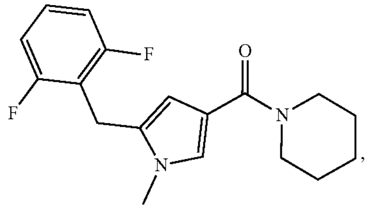
Compound 63
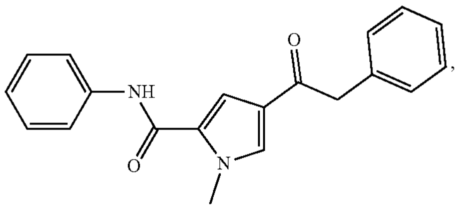
Compound 64
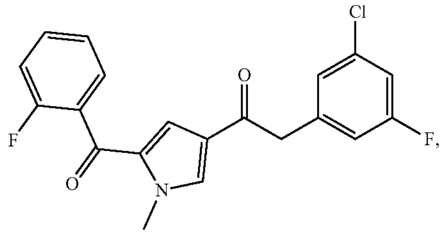
Compound 65
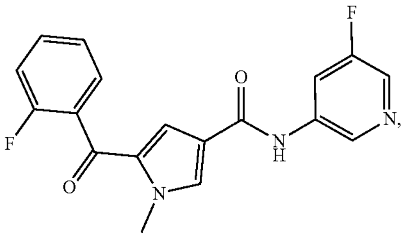
Compound 66
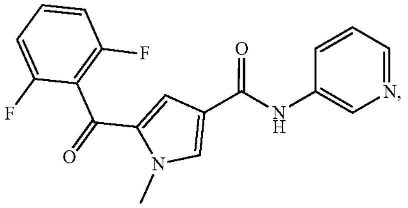

-continued
Compound 67
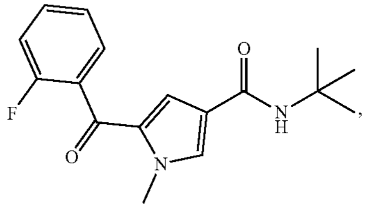
Compound 68
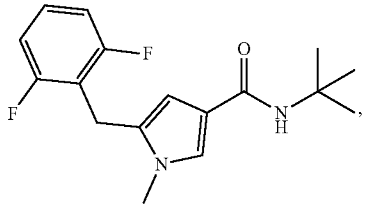
Compound 69
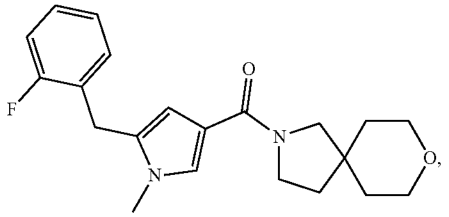
Compound 70
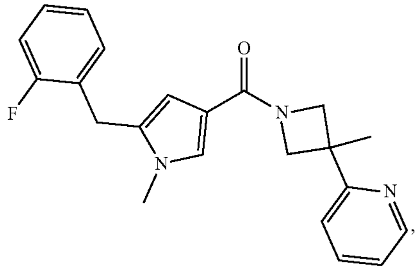
Compound 71
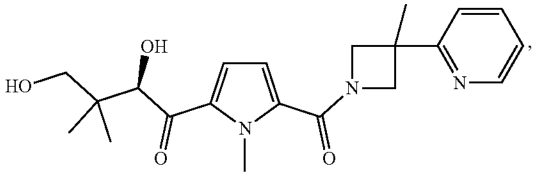
Compound 72
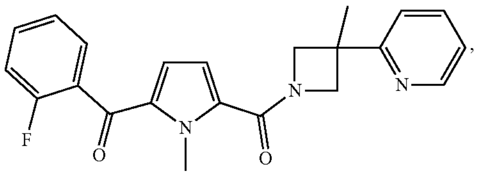
Compound 73
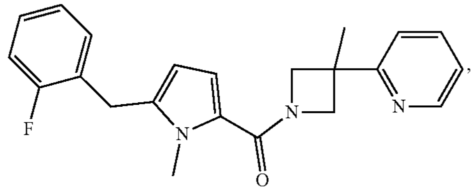
-continued
Compound 74
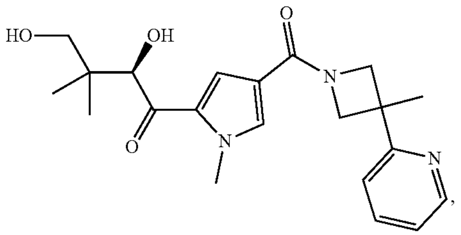
Compound 75
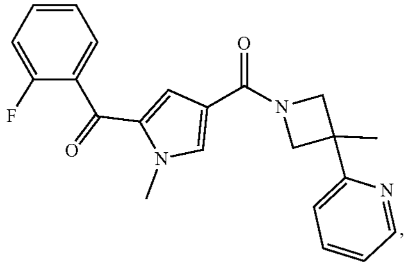
Compound 76
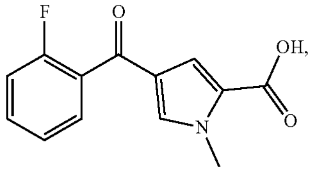
Compound 77
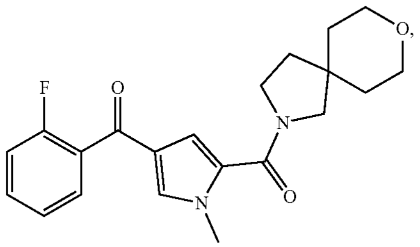
Compound 78
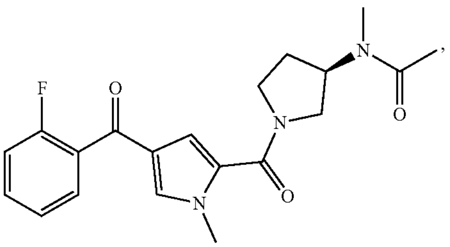
Compound 79
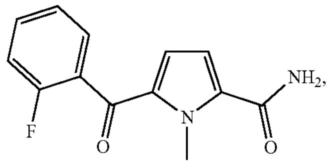
Compound 80
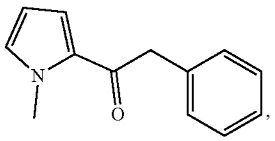
and -continued Compound 81

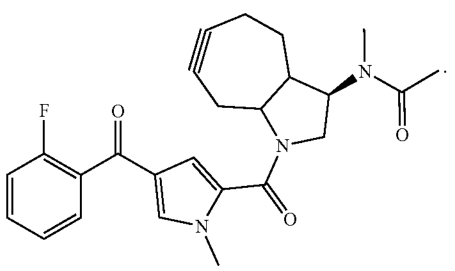

Any one of the directly preceding structures may be further optionally substituted by replacing one or more-H atoms of any carbon or nitrogen atom present within the structure.

In some embodiments, the compound having the structure of Formula (I) is selected from one or more of the following:

1-(1-(2-fluorobenzoyl)-1H-pyrrol-3-yl)-2-phenylethan-1-one;

1-(1-(2,6-difluorobenzyl)-1H-pyrrol-3-yl)-2-phenylethan-1-one;

1-(1-(2,6-difluorobenzyl)-1H-pyrrol-3-yl)-3-(2,6-difluorophenyl)-2-phenylpropan-1-one;

2-phenyl-1-(1-picolinoyl-1H-pyrrol-3-yl) ethan-1-one;

1-(1-(2-fluorobenzoyl)-1H-pyrrol-3-yl)-2-(pyridin-4-yl) ethan-1-one;

(1-(2-fluorobenzoyl)-1H-pyrrol-3-yl) (piperidin-1-yl) methanone;

(R)-2,4-dihydroxy-3,3-dimethyl-1-(3-(2-phenylacetyl)-1H-pyrrol-1-yl) butan-1-one;

1-(1-(2-fluorobenzoyl)-1H-pyrrol-3-yl)-2-(pyridin-3-yl) ethan-1-one;

(1-(2-fluorobenzoyl)-1H-pyrrol-3-yl) (pyridin-3-yl) methanone;

(R)-1-(3-(8-oxa-2-azaspiro[4.5]decane-2-carbonyl)-1H-pyrrol-1-yl)-2,4-dihydroxy-3,3-dimethylbutan-1-one;

(R)-2,4-dihydroxy-3,3-dimethyl-1-(3-nicotinoyl-1H-pyrrol-1-yl) butan-1-one;

(3-(8-oxa-2-azaspiro[4.5]decane-2-carbonyl)-1H-pyrrol-1-yl) (2-fluorophenyl) methanone;

1-(2,6-difluorobenzyl)-N-(tetrahydro-2H-pyran-4-yl)-1H-pyrrole-3-carboxamide;

1-(2,6-difluorobenzyl)-N-phenyl-1H-pyrrole-3-carboxamide;

1-(2,6-difluorobenzyl)-N-(pyridin-3-yl)-1H-pyrrole-3-carboxamide;

(S)—N-(1-(1-(2,6-difluorobenzyl)-1H-pyrrole-3-carbonyl) pyrrolidin-3-yl)-N-methylacetamide;

(1-(2,6-difluorobenzyl)-1H-pyrrol-3-yl) (piperidin-1-yl) methanone;

N-phenyl-3-(2-phenylacetyl)-1H-pyrrole-1-carboxamide;

2-(3-chloro-5-fluorophenyl)-1-(1-(2-fluorobenzoyl)-1H-pyrrol-3-yl) ethan-1-one;

(1-(2-fluorobenzoyl)-1H-pyrrol-3-yl) (5-fluoropyridin-3-yl) methanone;

1-(2-fluorobenzoyl)-N-(pyridin-3-yl)-1H-pyrrole-3-carboxamide;

1-(5-(2-fluorobenzoyl)-1-methyl-1H-pyrrol-2-yl)-2-phenylethan-1-one;

1-(5-(2,6-difluorobenzyl)-1-methyl-1H-pyrrol-2-yl)-2-phenylethan-1-one;

1-(5-(2,6-difluorobenzyl)-1-methyl-1H-pyrrol-2-yl)-3-(2,6-difluorophenyl)-2-phenylpropan-1-one;

1-(1-methyl-5-picolinoyl-1H-pyrrol-2-yl)-2-phenylethan-1-one;

1-(5-(2-fluorobenzoyl)-1-methyl-1H-pyrrol-2-yl)-2-(pyridin-4-yl) ethan-1-one;

(5-(2-fluorobenzoyl)-1-methyl-1H-pyrrol-2-yl) (piperidin-1-yl) methanone;

(R)-2,4-dihydroxy-3,3-dimethyl-1-(1-methyl-5-(2-phenylacetyl)-1H-pyrrol-2-yl) butan-1-one;

1-(5-(2-fluorobenzoyl)-1-methyl-1H-pyrrol-2-yl)-2-(pyridin-3-yl) ethan-1-one;

(5-(2-fluorobenzoyl)-1-methyl-1H-pyrrol-2-yl) (pyridin-3-yl) methanone;

(R)-2,4-dihydroxy-3,3-dimethyl-1-(1-methyl-5-(8-oxa-2-azaspiro[4.5]decane-2-carbonyl)-1H-pyrrol-2-yl) butan-1-one;

(R)-2,4-dihydroxy-3,3-dimethyl-1-(1-methyl-5-nicotinoyl-1H-pyrrol-2-yl) butan-1-one;

(5-(2-fluorobenzoyl)-1-methyl-1H-pyrrol-2-yl) (8-oxa-2-azaspiro[4.5]decan-2-yl) methanone;

5-(2,6-difluorobenzyl)-1-methyl-N-(tetrahydro-2H-pyran-4-yl)-1H-pyrrole-2-carboxamide;

5-(2,6-difluorobenzyl)-1-methyl-N-phenyl-1H-pyrrole-2-carboxamide;

5-(2,6-difluorobenzyl)-1-methyl-N-(pyridin-3-yl)-1H-pyrrole-2-carboxamide;

(S)—N-(1-(5-(2,6-difluorobenzyl)-1-methyl-1H-pyrrole-2-carbonyl) pyrrolidin-3-yl)-N-methylacetamide;

(5-(2,6-difluorobenzyl)-1-methyl-1H-pyrrol-2-yl) (piperidin-1-yl) methanone;

1-methyl-N-phenyl-5-(2-phenylacetyl)-1H-pyrrole-2-carboxamide;

2-(3-chloro-5-fluorophenyl)-1-(5-(2-fluorobenzoyl)-1-methyl-1H-pyrrol-2-yl) ethan-1-one;

(5-(2-fluorobenzoyl)-1-methyl-1H-pyrrol-2-yl) (5-fluoropyridin-3-yl) methanone;

5-(2-fluorobenzoyl)-1-methyl-N-(pyridin-3-yl)-1H-pyrrole-2-carboxamide;

N-(tert-butyl)-5-(2-fluorobenzoyl)-1-methyl-1H-pyrrole-2-carboxamide;

N-(tert-butyl)-5-(2-fluorobenzyl)-1-methyl-1H-pyrrole-2-carboxamide;

(5-(2-fluorobenzyl)-1-methyl-1H-pyrrol-2-yl) (8-oxa-2-azaspiro[4.5]decan-2-yl) methanone;

1-(5-(2-fluorobenzoyl)-1-methyl-1H-pyrrol-3-yl)-2-phenylethan-1-one;

1-(5-(2-fluorobenzoyl)-1H-pyrrol-3-yl)-2-phenylethan-1-one;

1-(5-(2,6-difluorobenzyl)-1-methyl-1H-pyrrol-3-yl)-2-phenylethan-1-one;

1-(1-methyl-5-picolinoyl-1H-pyrrol-3-yl)-2-phenylethan-1-one;

1-(5-(2-fluorobenzoyl)-1-methyl-1H-pyrrol-3-yl)-2-(pyridin-2-yl) ethan-1-one;

(5-(2-fluorobenzoyl)-1-methyl-1H-pyrrol-3-yl) (piperidin-1-yl) methanone;

(R)-2,4-dihydroxy-3,3-dimethyl-1-(1-methyl-4-(2-phenylacetyl)-1H-pyrrol-2-yl) butan-1-one;

1-(5-(2-fluorobenzoyl)-1-methyl-1H-pyrrol-3-yl)-2-(pyridin-3-yl) ethan-1-one;

1-(5-(2-fluorobenzoyl)-1-methyl-1H-pyrrol-3-yl)-2-(pyridin-4-yl) ethan-1-one;

(R)-2,4-dihydroxy-3,3-dimethyl-1-(1-methyl-4-(8-oxa-2-azaspiro[4.5]decane-2-carbonyl)-1H-pyrrol-2-yl) butan-1-one;

(R)-2,4-dihydroxy-3,3-dimethyl-1-(1-methyl-4-(2-(pyridin-3-yl) acetyl)-1H-pyrrol-2-yl) butan-1-one;

(5-(2-fluorobenzoyl)-1-methyl-1H-pyrrol-3-yl) (8-oxa-2-azaspiro[4.5]decan-2-yl) methanone;

5-(2,6-difluorobenzyl)-1-methyl-N-(tetrahydro-2H-pyran-4-yl)-1H-pyrrole-3-carboxamide;

5-(2,6-difluorobenzyl)-1-methyl-N-phenyl-1H-pyrrole-3-carboxamide;

5-(2,6-difluorobenzyl)-1-methyl-N-(pyridin-3-yl)-1H-pyrrole-3-carboxamide;

(S)—N-(1-(5-(2,6-difluorobenzyl)-1-methyl-1H-pyrrole-3-carbonyl) pyrrolidin-3-yl)-N-methylacetamide;

(5-(2,6-difluorobenzyl)-1-methyl-1H-pyrrol-3-yl) (piperidin-1-yl) methanone;

1-methyl-N-phenyl-4-(2-phenylacetyl)-1H-pyrrole-2-carboxamide;

2-(3-chloro-5-fluorophenyl)-1-(5-(2-fluorobenzoyl)-1-methyl-1H-pyrrol-3-yl) ethan-1-one;

5-(2-fluorobenzoyl)-N-(5-fluoropyridin-3-yl)-1-methyl-1H-pyrrole-3-carboxamide;

5-(2,6-difluorobenzoyl)-1-methyl-N-(pyridin-3-yl)-1H-pyrrole-3-carboxamide;

N-(tert-butyl)-5-(2-fluorobenzoyl)-1-methyl-1H-pyrrole-3-carboxamide;

N-(tert-butyl)-5-(2,6-difluorobenzyl)-1-methyl-1H-pyrrole-3-carboxamide;

(5-(2-fluorobenzyl)-1-methyl-1H-pyrrol-3-yl) (8-oxa-2-azaspiro[4.5]decan-2-yl) methanone;

(5-(2-fluorobenzyl)-1-methyl-1H-pyrrol-3-yl) (3-methyl-3-(pyridin-2-yl) azetidin-1-yl) methanone;

(R)-2,4-dihydroxy-3,3-dimethyl-1-(1-methyl-5-(3-methyl-3-(pyridin-2-yl) azetidine-1-carbonyl)-1H-pyrrol-2-yl) butan-1-one;

(5-(2-fluorobenzoyl)-1-methyl-1H-pyrrol-2-yl) (3-methyl-3-(pyridin-2-yl) azetidin-1-yl) methanone;

(5-(2-fluorobenzyl)-1-methyl-1H-pyrrol-2-yl) (3-methyl-3-(pyridin-2-yl) azetidin-1-yl) methanone;

(R)-2,4-dihydroxy-3,3-dimethyl-1-(1-methyl-4-(3-methyl-3-(pyridin-2-yl) azetidine-1-carbonyl)-1H-pyrrol-2-yl) butan-1-one;

(5-(2-fluorobenzoyl)-1-methyl-1H-pyrrol-3-yl) (3-methyl-3-(pyridin-2-yl) azetidin-1-yl) methanone;

4-(2-fluorobenzoyl)-1-methyl-1H-pyrrole-2-carboxylic acid;

(4-(2-fluorobenzoyl)-1-methyl-1H-pyrrol-2-yl) (8-oxa-2-azaspiro[4.5]decan-2-yl) methanone;

1-(1-(2-fluorobenzoyl)-1H-pyrrol-3-yl)-2-phenylethan-1-one;

1-(5-(2-fluorobenzoyl)-1-methyl-1H-pyrrol-3-yl)-2-phenylethan-1-one; and 5-(2-fluorobenzoyl)-1-methyl-1H-pyrrole-2-carboxamide.

In several embodiments, as disclosed elsewhere herein, the variables defined for one structural formula may be also be used for any other formula having that same variable. For example, as disclosed elsewhere herein, when a variable has the same alphanumeric designation (e.g., $R^2$) for one formula (e.g., Formula (Id) or (I), etc.), that definition of the variable can be used in other formulae (e.g., Formula (Ib), (Ie), etc.), even where the variable is not specifically defined for those other formulae. Thus, the like variables of Formula (I) may be defined as provided for any one of Formulae (Ia), (Ib), (Ic), (Id), (Ie), (Ia1), (Ib1), (Ia2), (Ib2), (Ia3), (Ib3), (Ia4), (Ib4), (Ia5), (Ib5), or vice versa. Similarly, the like variables of Formula (Ia) may be defined as provided for any one of Formulae (I), (Ib), (Ic), (Id), (Ie), (Ia1), (Ib1), (Ia2), (Ib2), (Ia3), (Ib3), (Ia4), (Ib4), (Ia5), (Ib5), or vice versa, and so on.

Formulae (Ia), (Ib), (Ic), (Id), & (Ie)

Several exemplary embodiments of structures of Formula (I) may be represented by the structure of Formula (Ia), a 3-carboxy pyrrole, where V is N; each instance of W, X, and Z is $C(R^5)$, $R^5$ is —H; and Y is C:

(Ia)

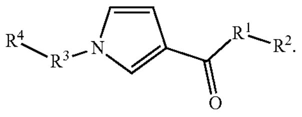

Several exemplary embodiments of structures of Formula (I) may be represented by the structure of Formula (Ib), a 5-carboxy pyrrole, where V is C; each instance of W and X is $C(R^5)$ where $R^5$ is —H; Y is C; and Z is $NR^6$:

(Ib)

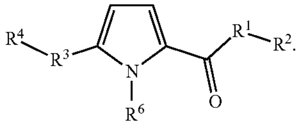

Several exemplary embodiments of structures of Formula (I) may be represented by the structure of Formula (Ic), a 4-carboxy pyrrole, where V is C; W is $NR^6$; each instance of X and Z is $C(R^5)$ where $R^5$ is —H; and Y is C:

(Ic)

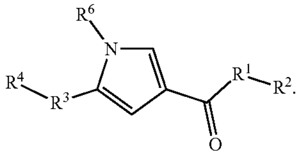

Several exemplary embodiments of structures of Formula (I) may be represented by the structure of Formula (Id), a 5-carboxy pyrrole, where V is C, each instance of W and Z is $C(R^5)$ where $R^5$ is —H; X is $NR^6$; and Y is C:

(Id)

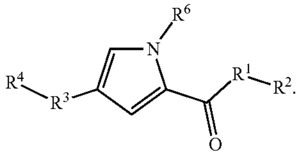

Several exemplary embodiments of structures of Formula (I) may be represented by the structure of Formula (Ie), a 1-carboxy pyrrole, where V is C, each instance of W, X and Z is $C(R^5)$ where $R^5$ is —H; and Y is N:

(Ie)

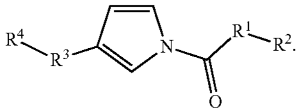

In several embodiments, each variable of any one of Formulae (Ia)-(Ie) is as defined elsewhere herein (e.g., as defined in Formula (I) or elsewhere).

In several embodiments, $R^1$ is selected from the group consisting of —NH—, —$CH_2$—, —$CHR^8$, and —$C(R^8)_2$, or $R^1$ is not present. In several embodiments, each instance of $R^8$, where present, is independently selected from the group consisting of halogen, hydroxy, optionally substituted $C_{1-6}$ alkyl, optionally substituted $C_1$-$C_6$ alkoxy, optionally substituted $C_{1-6}$ haloalkyl, optionally substituted $C_{6-10}$ aryl, optionally substituted $C_{6-10}$ aralkyl, optionally substituted $C_{6-10}$ haloaralkyl, and optionally substituted $C_{3-7}$ carbocyclyl. In several embodiments, $R^1$ is selected from the group consisting of:

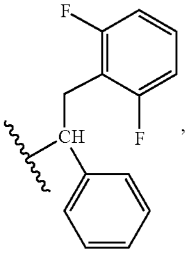,
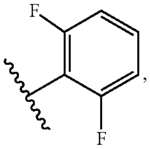,
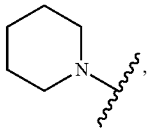,
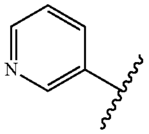,
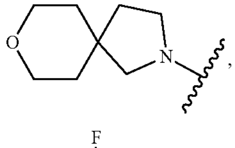,
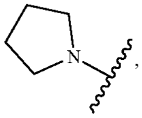, and
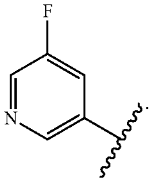.

Any one of the directly preceding structures may be further optionally substituted by replacing one or more-H atoms of any carbon or nitrogen atom present within the structure.

In several embodiments, $R^2$ is selected from the group consisting of optionally substituted $C_{6-10}$ aryl, optionally substituted 5-10 membered heteroaryl, optionally substituted 3-10 membered heterocyclyl, optionally substituted N-amido, and optionally substituted C-amido. In several embodiments, $R^2$ is selected from the group consisting of:

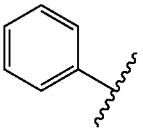,
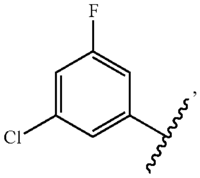,
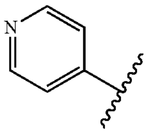,
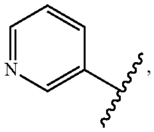,
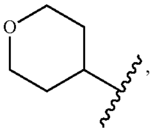,
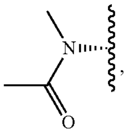, and
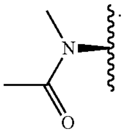.

Any one of the directly preceding structures may be further optionally substituted by replacing one or more-H atoms of any carbon or nitrogen atom present within the structure. In several embodiments, N-amido is represented by:

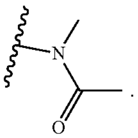 [SMILES: *N(C)C(C)=O].

In several embodiments, $R^3$ is —$C(R^6)_2$—, —C(O)—, or —C(O) $NR^6$—. In several embodiments, each instance of $R^6$, where present, is independently selected from the group consisting of —H, halogen, hydroxy, $C_{1-6}$ alkyl, $C_1$-$C_6$ alkoxy, $C_{1-6}$ haloalkyl, and $C_{6-10}$ aryl. In several embodiments, $R^3$ is selected from the group consisting of —$CH_2$— and —C(=O)—. In several embodiments, $R^3$ is selected from the group consisting of —$CH_2$—, —C(=O)—, and —C(=O) NH—.

In several embodiments, $R^4$ is selected from the group consisting of optionally substituted $C_{6-10}$ aryl, optionally substituted 5-10 membered heteroaryl, optionally substituted 3-10 membered heterocyclyl, and optionally substituted $C_{1-6}$ alkyl. In several embodiments, $R^4$ is selected from the group consisting of:

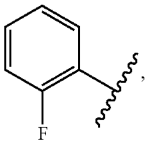,
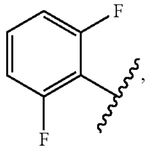,
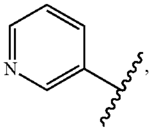,
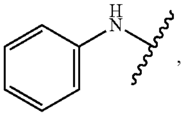, and
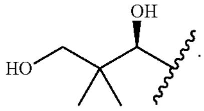.

Any one of the directly preceding structures may be further optionally substituted by replacing one or more-H atoms of any carbon or nitrogen atom present within the structure.

In several embodiments, when any one or more of $R^1$, $R^2$, $R^3$, or $R^4$ is optionally substituted, one or more optional substitutions of $R^1$, $R^2$, $R^3$, or $R^4$ are independently selected from the group consisting of halogen, hydroxy, $C_{1-6}$ alkyl, $C_{1-6}$ alkoxy, aryl, N-amido, and heteroaryl. In several embodiments, when substituted any one of $R^1$, $R^2$, $R^3$, or $R^4$ may have one, two, three, four, or five optional substitutions. In several embodiments, when $R^2$ is optionally substituted, one or more optional substitutions of $R^2$ are independently selected from the group consisting of halogen (e.g., —F, —Cl, etc.), hydroxy, $C_{1-6}$ alkyl (—Me, ethyl, propyl, etc.), $C_{1-6}$ alkoxy, aryl, heteroaryl, N-amido, and C-amido. In several embodiments, N-amido is:

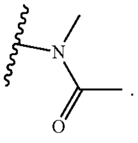 [SMILES: *N(C)C(C)=O].

Formulae (Ia1) & (Ib1)

In several embodiments of Formula (I), $R^2$ is:

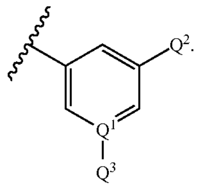

In several embodiments, Formula (I) may be represented by the structure of: Formula (Ia1), a 3-carboxy pyrrole, where V is N; each instance of W, X, and Z is $C(R^5)$ where $R^5$ is —H; and Y is C; or Formula (Ib1), a 5-carboxy pyrrole, where V is C; each instance of W and X is $C(R^5)$ where $R^5$ is —H; Y is C; and Z is $NR^6$ and each other variable is as defined elsewhere herein (e.g., as defined in Formula (I)):

(Ia1)

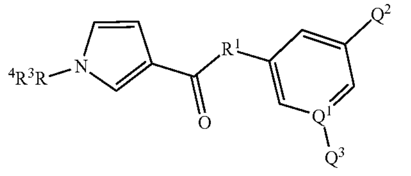

(Ib1)

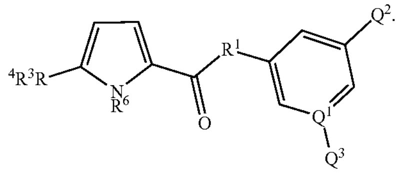

In several embodiments, $R^1$ is —$CH_2$— or —NH—. In several embodiments, $Q^1$ is C or N. In several embodiments, each instance of $Q^2$ and $Q^3$, when present, is independently selected from the group consisting of —H, halogen, hydroxy, $C_{1-6}$ alkyl, $C_1$-$C_6$ alkoxy, $C_{1-6}$ haloalkyl, and nitro; with the proviso that when $Q^1$ is N, then $Q^3$ is absent. In several embodiments, $R^3$ is selected from the group consisting of —$CH_2$—, —C(═O)—, and —C(═O) NH—. In several embodiments, $R^4$ is optionally substituted $C_{6-10}$ aryl or optionally substituted 5-10 membered heteroaryl. In several embodiments, $R^6$ is selected from the group consisting of —H, $C_{1-6}$ alkyl, $C_{1-6}$ haloalkyl, and $C_{6-10}$ aryl. In several embodiments, $R^6$ is $C_{1-6}$ alkyl. In several embodiments, $R^6$ is methyl.

Formula (Ia2) & (Ib2) Compounds

Several exemplary embodiments of structures of Formulae (I), where $R^1$ is $C_1$ alkylene, $R^2$ is phenyl, and $R^6$ is $C_1$ alkyl, may be represented by the structure of Formula (Ia2), a 3-carboxy pyrrole, where V is N; each instance of W, X, and Z is $C(R^5)$ where $R^5$ is —H; and Y is C; or Formula (Ib2), a 5-carboxy pyrrole, where V is C; each instance of W and X is $C(R^5)$ where $R^5$ is —H; Y is C; and Z is $NR^6$ and each other variable is as defined elsewhere herein (e.g., as defined in Formula (I)):

(Ia2)

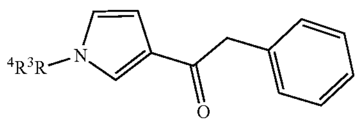

(Ib2)

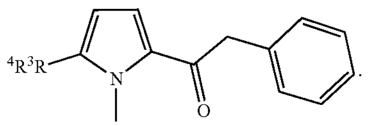

In several embodiments, $R^4$ is selected from the group consisting of:

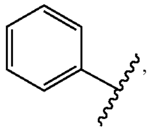, 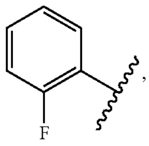, 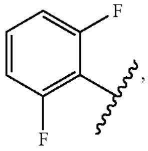 [SMILES: *c1c(F)cccc1F], 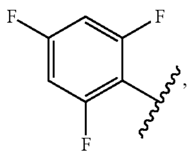, 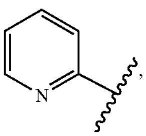, 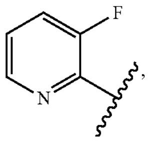, 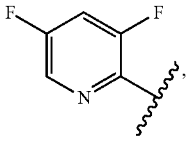, 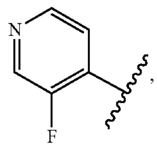, and 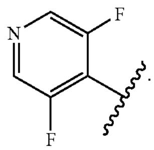.

Any one of the directly preceding structures may be further optionally substituted by replacing one or more-H atoms of any carbon or nitrogen atom present within the structure.

Several embodiments are represented by the structure of Formula (Ia2), where $R^3$ is —C(═O)—, and each other variable of the structure of Formula (Ia2) is as defined elsewhere herein. In several embodiments, where $R^3$ is —C(═O)— and $R^4$ is selected from:

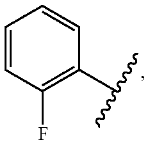, 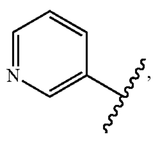, 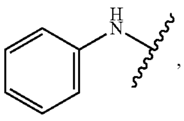, and 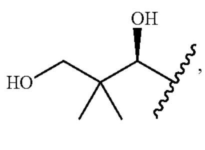, and each other variable is as defined elsewhere herein, Formula (Ia2) may be represented by any one of the following compounds (or others):

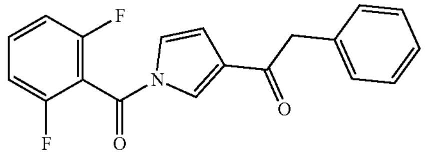

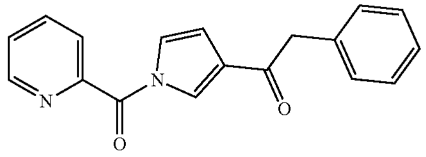

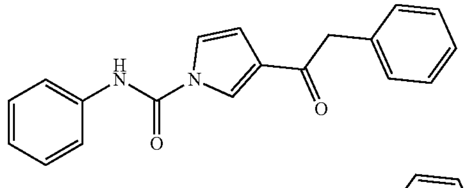

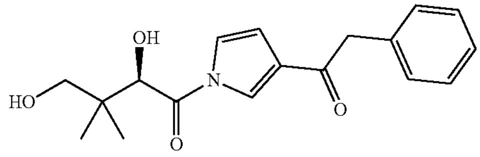

Several embodiments are represented by the structure of Formula (Ia2), where $R^3$ is —$CH_2$—, and each other variable of the structure of Formula (Ia2) is as defined elsewhere herein. In several embodiments, where $R^3$ is —$CH_2$— and $R^4$ is:

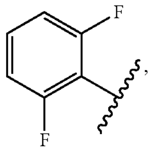

and each other variable is as defined elsewhere herein, Formula (Ia2) may be represented by the following compound (or others):

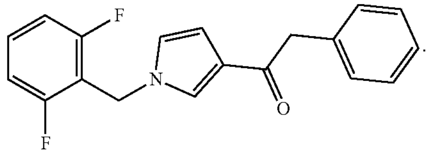 [SMILES: O=C(Cc1ccccc1)c1ccn(Cc2c(F)cccc2F)c1]

Several embodiments are represented by the structure of Formula (Ib2), where $R^3$ is —C(═O)—, and each other variable of the structure of Formula (Ib2) is as defined elsewhere herein. In several embodiments, where $R^3$ is —C(═O)— and $R^4$ is selected from:

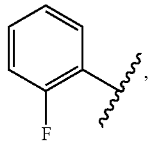
,
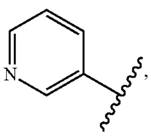
,

-continued

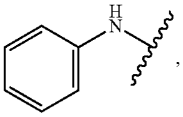
, and
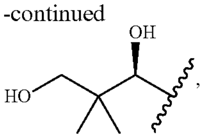
, and each other variable is as defined elsewhere herein, Formula (Ib2) may be represented by any one of the following compounds (or others):

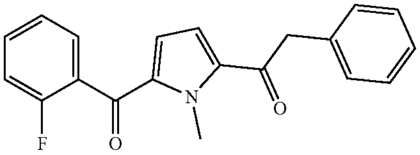

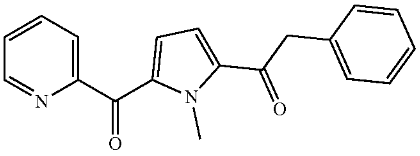

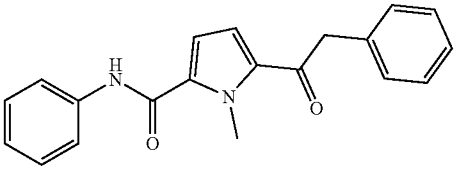

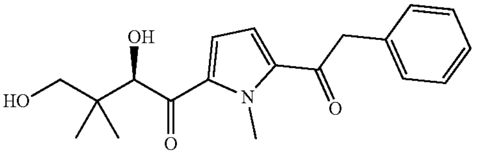

Several embodiments are represented by the structure of Formula (Ib2), where $R^3$ is —$CH_2$—, and each other variable of the structure of Formula (Ib2) is as defined elsewhere herein. In several embodiments, where $R^3$ is —$CH_2$— and $R^4$ is:

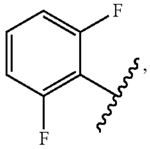

and each other variable is as defined elsewhere herein, Formula (Ib2) may be represented by the following compound (or others):

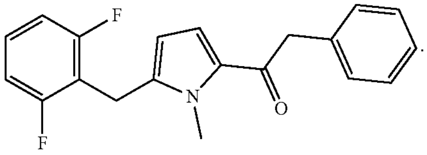 [SMILES: Cn1c(Cc2c(F)cccc2F)ccc1C(=O)Cc1ccccc1]

Formula (Ia3) & (Ib3) Compounds

In several exemplary embodiments of structures of Formula (I), $R^3$ is —C(═O)— and $R^4$ and $R^3$ taken together are:

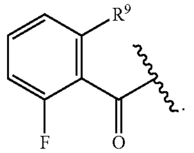

In several embodiments, Formula (I) may be represented by the structure of: Formula (Ia3), a 3-carboxy pyrrole, where V is N; each instance of W, X, and Z is $C(R^5)$ where $R^5$ is —H; and Y is C; or Formula (Ib3), a 5-carboxy pyrrole, where V is C; each instance of W and X is $C(R^5)$ where $R^5$ is —H; Y is C; and Z is $NR^6$ and each other variable is as defined elsewhere herein (e.g., as defined in Formula (I)):

(Ia3)

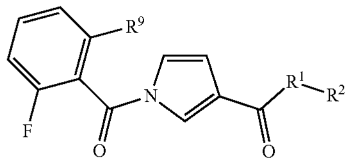

(Ib3)

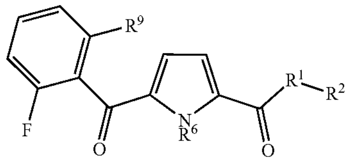

In several embodiments, $R^1$ is selected from the group consisting of —$CH_2$—, —$CHCH_2$-(optionally substituted with phenyl), —NH—, and a single bond. In several embodiments, $R^2$ is selected from the group consisting of optionally substituted $C_{6-10}$ aryl, optionally substituted 6 membered heteroaryl, and optionally substituted 6-10 membered heterocyclyl. In several embodiments, $R^6$ is selected from the group consisting of —H, $C_{1-6}$ alkyl, $C_{1-6}$ haloalkyl, and $C_{6-10}$ aryl. In several embodiments, $R^9$ is selected from the group consisting of —H, halogen, and nitro. In several embodiments, $R^1$ is —$CHCH_2R^{10}$ where $R^{10}$ is selected from the group consisting of:

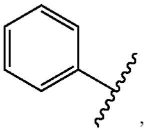 , 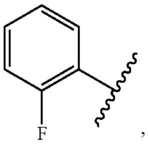 , 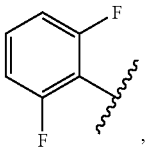 ,

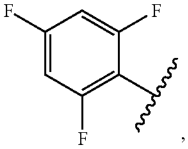 , 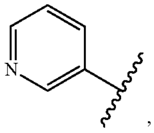 , 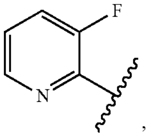 ,

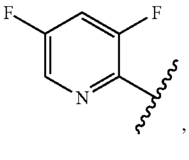 , 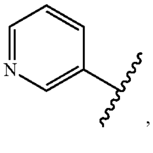 , 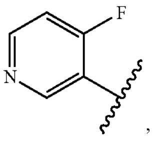 ,

-continued

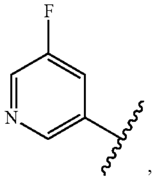 , 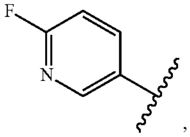 , 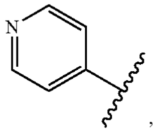 ,

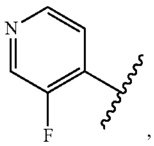 , and 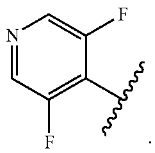 .

Any one of the directly preceding structures may be further optionally substituted by replacing one or more-H atoms of any carbon or nitrogen atom present within the structure. In several embodiments, $R^1$ is —$CH_2$—. In several embodiments, $R^2$ is selected from the group consisting of:

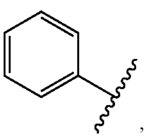 , 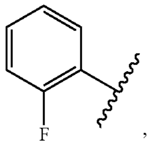 , 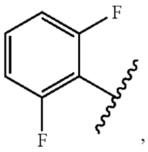 ,

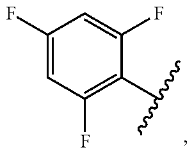 , 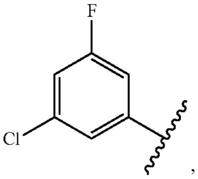 , 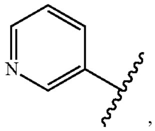 ,

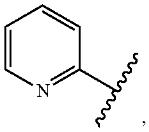 , 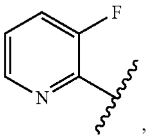 , 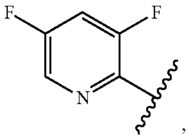 ,

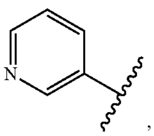 , 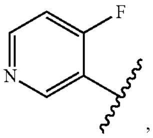 , 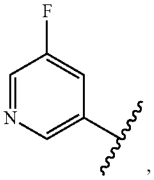 ,

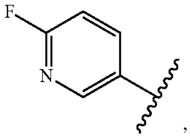 , 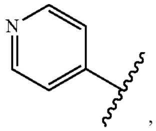 , 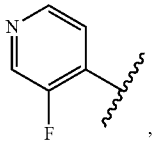 , and

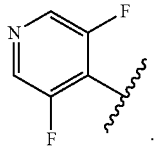 .

Any one of the directly preceding structures may be further optionally substituted by replacing one or more —H atoms of any carbon or nitrogen atom present within the structure. In several embodiments, $R^1$ is —NH— or a single bond. In several embodiments, $R^2$ is selected from the group consisting of:

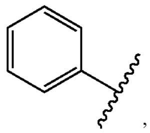, 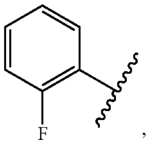, 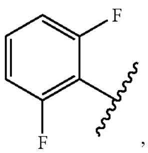,

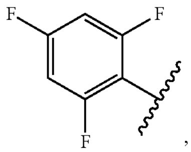, 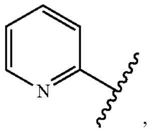, 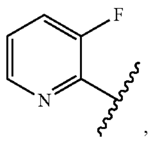,

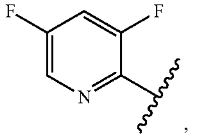, 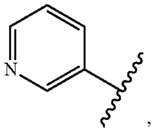, 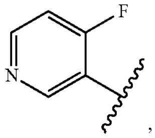,

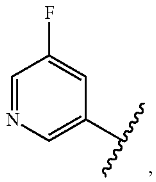, 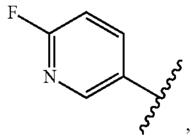, 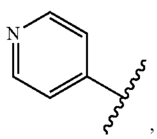,

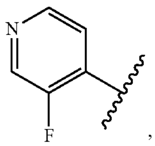, 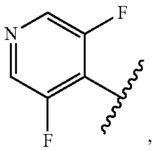, 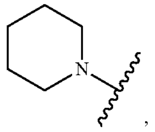,

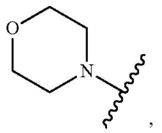, 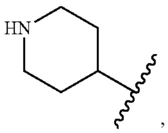, 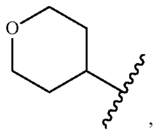,

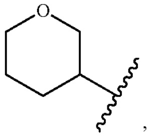, 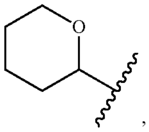, 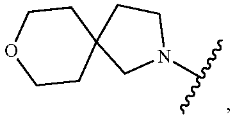,

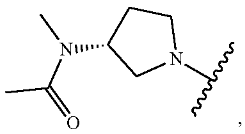, and 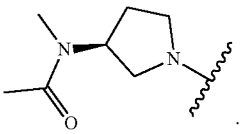.

Any one of the directly preceding structures may be further optionally substituted by replacing one or more-H atoms of any carbon or nitrogen atom present within the structure. In several embodiments, $R^6$ is $C_{1-6}$ alkyl. In several embodiments, $R^6$ is methyl. In several embodiments, $R^9$ is halogen. In several embodiments, $R^9$ is F.

Several embodiments are represented by Formula (Ia3), as disclosed elsewhere herein, where $R^1$ is —$CH_2$—, $R^9$ is —H, and each other variable of the structure of Formula (Ia3) is as defined elsewhere herein. In several embodiments, where $R^1$ is —$CH_2$—, $R^9$ is —H, and $R^2$ is selected from:

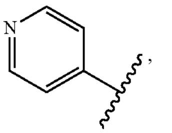, 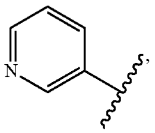, and 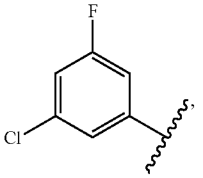,

Formula (Ia3) may be represented by any one of the following compounds (or others):

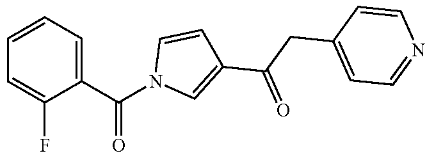

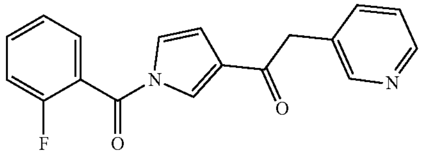

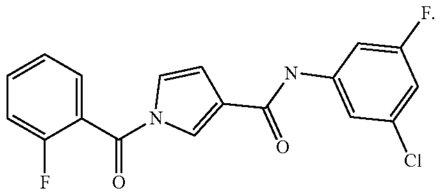.

Several embodiments are represented by Formula (Ia3), as disclosed elsewhere herein, where $R^1$ is a single bond, $R^9$ is —H, and each other variable of the structure of Formula (Ia3) is as defined elsewhere herein. In several embodiments, where $R^1$ is a single bond, $R^9$ is —H, and $R^2$ is selected from:

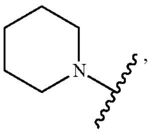, 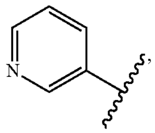,

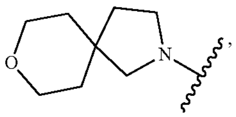, and 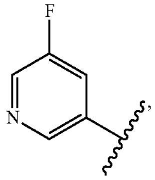,

Formula (Ia3) may be represented by any one of the following compounds (or others):

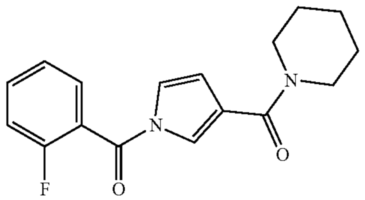

-continued

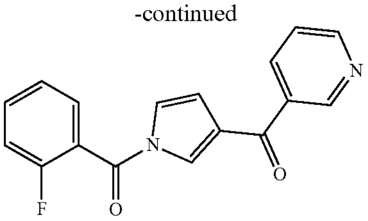

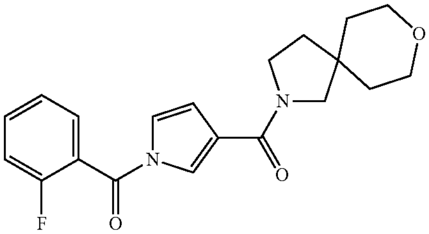

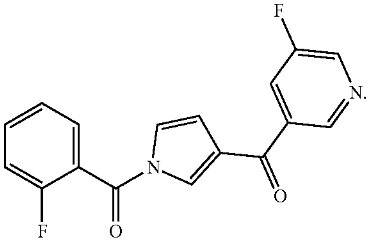

Several embodiments are represented by Formula (Ia3), as disclosed elsewhere herein, where $R^1$ is —NH—, $R^9$ is —H, and each other variable of the structure of Formula (Ia3) is as defined elsewhere herein. In several embodiments, where $R^1$ is —NH—, $R^9$ is —H, and $R^2$ is:

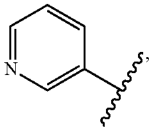

Formula (Ia3) may be represented by the following compound (or others):

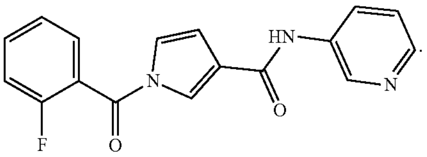 [SMILES: O=C(Nc1cccnc1)c1ccn(C(=O)c2ccccc2F)c1]

Several embodiments are represented by Formula (Ib3), as disclosed elsewhere herein, where $R^1$ is —$CH_2$—, $R^9$ is —H, and each other variable of the structure of Formula (Ib3) is as defined elsewhere herein. In several embodiments, where $R^1$ is —$CH_2$—, $R^9$ is —H, and $R^2$ is selected from:

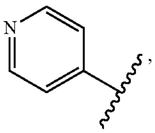, 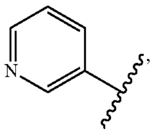, and 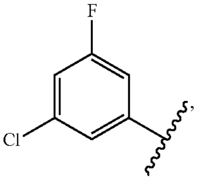

Formula (Ib3) may be represented by any one of the following compounds (or others):

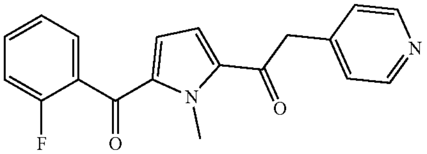

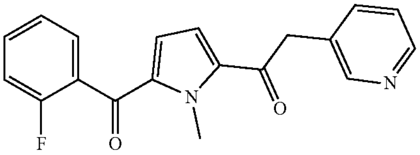

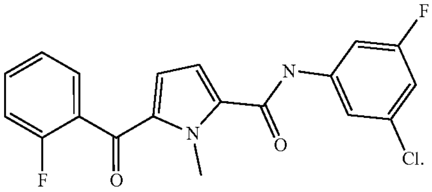

Several embodiments are represented by Formula (Ib3), as disclosed elsewhere herein, where $R^1$ is a single bond, $R^9$ is —H, and each other variable of the structure of Formula (Ib3) is as defined elsewhere herein. In several embodiments, where $R^1$ is a single bond, $R^9$ is —H, and $R^2$ is selected from:

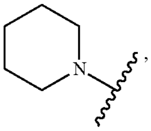, 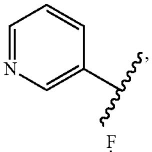

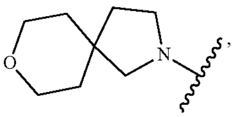, and 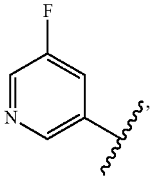

Formula (Ib3) may be represented by any one of the following compounds (or others):

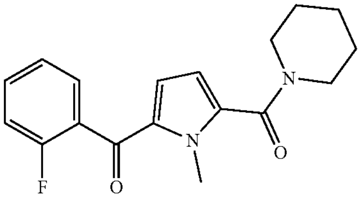

-continued

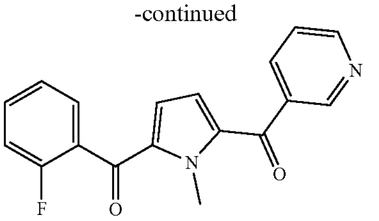

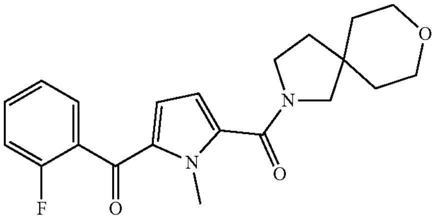

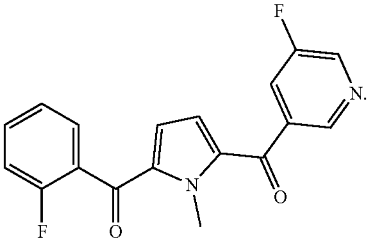

Several embodiments are represented by Formula (Ib3), as disclosed elsewhere herein, where $R^1$ is —NH—, $R^9$ is —H, and each other variable of the structure of Formula (Ib3) is as defined elsewhere herein. In several embodiments, where $R^1$ is —NH—, $R^9$ is —H, and $R^2$ is:

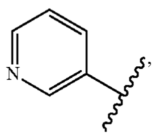

Formula (Ib3) may be represented by the following compound (or others):

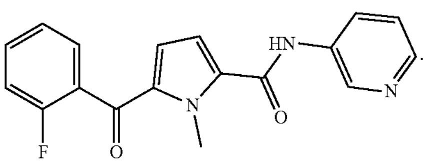 [SMILES: Cn1c(C(=O)Nc2cccnc2)ccc1C(=O)c1ccccc1F]

Formula (Ia4) & (Ib4) Compounds

Several exemplary embodiments of structures of Formula (I), where $R^3$ is $C_1$ alkylene and $R^4$ and $R^3$ taken together are:

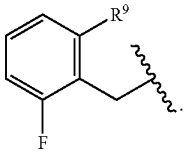

In several embodiments, Formula (I) may be represented by the structure of: Formula (Ia4), a 3-carboxy pyrrole, where V is N; each instance of W, X, and Z is $C(R^5)$ where $R^5$ is —H; and Y is C; or Formula (Ib4), a 5-carboxy pyrrole, where V is C; each instance of W and X is $C(R^5)$ where $R^5$ is —H; Y is C; and Z is $NR^6$ and each other variable is as defined elsewhere herein (e.g., as defined in Formula (I)):

(Ia4)

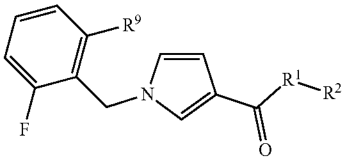

(Ib4)

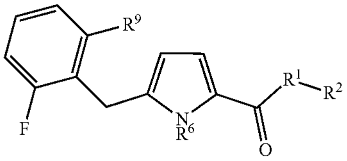

In several embodiments, R' is selected from the group consisting of —$CH_2$—, —$CHCH_2$ (optionally substituted phenyl), —NH—, and a single bond. In several embodiments, $R^2$ is selected from the group consisting of optionally substituted $C_{6-10}$ aryl, optionally substituted 6 membered heteroaryl, and optionally substituted 6-10 membered heterocyclyl. In several embodiments, $R^6$ is selected from the group consisting of —H, $C_{1-6}$ alkyl, $C_{1-6}$ haloalkyl, and $C_{6-10}$ aryl. In several embodiments, $R^9$ is selected from the group consisting of —H, halogen, and nitro. In several embodiments, $R^1$ is —$CHCH_2R^{10}$ where $R^{10}$ is selected from the group consisting of:

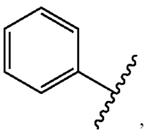 , 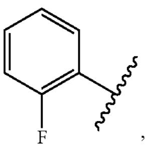 , 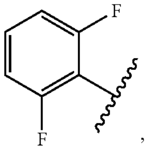 ,

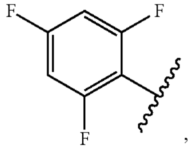 , 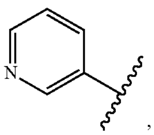 , 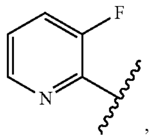 ,

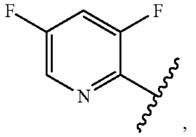 , 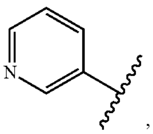 , 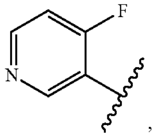 ,

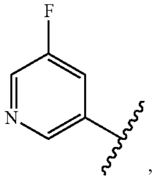 , 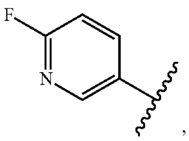 , 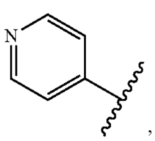 ,

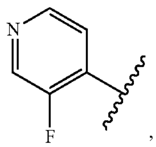 , and 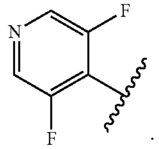 .

Any one of the directly preceding structures may be further optionally substituted by replacing one or more-H atoms of any carbon or nitrogen atom present within the structure. In several embodiments, $R^1$ is —$CH_2$—. In several embodiments, $R^2$ is selected from the group consisting of:

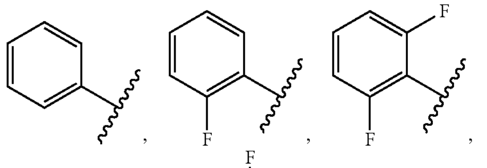
, , ,

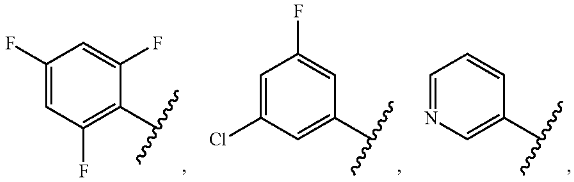
, , ,

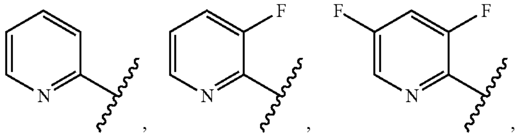
, , ,

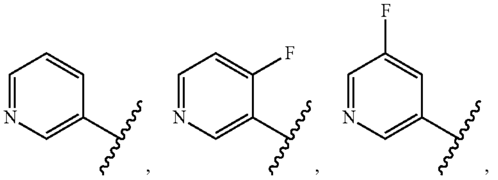
, , ,

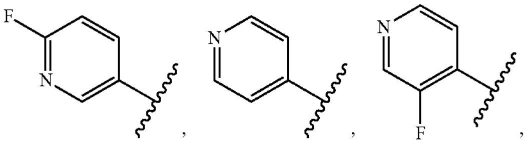
, , , and

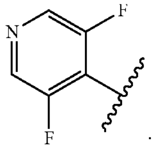
.

Any one of the directly preceding structures may be further optionally substituted by replacing one or more-H atoms of any carbon or nitrogen atom present within the structure. In several embodiments, $R^1$ is —NH— or a single bond. In several embodiments, $R^2$ is selected from the group consisting of:

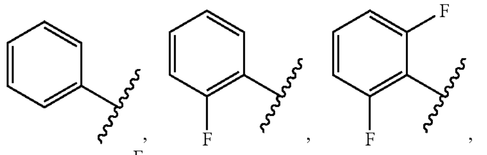
, , ,

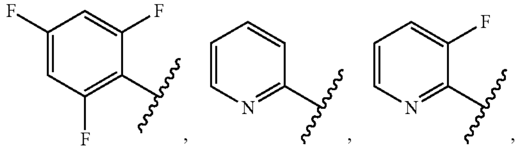
, , ,

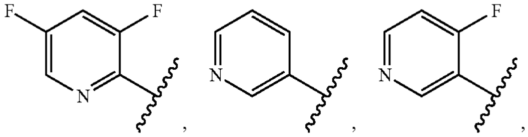
, , ,

-continued

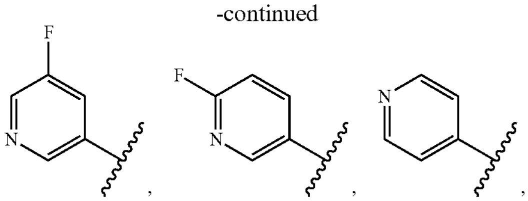
, , ,

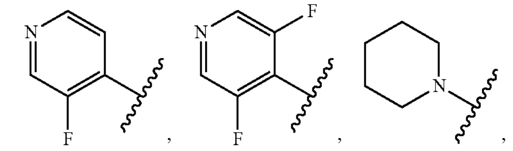
, , ,

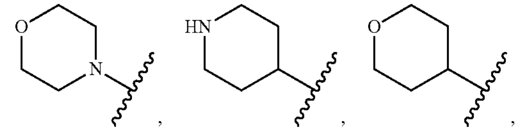
, , ,

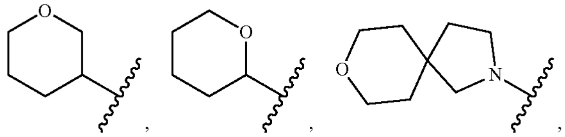
, , ,

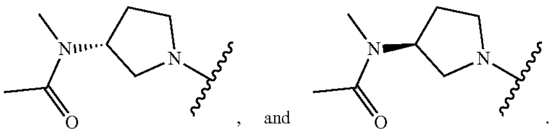
, and .

Any one of the directly preceding structures may be further optionally substituted by replacing one or more-H atoms of any carbon or nitrogen atom present within the structure. In several embodiments, $R^6$ is $C_{1-6}$ alkyl. In several embodiments, $R^6$ is methyl. In several embodiments, $R^9$ is halogen. In several embodiments, $R^9$ is F.

Several embodiments are represented by Formula (Ia4), as disclosed elsewhere herein, where $R^1$ is —NH—, $R^9$ is F, and each other variable of the structure of Formula (Ia4) is as defined elsewhere herein. In several embodiments, where $R^1$ is —NH—, $R^9$ is F, and $R^2$ is selected from:

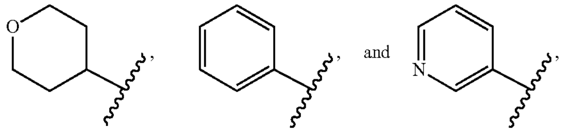 [SMILES: *C1CCOCC1 ; *c1ccccc1 ; *c1cccnc1]
, , and ,

Formula (Ia4) may be represented by any one of the following compounds (or others):

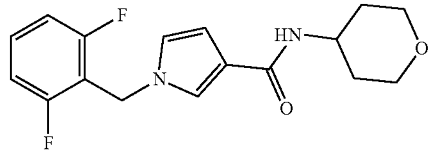

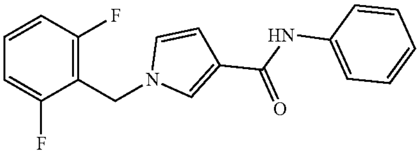

-continued

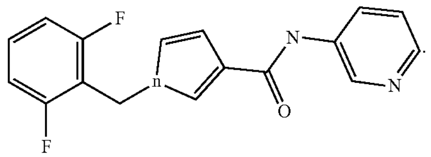

Several embodiments are represented by Formula (Ia4), as disclosed elsewhere herein, where $R^1$ is a single bond, $R^9$ is F, and each other variable of the structure of Formula (Ia4) is as defined elsewhere herein. In several embodiments, where $R^1$ is a single bond, $R^9$ is F, and $R^2$ is selected from:

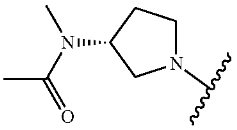
and
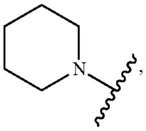
,

Formula (Ia4) may be represented by any one of the following compounds (or others):

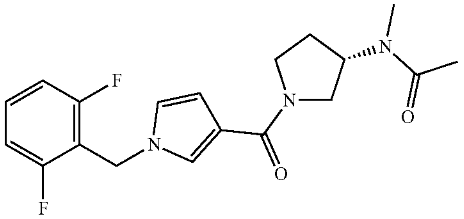

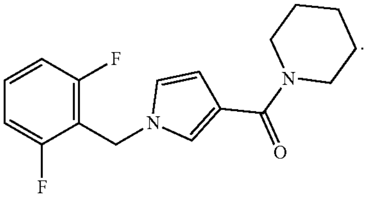

Several embodiments are represented by Formula (Ia4), as disclosed elsewhere herein, where $R^1$ is $CHCH_2R^{10}$, $R^2$ is $C_6$ aryl, $R^9$ is F, and each other variable of the structure of Formula (Ia4) is as defined elsewhere herein. In several embodiments, where $R^1$ is $CHCH_2R^{10}$, $R^2$ is $C_6$ aryl, $R^9$ is F, and $R^{10}$ is:

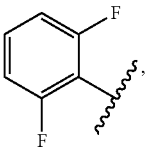
,

Formula (Ia4) may be represented by the following compound (or others):

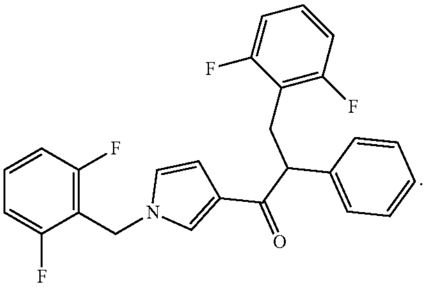 [SMILES: O=C(c1ccn(Cc2c(F)cccc2F)c1)C(Cc1c(F)cccc1F)c1ccccc1]

Several embodiments are represented by Formula (Ib4), as disclosed elsewhere herein, where $R^1$ is —NH—, $R^9$ is F, and each other variable of the structure of Formula (Ib4) is as defined elsewhere herein. In several embodiments, where $R^1$ is —NH—, $R^9$ is F, and $R^2$ is selected from:

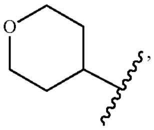
,
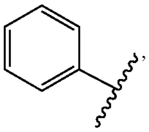
, and
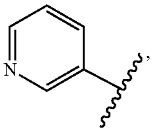
,

Formula (Ib4) may be represented by any one of the following compounds (or others):

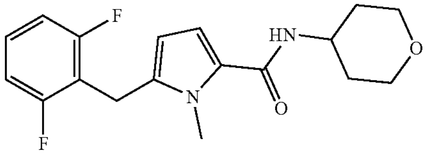

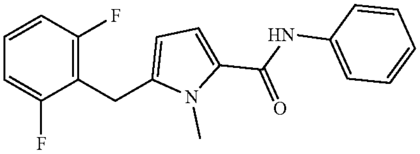

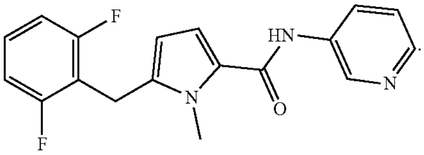

Several embodiments are represented by Formula (Ib4), as disclosed elsewhere herein, where $R^1$ is a single bond, $R^9$ is F, and each other variable of the structure of Formula (Ib4) is as defined elsewhere herein. In several embodiments, where $R^1$ is a single bond, $R^9$ is F, and $R^2$ is selected from:

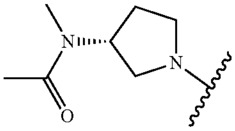
and
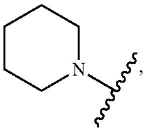
,

Formula (Ib4) may be represented by any one of the following compounds (or others):

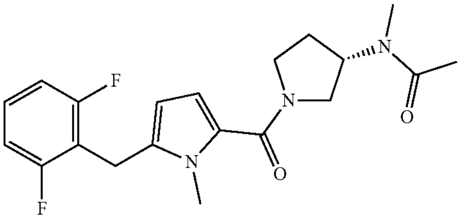

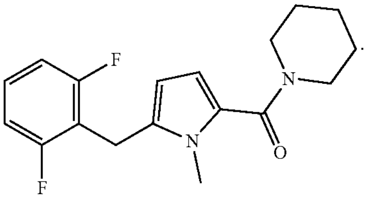

Several embodiments are represented by Formula (Ib4), as disclosed elsewhere herein, where $R^1$ is $CHCH_2R^{10}$, $R^2$ is $C_6$ aryl, $R^9$ is F, and each other variable of the structure of Formula (Ib4) is as defined elsewhere herein. In several embodiments, where $R^1$ is $CHCH_2R^{10}$, $R^2$ is $C_6$ aryl, $R^9$ is F, and $R^{10}$ is:

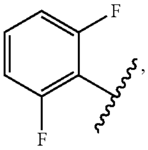 [SMILES: *c1c(F)cccc1F],

Formula (Ib4) may be represented by the following compound (or others):

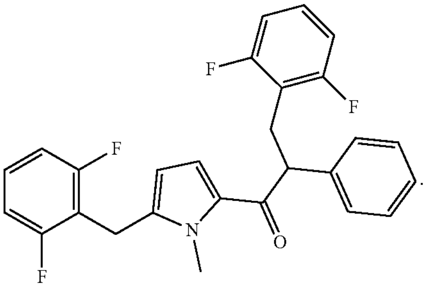 [SMILES: Cn1c(Cc2c(F)cccc2F)ccc1C(=O)C(Cc1c(F)cccc1F)c1ccccc1]

Formula (Ia5) & (Ib5) Compounds

Several exemplary embodiments of structures of Formula (I), where $R^3$ is —C(═O)—, $R^4$ is:

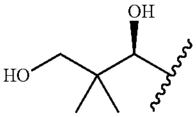,

In several embodiments, Formula (I) may be represented by the structure of: Formula (Ia4), a 3-carboxy pyrrole, where V is N; each instance of W, X, and Z is $C(R^5)$ where $R^5$ is —H; and Y is C; or Formula (Ib3), a 5-carboxy pyrrole, where V is C; each instance of W and X is $C(R^5)$ where $R^5$ is —H; Y is C; and Z is $NR^6$ and each other variable is as defined elsewhere herein (e.g., as defined in Formula (I)):

(Ia5)

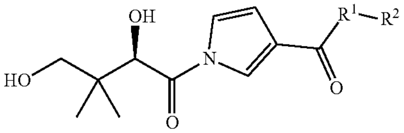

(Ib5)

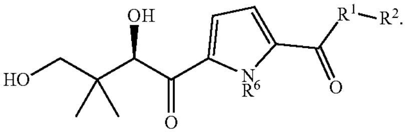

In several embodiments, $R^1$ is —$CH_2$— or a single bond. In several embodiments, $R^2$ is selected from the group consisting of optionally substituted $C_{6-10}$ aryl, optionally substituted 6 membered heteroaryl, and optionally substituted 6-10 membered heterocyclyl. In several embodiments, $R^6$ is selected from the group consisting of —H, $C_{1-6}$ alkyl, $C_{1-6}$ haloalkyl, and $C_{6-10}$ aryl. In several embodiments, $R^6$ is $C_{1-6}$ alkyl. In several embodiments, $R^6$ is methyl. In several embodiments, $R^2$ is selected from the group consisting of:

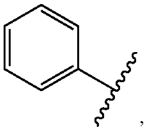, 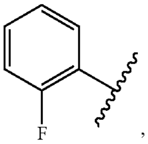, 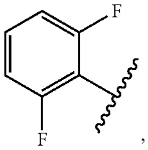,
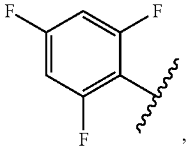, 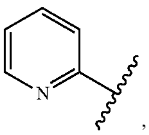, 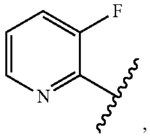,
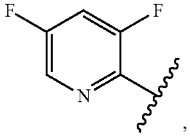, 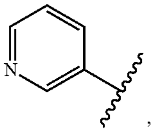, 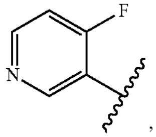,
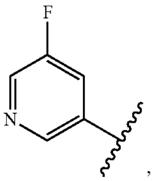, 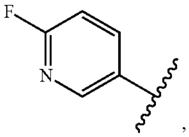, 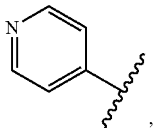,
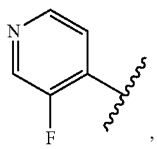, 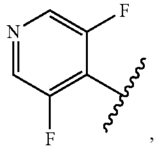, 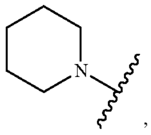,
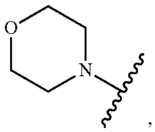, 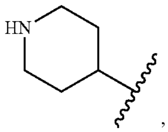, 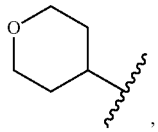, -continued

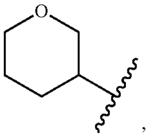

,

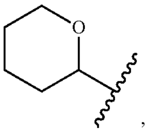

, and

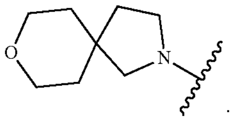

.

Any one of the directly preceding structures may be further optionally substituted by replacing one or more-H atoms of any carbon or nitrogen atom present within the structure.

Several embodiments are represented by Formula (Ia5), as disclosed elsewhere herein, where $R^1$ is a single bond, and each other variable of the structure of Formula (Ia5) is as defined elsewhere herein. In several embodiments, where $R^1$ is a single bond and $R^2$ is selected from:

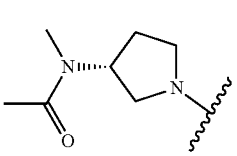

and

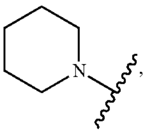

,

Formula (Ia5) may be represented by any one of the following compounds (or others):

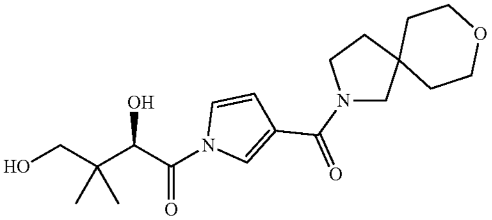

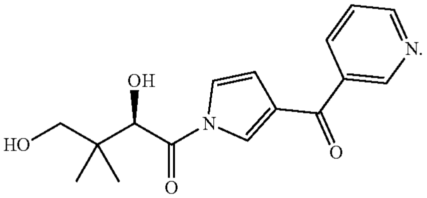

.

Several embodiments are represented by Formula (Ib5), as disclosed elsewhere herein, where $R^1$ is a single bond, and each other variable of the structure of Formula (Ib5) is as defined elsewhere herein. In several embodiments, where $R^1$ is a single bond and $R^2$ is selected from:

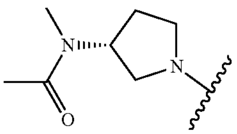

and

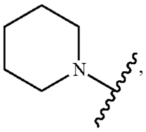

,

Formula (Ib5) may be represented by any one of the following compounds (or others):

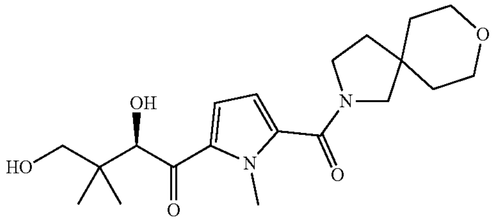

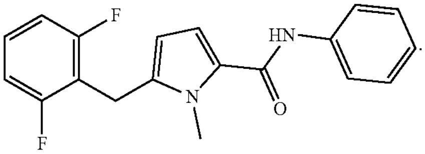

.

Several exemplary embodiments of structures of Formula (I) may be represented by the structure of Formula (Ia5), a 3-carboxy pyrrole, Formula (Ia6), a 3-carboxy pyrrole, Formula (Ia7), a 3-carboxy pyrrole, or Formula (Ib5), a 2-carboxy; where each other variable is as defined elsewhere herein (e.g., as defined in Formula (I)):

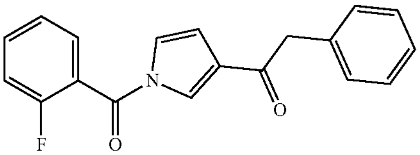 [SMILES: O=C(Cc1ccccc1)c1ccn(C(=O)c2ccccc2F)c1]

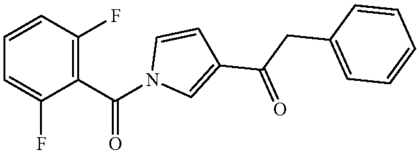

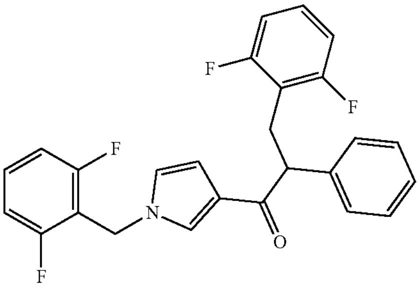

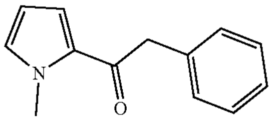

.

Other Embodiments of Formula (I)

In several embodiments, the compound with the structure of Formula (I) does not comprise one or more groups selected from any one of Formulae IIa, IIb, or IIc:

IIa

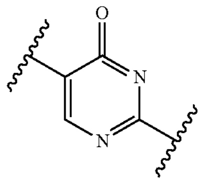

IIb

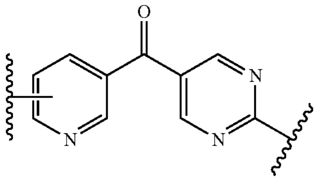

IIc

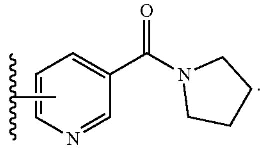

Methods of Making Compounds of Formula I

The compounds disclosed herein may be synthesized by methods described below, or by modification of these methods. Ways of modifying the methodology include, among others, temperature, solvent, reagents etc., known to those skilled in the art. In general, during any of the processes for preparation of the compounds disclosed herein, it may be necessary and/or desirable to protect sensitive or reactive groups on any of the molecules concerned. This may be achieved by means of conventional protecting groups, such as those described in *Protective Groups in Organic Chemistry* (ed. J. F. W. McOmie, Plenum Press, 1973); and P. G. M. Green, T. W. Wutts, *Protecting Groups in Organic Synthesis* (3rd ed.) Wiley, New York (1999), which are both hereby incorporated herein by reference in their entirety. The protecting groups may be removed at a convenient subsequent stage using methods known from the art. Synthetic chemistry transformations useful in synthesizing applicable compounds are known in the art and include e.g. those described in R. Larock, *Comprehensive Organic Transformations*, VCH Publishers, 1989, or L. Paquette, ed., *Encyclopedia of Reagents for Organic Synthesis*, John Wiley and Sons, 1995, which are both hereby incorporated herein by reference in their entirety. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

In the following schemes, protecting groups are selected for their compatibility with the requisite synthetic steps as well as compatibility of the introduction and deprotection steps with the overall synthetic schemes (P. G. M. Green, T. W. Wutts, Protecting Groups in Organic Synthesis (3rd ed.) Wiley, New York (1999)).

If the compounds of the present technology contain one or more chiral centers, such compounds can be prepared or isolated as pure stereoisomers, i.e., as individual enantiomers or d(l) stereoisomers, or as stereoisomer-enriched mixtures. All such stereoisomers (and enriched mixtures) are included within the scope of the present technology, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wisconsin, USA), Bachem (Torrance, California, USA), Emka-Chemce or Sigma (St. Louis, Missouri, USA). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

Several exemplary embodiments pertain to methods of synthesizing compounds of Formula (I) (e.g., Compound 1, Compound 2, etc.) and intermediates of compounds of Formula (I). In several embodiments, to prepare a compound of Formula (I) a protected pyrrole (S1) is prepared and/or acquired, as shown below:

S1

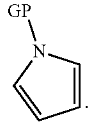

In several embodiments, S1 comprises a protecting group (PG) on the 1 position nitrogen. In several embodiments, the amine protecting group PG is a silyl protecting group. In several embodiments, the silyl protecting group is trimethylsilyl (TMS), tert-butyldiphenylsilyl (TBDPS), tert-butyldimethylsilyl (TBS/TBDMS) or triisopropylsilyl (TIPS).

Figure 1B:
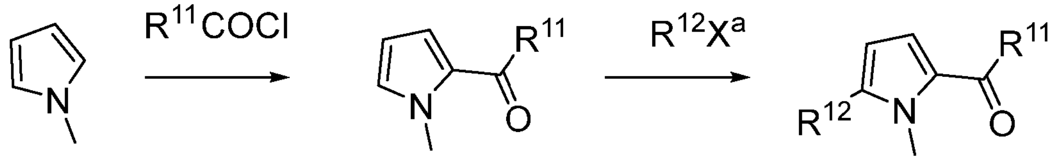
FIG. 1B provides a reaction pathway for the preparation of several embodiments of compounds of Formula (I).

In several embodiments, to prepare a structure of Formula (Ia1), a regioselective two-regioselective alkylation of protected pyrrole scaffolds is performed as depicted in the general scheme as shown in FIG. 1A. In several embodiments, PG is a protecting group. In several embodiments, $R^{11}$ or $R^{12}$ may be the same as $R^1$, $R^2$, $R^3$, $R^4$, or $R^6$. In several embodiments, $X^a$ is a halogen. Alternatively, in several embodiments, to prepare a structure of Formula (Ib1), a regioselective two-regioselective alkylation of 1-methyl pyrrole scaffolds is performed as depicted in the general scheme as shown in FIG. 1B.

Several embodiments pertain to intermediate compounds and methods of manufacture of compound of Formula (I) that proceed through steps involving intermediates. In several embodiments, the intermediates are selected from the group consisting of:

Compound 80

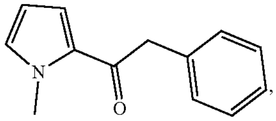,

Compound 82

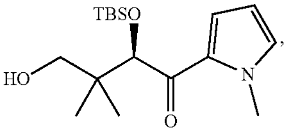,

Compound 83

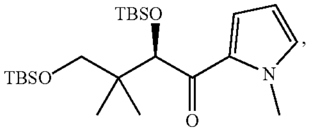,

Compound 84

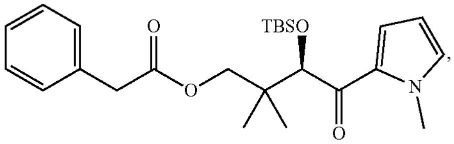,

Compound 85

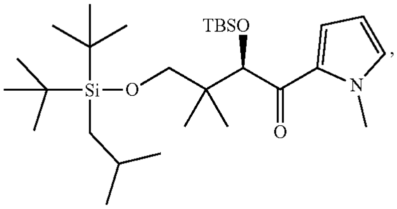, and

Compound 87

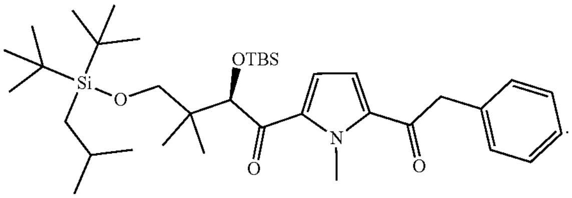.

Administration and Pharmaceutical Compositions

The compounds are administered at a therapeutically effective dosage. While human dosage levels have yet to be optimized for the compounds described herein, generally, a daily dose may be from about 0.25 mg/kg to about 120 mg/kg or more of body weight, from about 0.5 mg/kg or less to about 70 mg/kg, from about 1.0 mg/kg to about 50 mg/kg of body weight, or from about 1.5 mg/kg to about 10 mg/kg of body weight. Thus, for administration to a 70 kg person, the dosage range would be from about 17 mg per day to about 8000 mg per day, from about 35 mg per day or less to about 7000 mg per day or more, from about 70 mg per day to about 6000 mg per day, from about 100 mg per day to about 5000 mg per day, or from about 200 mg to about 3000 mg per day. The amount of active compound administered will, of course, be dependent on the subject and disease state being treated, the severity of the affliction, the manner and schedule of administration and the judgment of the prescribing physician.

Administration of the compounds disclosed herein or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarilly, vaginally, rectally, or intraocularly. Oral and parenteral administrations are customary in treating the indications that are the subject of the preferred embodiments.

The compounds useful as described above can be formulated into pharmaceutical compositions for use in treatment of these conditions. Standard pharmaceutical formulation techniques are used, such as those disclosed in Remington's The Science and Practice of Pharmacy, 21st Ed., Lippincott Williams & Wilkins (2005), incorporated by reference in its entirety. Accordingly, some embodiments include pharmaceutical compositions comprising: (a) a safe and therapeutically effective amount of a compound described herein (including enantiomers, diastereoisomers, tautomers, polymorphs, and solvates thereof), or pharmaceutically acceptable salts thereof; and (b) a pharmaceutically acceptable carrier, diluent, excipient or combination thereof.

In addition to the selected compound useful as described above, some embodiments include compositions containing a pharmaceutically-acceptable carrier. The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of *theobroma*; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

The compositions described herein are preferably provided in unit dosage form. As used herein, a "unit dosage form" is a composition containing an amount of a compound that is suitable for administration to an animal, preferably mammal subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, though a single administration is not specifically excluded. The skilled artisan will recognize that the formulation does not specifically contemplate the entire course of therapy and such decisions are left for those skilled in the art of treatment rather than formulation.

The compositions useful as described above may be in any of a variety of suitable forms for a variety of routes for administration, for example, for oral, nasal, rectal, topical (including transdermal), ocular, intracerebral, intracranial, intrathecal, intra-arterial, intravenous, intramuscular, subcutaneous, or other parental routes of administration. In some embodiments, the compositions may be in a form suitable for subcutaneous administration. The skilled artisan will appreciate that oral and nasal compositions comprise compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropics, surface-active agents, and encapsulating substances. Optional pharmaceutically-active materials may be included, which do not substantially interfere with the inhibitory activity of the compound. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules, granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions described herein may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

For topical use, creams, ointments, gels, solutions or suspensions, etc., containing the compound disclosed herein are employed. Topical formulations may generally be comprised of a pharmaceutical carrier, co-solvent, emulsifier, penetration enhancer, preservative system, and emollient.

For intravenous administration, the compounds and compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, *PDA J Pharm Sci and Tech* 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The compositions for intravenous administration may be provided to caregivers in the form of one more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

The actual dose of the active compounds described herein depends on the specific compound, and on the condition to be treated; the selection of the appropriate dose is well within the knowledge of the skilled artisan.

The compounds and compositions described herein, if desired, may be presented in a pack or dispenser device containing one or more unit dosage forms containing the active ingredient. Such a pack or device may, for example, comprise metal or plastic foil, such as a blister pack, or glass, and rubber stoppers such as in vials. The pack or dispenser device may be accompanied by instructions for administration. Compounds and compositions described herein are formulated in a compatible pharmaceutical carrier may also be prepared, placed in an appropriate container, and labeled for treatment of an indicated condition.

The amount of the compound in a formulation can vary within the full range employed by those skilled in the art. Typically, the formulation will contain, on a weight percent (wt %) basis, from about 0.01 99.99 wt % of a compound of the present technology based on the total formulation, with the balance being one or more suitable pharmaceutical excipients. Preferably, the compound is present at a level of about 1 80 wt %. Representative pharmaceutical formulations are described below.

Formulation Examples

The following are representative pharmaceutical formulations containing a compound of Formula I.

Formulation Example 1—Tablet Formulation

The following ingredients are mixed intimately and pressed into single scored tablets.

TABLE 0.1

| Ingredient | Quantity per tablet, mg |
|---|---|
| Compounds disclosed herein | 400 |
| cornstarch | 50 |
| croscarmellose sodium | 25 |
| lactose | 120 |
| magnesium stearate | 5 |

Formulation Example 2—Capsule Formulation

The following ingredients are mixed intimately and loaded into a hard-shell gelatin capsule.

| Ingredient | Quantity per capsule, mg |
|---|---|
| Compounds disclosed herein | 200 |
| lactose, spray-dried | 148 |
| magnesium stearate | 2 |

Formulation Example 3—Suspension Formulation

The following ingredients are mixed to form a suspension for oral administration.

| Ingredient | Amount |
|---|---|
| Compounds disclosed herein | 1.0 g |
| fumaric acid | 0.5 g |
| sodium chloride | 2.0 g |
| methyl paraben | 0.15 g |
| propyl paraben | 0.05 g |
| granulated sugar | 25.0 g |
| sorbitol (70% solution) | 13.00 g |
| Veegum K (Vanderbilt Co.) | 1.0 g |
| flavoring | 0.035 mL |
| colorings | 0.5 mL |
| distilled water | q.s. to 100 mL |

Formulation Example 4—Injectable Formulation

The following ingredients are mixed to form an injectable formulation.

| Ingredient | Amount |
|---|---|
| Compounds disclosed herein | 0.2 mg-20 mg |
| sodium acetate buffer solution, 0.4M | 2.0 mL |
| HCl (1N) or NaOH (1N) | q.s. to suitable pH |
| water (distilled, sterile) | q.s. to 20 mL |

Formulation Example 5—Suppository Formulation

A suppository of total weight 2.5 g is prepared by mixing the compound of the present technology with Witepsol® H-15 (triglycerides of saturated vegetable fatty acid; Riches-Nelson, Inc., New York), and has the following composition:

| Ingredient | Amount |
|---|---|
| Compounds disclosed herein | 500 mg |
| Witepsol ® H-15 | balance |

Methods of Treatment

The compounds of Formula I disclosed herein or their tautomers and/or pharmaceutically acceptable salts thereof can effectively act as inhibitors of the enzymatic activity of vanin enzymes (e.g., vanin 1). Some embodiments provide pharmaceutical compositions comprising one or more compounds disclosed herein and a pharmaceutically acceptable excipient.

Some embodiments provide a method of preventing, treating, or ameliorating one or more inflammatory or autoimmune diseases in a subject. In some embodiments, the method includes administering one or more of the compounds disclosed herein to a subject in need thereof. In some embodiments, the method includes administering a pharmaceutically acceptable salt thereof of one or more of the compounds disclosed herein to a subject in need thereof.

In several embodiments, the disclosed compound is used to prevent, treat, or ameliorate ulcerative colitis, Crohn's disease, rheumatoid arthritis, atopic dermatitis, psoriasis, lupus (e.g., systemic erythematosus lupus), atherosclerosis, and Type 1 diabetes. Some embodiments provide a method preventing, treating, or ameliorating Lupus, rheumatoid arthritis, atopic dermatitis, and psoriasis. In some embodiments, the method includes administering one or more of the compounds disclosed herein to a subject in need thereof. In some embodiments, the method includes administering a pharmaceutically acceptable salt thereof of one or more of the compounds disclosed herein to a subject in need thereof.

In several embodiments, the disclosed compound is used to treat a cancer. In some embodiments, the cancer is selected from the group consisting of colon cancer, liver cancer, pancreatic cancer, gastric cancer, esophageal cancer, prostate cancer, breast cancer, cholangiocarcinomas, sarcomas, or acute myeloid leukemia. In some embodiments, the method includes administering one or more of the compounds disclosed herein to a subject in need thereof. In some embodiments, the method includes administering a pharmaceutically acceptable salt thereof of one or more of the compounds disclosed herein to a subject in need thereof.

In some embodiments, the method of administering one or more of the compounds disclosed herein results in the prevention, treatment, or amelioration, of an inflammatory or autoimmune disease. In some embodiments, the method of administering one or more of the compounds disclosed herein results in the prevention, treatment, or amelioration, of ulcerative colitis, Crohn's disease, atopic dermatitis, psoriasis, systemic erythematosus lupus, atherosclerosis, and Type 1 diabetes. In some embodiments, the method includes administering a pharmaceutically acceptable salt thereof of one or more of the compounds disclosed herein.

In some embodiments, the method of administering one or more of the compounds disclosed herein results in the inhibition of the activity of vanin 1 in one or more organs of said subject. In several embodiments, inhibiting the activity of vanin 1 suppresses the expression and/or activity of pro-inflammatory signals. In several embodiments, the pro-inflammatory signals may one or more cytokines. In several embodiments, the cytokine includes TNF-alpha (TNFA), interleukin 6 (IL6), interleukin 1beta (IL1B), MCP1 and interleukin 8 (IL8). In some embodiments, the method includes administering a pharmaceutically acceptable salt thereof of one or more of the compounds disclosed herein.

Some embodiments include co-administering a compound, composition, and/or pharmaceutical composition described herein, with an additional medicament. By "co-administration," it is meant that the two or more agents may be found in the patient's bloodstream at the same time, regardless of when or how they are actually administered. In one embodiment, the agents are administered simultaneously. In one such embodiment, administration in combination is accomplished by combining the agents in a single dosage form. In another embodiment, the agents are administered sequentially. In one embodiment the agents are administered through the same route, such as orally. In another embodiment, the agents are administered through different routes, such as one being administered subcutaneously, another being administered orally and another being administered i.v.

The following examples are given for the purpose of illustrating various embodiments of the disclosure and are not meant to limit the present disclosure in any fashion. One skilled in the art will appreciate readily that the present disclosure is well adapted to carry out the objects and obtain the ends and advantages mentioned, as well as those objects, ends and advantages inherent herein. Changes therein and other uses which are encompassed within the spirit of the disclosure as defined by the scope of the claims will occur to those skilled in the art.

EXAMPLES

Example 1: Synthesis of Carboxy Pyrroles

All reactions were carried out under an atmosphere of argon. Reagents and solvents were used from commercial sources without additional purification. Hydrogenation reactions were run under a balloon. Microwave reactions were performed using a CEM Discover SP microwave synthesizer. Sample purification was conducted on a Buchi Pureflash with ELSD purification system using pre-packed commercially available silica gel columns. Thin layer chromatography (TLC) was performed on aluminum plates using Merck Kiesegel 60 F254 (230-400 mesh) fluorescent treated silica which were visualized under ultraviolet light (254 nm), or by staining with potassium permanganate or ninhydrin solution as appropriate. All Nuclear Magnetic Resonance (NMR) spectra were acquired on a Bruker Avance III HD 400 MHZ NMR spectrometer; chemical shifts are reported in ppm (δ). HPLC/MS was performed on a Sciex 5500 Qtrap mass spectrometry coupled with Shidmazu Nexera X2 UHPLC using Phenomenex Luna $C_{18}$ column (50×2.0 mm, 3 μm particle size) via following method: The gradient mobile phase A contains 0.1% formic acid in water and mobile phase B contains 0.1% formic acid in acetonitrile; A/B (95:5) from 0 to 0.9 minutes; to A/B (5:95) from 0.9 to 2.2 minutes; A/B (5:95) from 2.2 to 4.14 minutes; to A/B (95:5) from 4.14 to 4.20 minutes; A/B (95:5) from 4.2 to 6 minutes. The flow rate was 0.4 mL/min and the column temperature maintained at 35° C. and autosampler temperature at 4° C. Ion spray voltage, drying gas temperature, ion source gas 1, and ion source gas 2 settings were 4500V, 500° C., 35V, and 45V with ESI set in positive mode using full scan. All compounds purity was analyzed on Agilent 1260 Infinity II Lab LC Series HPLC (1260 Quantum, 1260 vial autosampler, ICC column oven, 1260 DAD WR detector). Samples were injected into Phenomenex Synergi Polar RP column (150×4.6 mm, 4 μm, 80 Å). The gradient mobile phase (A: water with 0.1% trifluoroacetic acid, B: acetonitrile with 0.1% trifluoroacetic acid; A/B (99:1) from 0 minute; to A/B (1:99) from 0 to 15 minutes; A/B (1:99) from 15 to 18 minutes; A/B (99:1) from 18 to 18.1 minutes; A/B (99:1) from 18.1 to 20 minutes) pumped at a flow rate of 1 mL/min. UV detector was set to 254 nm with column oven at 35° C. Injection volume was 10 μL, unless otherwise specified. All compounds that were evaluated in biological assay had ≥90% and animal study had ≥95% purity.

Figure 2A:
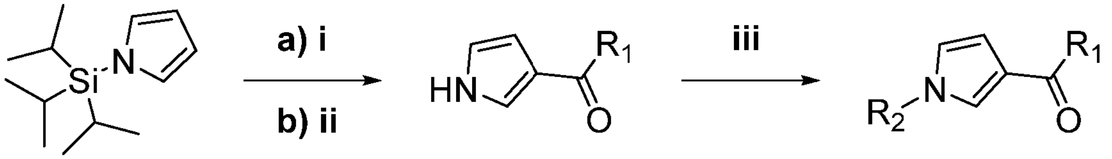
FIG. 2A provides a reaction pathway for the preparation of several embodiments of compounds of Formula (I).

The compounds were prepared in general by a regioselective two-regioselective alkylation of pyrrole scaffolds as depicted in the general scheme as shown in FIG. 2A. Conditions: (i) $AlCl_3$, $R_1$—COCl, THF, −78° C.-R.T.; nBuLi, $R_1$—N═C═O, THF (ii) TBAF, THF (iii) NaH, $R_2$—COCl or $R_2$—Cl, DMF; nBuLi, $R_1$—N═C═O, THF.

To investigate the pyrrolyl-carboxyl core toward the inhibiting activity of VNN1, 1,3-substituted (1H-pyrrol-3-yl)-one and (1H-pyrrol-3-yl)-carbamide analogues were synthesized from commercially 1-(triisopropylsilyl)-1H-pyrrole. An example of the structure activity relationship (SAR) of 1,3-substituted of these analogs derived respectively from various acylchloride or isocyanate with assist from computation effort to understand their role toward the target to further improve the potency.

Figure 2B:
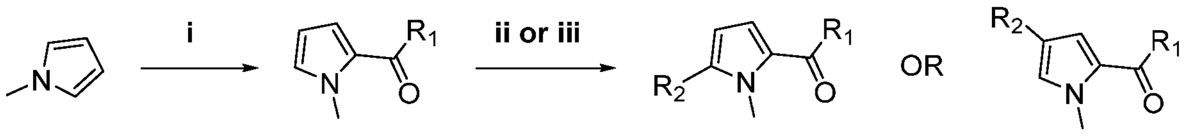
FIG. 2B provides a reaction pathway for the preparation of several embodiments of compounds of Formula (I).

To investigate the 2,5-substituted of 1-methylpyrrole in comparison to above general structure. 2,5-substituted versions (1-methylpyrrol-3-)-carboxyl were synthesized by also two alkylation of commercially available 1-methylpyrrole. Therefore, SAR of 2,5-substitution analogues for comparison as shown in FIG. 2B was tested. The reaction conditions were as follows: Conditions: (i) $AlCl_3$, $R_1$—COCl, DCE, R.T.; nBuLi, $R_1$—COCl, THF, −78° C.-R.T.; $R_1$—N═C═O, THF (ii) $Zn(OTf)_2$ or ZnO $R_2$—COCl or $R_2$—Cl, 50° C., DCE or $CH_3NO_2$.; nBuLi, $R_2$—Cl, THF, −78° C.-R.T.; nBuLi, $R_1$—N═C—O, THF.

All claimed structures disclosed herein were analyzed by computational molecular docking using the available software SeeSAR v.10. The published crystal structure data of a known Vanin-1 inhibitor bounded to Vanin-1 protein (4CYG-RR6) was acquired from The Protein Data Bank (rcsb.org/) and affinity binding for each compound was estimated. Data produced using the Vanin-1 protein was used to prepare compounds with good affinity to the Vanin-1 protein binding pocket. Each of those compounds is disclosed herein.

The below provide representative methods for preparing the compounds disclosed herein. In view of this guidance and the guidance provided by the remained of this disclosure, those skilled in the art will be able to prepare each structure disclosed herein.

Example 2: Synthesis of 1-(1-(2-fluorobenzoyl)-1H-pyrrol-3-yl)-2-phenylethan-1-one (Compound 1)

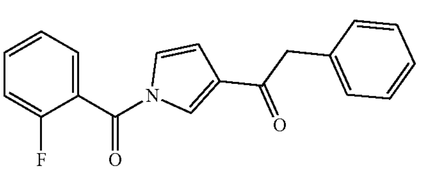

To a solution of commercially available 2-phenyl-(1H-pyrrol-3-yl) ethan-1-one (0.20 g, 1.08 mmol) in anhydrous DMF (6 mL) cooled with ice-bath under argon atmosphere was added 60% sodium hydride (0.05 g, 1.30 mmol) and stirred for 10 minutes. The ice-bath was removed and equilibrate to room temperature while stirring for additional 20 minutes until no observable bubbles. The mixture was then cooled again to 0° C. prior to slowly added 2-fluorobenzoyl chloride (0.21 g, 1.30 mmol) via syringe over 5 min and stirred for 30 min. The reaction mixtures were equilibrated to room temperature and stirred for 3 hours. Upon completion, the reaction was quenched with water (20 mL) and extracted with ethyl acetate (3×50 mL) and washed with sat. $NaHCO_3$ followed with brine. The combined organic layers were dried over anhydrous $Na_2SO_4$ and concentrated in vacuo. The residue was purified by Buchi Pureflash chromatography over silica gel cartridge (40 g) with 8:2 hexanes/ethyl acetate to give 1-(1-(2-fluorobenzoyl)-1H-pyrrol-3-yl)-2-phenylethan-1-one, Compound 1 (0.18 g, 54%) dried under vacuum as a yellow solid. 1H NMR (400 MHz, DMSO-d): δ 8.16 (m, 1H), 7.80-7.70 (m, 2H), 7.53-7.40 (m, 2H), 7.35-7.20 (m, 6H), 6.73 (dd, 1H, J=8.0, 4.0 Hz), 4.17 (s, 2H). MS (ESI): Calcd. for $C_{19}H_{14}FNO_2$: 307, found 308 $(M+H)^+$ Example 3: Synthesis of 1-(1-(2,6-difluorobenzyl)-1H-pyrrol-3-yl)-2-phenylethan-1-one (Compound 2) & 1-(1-(2,6-difluorobenzyl)-1H-pyrrol-3-yl)-3-(2,6-difluorophenyl)-2-phenylpropan-1-one (Compound 3)

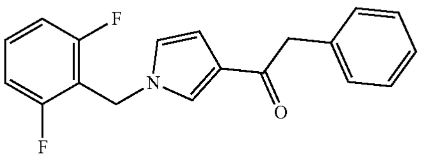

+

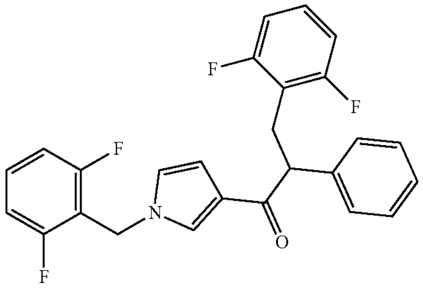

To a solution of commercially available 2-phenyl-(1H-pyrrol-3-yl) ethan-1-one (0.20 g, 1.08 mmol) in anhydrous DMF (6 mL) cooled with ice-bath under argon atmosphere was added 60% sodium hydride (0.06 g, 1.40 mmol) and stirred for 10 minutes. The ice-bath was removed and equilibrate to room temperature while stirring for additional 20 minutes until no observable bubbles. The mixture was then cooled again to 0° C. prior to slowly added 2,6-difluorobenzyl chloride (0.26 g, 1.62 mmol) via syringe over 5 min and stirred for 30 min. The reaction mixtures were equilibrated to room temperature and stirred for 3 hours. Upon completion, the reaction was quenched with water (20 mL) and extracted with ethyl acetate (3×50 mL) and washed with sat. $NaHCO_3$ followed with brine. The combined organic layers were dried over anhydrous $Na_2SO_4$ and concentrated in vacuo. The residue was purified by Buchi Pureflash chromatography over silica gel cartridge (40 g) with 8:2 hexanes/ethyl acetate to give a mixture of 1-(1-(2,6-difluorobenzyl)-1H-pyrrol-3-yl)-2-phenylethan-1-one, Compound 2 (0.10 g, 31%) as a yellow solid and 1-(1-(2,6-difluorobenzyl)-1H-pyrrol-3-yl)-3-(2,6-difluorophenyl)-2-phenylpropan-1-one, Compound 3 (0.22 g, 46%) as light yellow solid. Compound 2: 1H NMR (400 MHz, DMSO-d): δ 7.69 (t, 1H, J=4.0 Hz), 7.50 (tt, 1H, J=12.0, 8.0 Hz), 7.30-7.15 (m, 7H)6.81 (t, 1H, J=8.0 Hz), 6.49 (dd, 1H, J=8.0, 4.0 Hz), 5.24 (s, 2H), 3.99 (s, 2H). MS (ESI): Calcd.

for $C_{19}H_{15}F_2NO$: 311, found 312 $(M+H)^+$. Compound 3: 1H NMR (400 MHZ, DMSO-d): δ 7.60 (t, 1H, J=2.0 Hz), 7.46 ($d_f$-t, 1H, J=8.0, 32 Hz), 7.27-7.13 (m, 8H), 6.91 ($d_f$-t, 2H, J=8.0, 20 Hz), 6.70 (t, 1H, J=4.0 Hz), 6.42 (dd, 1H, J=4.0, 2.0 Hz), 5.17 (s, 2H), 4.59 (dd, 1H, J=8.0, 2.0 Hz), 3.24 (dd, 1H, J=12.0, 8.0 Hz), 3.14 (dd, 1H, J=12.0, 8.0 Hz). MS (ESI): Calcd. for $C_{26}H_{19}F_4NO$: 437, found 438 $(M+H)^+$ Example 4: Synthesis of Structure 1-(1-methyl-1H-pyrrol-2-yl)-2-phenylethan-1-one (Compound 80)

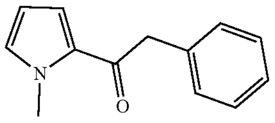

To a solution of commercially available 1-methylpyrrole (0.50 g, 6.16 mmol) in anhydrous dichloromethane (6 mL) under argon atmosphere was added phenlacetyl chloride (1.00 g, 6.47 mmol) and zinc trifluoromethanesulfonate (0.22 g, 0.62 mmol). The mixtures were stirred for 15 hours. Upon completion, the reaction was quenched with sat. $NaHCO_3$ (20 mL) and extracted with ethyl acetate (5×50 mL) and washed with brine. The combined organic layers were dried over anhydrous $Na_2SO_4$ and concentrated in vacuo. The residue was purified by Buchi Pureflash chromatography over silica gel cartridge (80 g) with 8:2 hexanes/ethyl acetate to give 1-(1-methyl-1H-pyrrol-2-yl)-2-phenylethan-1-one, Compound 80 (0.20 g, 17%) dried under vacuum as a reddish oil. 1H NMR (400 MHZ, $CDCl_3$): δ 7.32-7.26 (m, 4H), 7.20 (m, 1H), 7.07 (dd, 1H, J=4.0, 2.0 Hz), 6.80 (t, 1H, J=2.0 Hz), 6.13 (dd, 1H, J=4.0, 3.0 Hz), 4.05 (s, 2H), 3.90 (s, 3H). MS (ESI): Calcd. for $C_{13}H_{13}NO$: 199, found 200 $(M+H)^+$.

Example 5. Synthesis of 1-(5-(2-fluorobenzoyl)-1-methyl-1H-pyrrol-2-yl)-2-phenylethan-1-one (Compound 22)

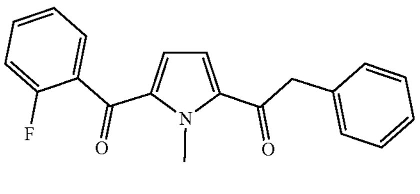 [SMILES: Cn1c(C(=O)Cc2ccccc2)ccc1C(=O)c1ccccc1F]

To a suspension of aluminum chloride (0.20 g, 1.51 mmol) in anhydrous 1,2-dichloroethane (5 mL) under argon atmosphere was added 2-fluorobenzyoyl chloride (0.19 g, 1.20 mmol) and stirred for 10 min. Then 1-(1-methyl-1H-pyrrol-2-yl)-2-phenylethan-1-one (0.20 g, 1.00 mmol) was added dropwise and the mixtures were stirred for 2 hours. Upon completion, the reaction was quenched with sat. $NaHCO_3$ (20 mL), extracted with ethyl acetate (5×50 mL) and washed with sat. $NaHCO_3$ (2×50 mL). The combined organic layers were dried over anhydrous $Na_2SO_4$, filtered, and concentrated in vacuo. The residue was purified by Buchi Pureflash chromatography over silica gel cartridge (40 g) with 8:2 hexanes/ethyl acetate to give 1-(5-(2-fluorobenzoyl)-1-methyl-1H-pyrrol-2-yl)-2-phenylethan-1-one (0.15 g, 46%) dried under vacuum as a white solid. 1H NMR (400 MHZ, DMSO-$d_6$): δ 7.71 (d, 1H, J=1.6 Hz), 7.68 (d, 1H, J=1.6 Hz), 7.62 (m, 1H), 7.55 (dt, 1H, J=7.6, 1.6 Hz), 7.36 (m, 2H), 7.34-7.26 (m, 4H), 7.22 (m, 1H), 4.18 (s, 2H), 3.86 (s, 3H). MS (ESI): Calcd. for $C_{20}H_{16}FNO_2$: 321, found 322 $(M+H)^+$ Example 6: Synthesis of 1-(5-(2-fluorobenzoyl)-1H-pyrrol-3-yl)-2-phenylethan-1-one (Compound 47)

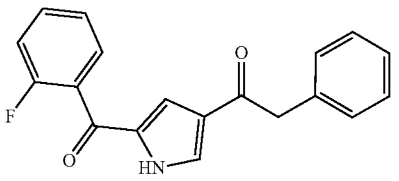 [SMILES: O=C(Cc1ccccc1)c1c[nH]c(C(=O)c2ccccc2F)c1]

To a suspension of aluminum chloride (0.22 g, 1.67 mmol) in anhydrous 1,2-dichloroethane (4 mL) under argon atmosphere was added 2-fluorobenzyoyl chloride (0.22 g, 1.40 mmol) and stirred for 10 min. Then a solution of 2-phenyl-1-(1H-pyrrol-3-yl) ethan-1-one (0.20 g, 1.00 mmol) in 1,2-dichloroethane (1 mL) was added dropwise and the mixtures were stirred for 4 hours. Upon completion, the reaction was quenched with ice and water (5 mL) and extracted with dichloromethane (4×50 mL) and washed with sat. $NaHCO_3$ (2×50 mL). The combined organic layers were dried over anhydrous $Na_2SO_4$, filtered, and concentrated in vacuo. The residue was purified by Buchi Pureflash chromatography over silica gel cartridge (40 g) with 8:2 hexanes/ethyl acetate to give 1-(5-(2-fluorobenzoyl)-1H-pyrrol-3-yl)-2-phenylethan-1-one (0.15 g, 46%) dried under vacuum as a beige solid. $^1$H NMR (400 MHZ, DMSO-$d_6$): δ 12.84 (s, 1H), 8.08 (d, 1H, J=2.0 Hz), 7.63 (m, 2H), 7.34 (m, 2H), 7.31-7.18 (m, 5H), 6.97 (s, 1H), 4.11 (s, 2H). MS (ESI): Calcd. for $C_{19}H_{14}FNO_2$: 307, found 308 $(M+H)^+$ Example 7: Synthesis of 4-(2-fluorobenzoyl)-1-methyl-1H-pyrrole-2-carboxylic acid (Compound 76)

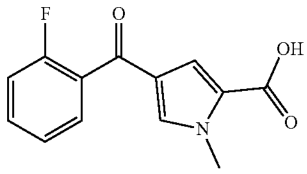 [SMILES: Cn1cc(C(=O)c2ccccc2F)cc1C(=O)O]

To a suspension of aluminum chloride (3.20 g, 40 mmol) in anhydrous chloroform (40 mL) under argon atmosphere was added 2-fluorobenzyoyl chloride (3.04 g, 19.18 mmol) and stirred for 15 min. Then a solution of 1-methylpyrrole-2-carboxylic acid (2.00 g, 15.98 mmol) in chloroform (10 mL) was added dropwise and the mixtures were heated at 50° C. for 5 hours. Upon completion, the reaction was quenched with ice and water (40 mL) and extracted with 8:2 dichloromethane/isopropanol mixtures (4×100 mL) and washed with sat. $NH_4Cl$ (2×100 mL). The combined organic layers were dried over anhydrous $Na_2SO_4$, filtered, and concentrated in vacuo. The crude residue was precipitated in methanol (60 mL) to give 4-(2-fluorobenzoyl)-1-methyl-1H-pyrrole-2-carboxylic acid (2.79 g, 71%) dried under vacuum as an off-white solid. $^1H$ NMR (400 MHZ, DMSO-$d_6$): δ 12.78 (bs, 1H), 7.67 (d, 1H, J=0.8 Hz), 7.60 (m, 1H), 7.53 (dt, 1H, J=7.2, 1.6 Hz), 7.34 (m, 2H), 7.07 (d, 1H, J=1.6 Hz), 3.89 (s, 3H). MS (ESI): Calcd. for $C_{13}H_{10}FNO_3$: 247, found 247 $(M)^+$ Example 8: Synthesis of (2-fluorophenyl) (1-methyl-1H-pyrrol-2-yl) methanone (Compound 49a)

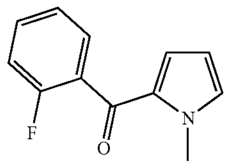

To a solution of 1-methylpyrrole (2.00 g, 24.66 mmol) in nitromethane (50 mL) under argon atmosphere was added $Zn(OTf)_2$ (1.16 g, 2.47 mmol) and followed by 2-fluorobenzoyl chloride (4.03 g, 25.40 mmol). The mixtures were stirred for 4 hours. Upon completion, the reaction was quenched with sat. $NaHCO_3$ (200 mL) and extracted with ethyl acetate (3×200 mL) and washed with brine (200 mL). The combined organic layers were dried over anhydrous $Na_2SO_4$, filtered, and concentrated in vacuo. The crude residue was purified by Buchi Pureflash chromatography over silica gel cartridge (220 g) with 100% dichloromethane to give (2-fluorophenyl) (1-methyl-1H-pyrrol-2-yl) methanone (0.27 g, 5%) dried under vacuum as a brown solid. $^1H$ NMR (400 MHZ, DMSO-$d_6$): δ 7.56 (m, 1H), 7.50 (dt, 1H, J=7.6, 1.6 Hz), 7.35-7.27 (m, 3H), 6.49 (dt, 1H, J=4.0, 1.6 Hz), 6.14 (dd, 1H, J=4.0, 2.4 Hz), 3.97 (s, 3H). MS (ESI): Calcd. for $C_{12}H_{10}FNO$: 203, found 204 $(M+1)^+$ Example 9: Synthesis of 1-(5-(2-fluorobenzoyl)-1-methyl-1H-pyrrol-3-yl)-2-phenylethan-1-one (Compound 46)

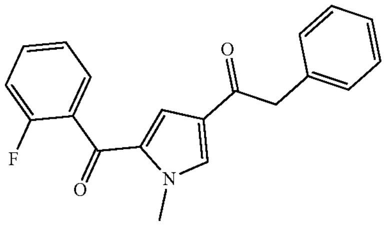 [SMILES: Cn1cc(C(=O)Cc2ccccc2)cc1C(=O)c1ccccc1F]

To a solution of (2-fluorophenyl) (1-methyl-1H-pyrrol-2-yl) methanone (0.07 g, 0.48 mmol) in nitromethane (1.5 mL) under argon atmosphere was added zinc oxide (0.01 g, 0.16 mmol) and followed by phenylacetyl chloride (0.08 g, 0.48 mmol). The mixtures were heated at 50° C. for 2 hours. The reaction was then quenched with sat. $NaHCO_3$ (20 mL) and extracted with ethyl acetate (3×25 mL) and washed with brine (20 mL). The combined organic layers were dried over anhydrous $Na_2SO_4$, filtered, and concentrated in vacuo. The crude residue was purified by Buchi Pureflash chromatography over silica gel cartridge (24 g) with 8:2 hexanes/ethyl acetate to give 1-(5-(2-fluorobenzoyl)-1-methyl-1H-pyrrol-3-yl)-2-phenylethan-1-one (0.05 g, 51%) dried under vacuum as an orange solid. $^1H$ NMR (400 MHZ, DMSO-$d_6$): δ 8.18 (s, 1H), 7.62 (m, 1H, 7.53 (m, 1H), 7.40-7.15 (m, 7H), 6.91 (s, 1H), 4.05 (s, 2H), 4.01 (s, 3H). MS (ESI): Calcd. for $C_{20}H_{16}FNO_2$: 321, found 322 $(M+1)^+$ Example 10: Synthesis of (R)-2-((tert-butyldimethylsilyl)oxy)-5-hydroxy-3,3-dimethyl-1-(1-methyl-1H-pyrrol-2-yl) pentan-1-one (Compound 86)

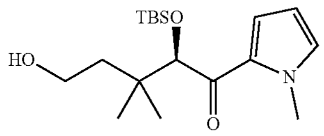 [SMILES: Cn1cccc1C(=O)[C@H](O[Si](C)(C)C(C)(C)C)C(C)(C)CCO]

To a solution of 1-methylpyrrole (0.50 g, 5.43 mmol) in anhydrous THF (5 mL) cooled with ice-bath under argon atmosphere was added 2.0M butyllithium in cyclohexane (2.85 mL, 5.70 mmol) and stirred for 30 minutes. The ice-bath was removed and equilibrate to room temperature while stirring for additional 1 hour. The mixture was then cooled again to 0° C. prior to slowly added a solution of (R)-3-((tert-butyldimethylsilyl)oxy)-4,4-dimethyldihydrofuran-2 (3H)-one (1.39 g, 5.70 mmol) in anhydrous THF (5 mL) via syringe over 5 min and stirred for 30 min at room temperature. Upon completion, the reaction was quenched with sat. $NH_4Cl$ (5 mL) and extracted with ethyl acetate (3×50 mL) and washed with sat. $NaHCO_3$ followed with brine. The combined organic layers were dried over anhydrous $Na_2SO_4$, filtered, and concentrated in vacuo. The residue was purified by Buchi Pureflash chromatography over silica gel cartridge (80 g) with 8:2 hexanes/ethyl acetate to give (R)-2-((tert-butyldimethylsilyl)oxy)-5-hydroxy-3,3-dimethyl-1-(1-methyl-1H-pyrrol-2-yl) pentan-1-one (0.73 g, 41%) dried under vacuum as a yellow oil. $^1H$ NMR (400 MHZ, DMSO-d): δ 7.13 (m, 1H), 7.08 (d, 1H, J=2.8 Hz), 6.11 (dd, 1H, J=4.0, 2.8 Hz), 4.75 (bs, 1H), 4.46 (t, 1H, J=5.2 Hz), 3.82 (s, 3H), 3.29 (dd, 1H, J=10.4, 5.6 Hz), 3.08 (dd, 1H, J=10.4, 5.2 Hz), 0.85 (s, 9H), 0.82 (s, 3H), 0.74 (s, 3H), 0.01 (s, 3H), −0.16 (s, 3H). MS (ESI): Calcd. for $C_{17}H_{31}NO_3Si$: 325, found 326 $(M+H)^+$ and 348 $(M+Na^+)$ Example 11: Synthesis of (R)-2,5-bis((tert-butyldimethylsilyl)oxy)-3,3-dimethyl-1-(1-methyl-1H-pyrrol-2-yl) pentan-1-one (Compound 83)

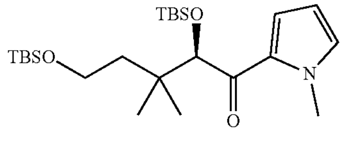 [SMILES: Cn1cccc1C(=O)[C@H](O[Si](C)(C)C(C)(C)C)C(C)(C)CCO[Si](C)(C)C(C)(C)C]

To a solution of (R)-2-((tert-butyldimethylsilyl)oxy)-5-hydroxy-3,3-dimethyl-1-(1-methyl-1H-pyrrol-2-yl) pentan-1-one (0.88 g, 2.71 mmol) and imidazole (0.46 g, 6.77 mmol) in anhydrous DMF (2 mL) cooled with ice-bath under argon atmosphere was added tert-butyldimethylsilyl chloride (0.49 g, 3.25 mmol) and stirred for 5 minutes. The ice-bath was then removed and equilibrate to room temperature while stirring for additional 24 hours. Upon completion, the reaction was quenched with sat. $NaHCO_3$ (5 mL) and extracted with dichloromethane (3×50 mL) and washed with brine (2×50 mL). The combined organic layers were dried over anhydrous $Na_2SO_4$, filtered, and concentrated in vacuo. The residue was purified by Buchi Pureflash chromatography over pre-neutrilized silica gel cartridge (40 g) with 8:2 hexanes/ethyl acetate to give (R)-2,5-bis((tert-butyldimethylsilyl) oxy)-3,3-dimethyl-1-(1-methyl-1H-pyrrol-2-yl) pentan-1-one (1.01 g, 85%) dried under vacuum as a clear oil. $^1H$ NMR (400 MHZ, DMSO-d): δ 7.148 (m, 1H), 6.98 (d, 1H, J=2.4 Hz), 6.12 (dd, 1H, J=4.0, 2.4 Hz), 4.83 (bs, 1H), 3.83 (s, 3H), 3.49 (d, 1H, J=9.6 Hz), 3.16 (d, 1H, J=9.2 Hz), 0.89 (s, 9H), 0.85 (s, 12H), 0.72 (s, 3H), 0.005 (s, 6H), −0.005 (s, 3H), −0.17 (s, 3H). MS (ESI): Calcd. for $C_{23}H_{45}NO_3Si_2$: 439, found 440 $(M+H)^+$ Example 12: Synthesis of 1-(1-methyl-5-picolinoyl-1H-pyrrol-2-yl)-2-phenylethan-1-one (Compound 25)

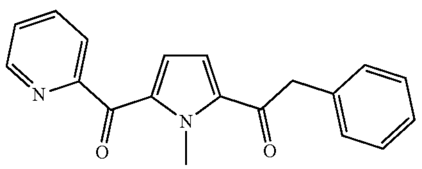 [SMILES: Cn1c(C(=O)Cc2ccccc2)ccc1C(=O)c1ccccn1]

To a suspension of aluminum chloride (0.18 g, 1.61 mmol) in anhydrous 1,2-dichloroethane (6 mL) under argon atmosphere was added pyridine-2-carbonyl chloride (0.18 g, 1.29 mmol) and stirred for 10 min. Then 1-(1-methyl-1H-pyrrol-2-yl)-2-phenylethan-1-one (0.21 g, 1.07 mmol) was added dropwise and the mixtures were heated for 3 hours. Upon completion, the reaction was quenched with ice and sat. $NaHCO_3$ (5 mL) and extracted with dichloromethane (3×50 mL) and washed with sat. $NaHCO_3$ (2×50 mL). The combined organic layers were dried over anhydrous $Na_2SO_4$, filtered, and concentrated in vacuo. The residue was purified by Buchi Pureflash chromatography over pre-neutralized silica gel cartridge (40 g) with 8:2 hexanes/ethyl acetate to give 1-(1-methyl-5-picolinoyl-1H-pyrrol-2-yl)-2-phenylethan-1-one (0.05 g, 14%) dried under vacuum as an orange solid. $^1H$ NMR (400 MHz, DMSO-$d_6$): δ 8.77 (d, 1H, J=4.8 Hz), 8.35 (d, 1H, J=1.2 Hz), 8.02 (d, 1H, J=1.2 Hz), 7.95 (d, 1H, J=1.6 Hz), 7.6 (m, 1H), 7.32-7.20 (m, 6H), 4.21 (s, 2H), 3.92 (s, 3H). MS (ESI): Calcd. for $C_{19}H_{16}N_2O_2$: 304, found 305 $(M+H)^+$ Example 13: Synthesis of (4-(2-fluorobenzoyl)-1-methyl-1H-pyrrol-2-yl) (8-oxa-2-azaspiro[4.5]decan-2-yl) methanone (Compound 77)

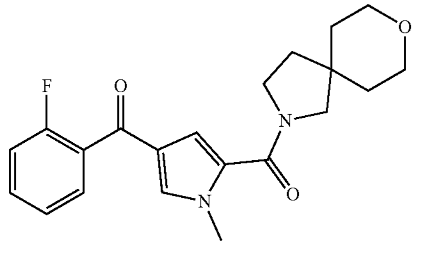 [SMILES: Cn1cc(C(=O)c2ccccc2F)cc1C(=O)N1CCC2(CCOCC2)C1]

To a solution of 4-(2-fluorobenzoyl)-1-methyl-1H-pyrrole-2-carboxylic acid (0.20 g, 0.81 mmol) in anhydrous THF (6 mL) under argon atmosphere was added thionyl chloride (0.74 mL, 10.11 mmol) and stirred for 24 hours. The solvent was then removed under vacuum to dried and a solution of 8-oxa-2-azaspiro[4.5]decane (0.15 g, 1.05 mmol) in anhydrous pyridine (4 mL) was immediately added to the crude solid under ice-bath and stirred for 10 min. The ice-bath was removed and stirred for 1 hour. Upon completion, the excess pyridine was removed under vacuum and the crude residue was extracted with ethyl acetate (4×100 mL) and washed with sat. $NaHCO_3$ (2×100 mL). The combined organic layers were dried over anhydrous $Na_2SO_4$, filtered, and concentrated in vacuo. The residue was purified by Buchi Pureflash chromatography over silica gel cartridge (40 g) with 95:5 dichloromethane/methanol to give (4-(2-fluorobenzoyl)-1-methyl-1H-pyrrol-2-yl) (8-oxa-2-azaspiro [4.5]decan-2-yl) methanone (0.17 g, 57%) dried under vacuum as a yellow solid. $^1H$ NMR (400 MHZ, DMSO-$d_6$): δ 7.62-7.52 (m, 2H), 7.48 (s, 1H), 7.33 (m, 2H), 6.92 (d, 1H, J=13.2 Hz), 3.75 (s, 3H), 3.73 (m, 1H), 3.65-3.48 (m, 6H), 3.37 (1H, partial masked under water), 1.81 (m, 2H), 1.60-1.40 (m, 4H). MS (ESI): Calcd. for $C_{21}H_{23}FN_2O_3$: 370, found 371 $(M)^+$ Example 14: Synthesis of (R)—N-(1-(4-(2-fluorobenzoyl)-1-methyl-1H-pyrrole-2-carbonyl) pyrrolidin-3-yl)-N-methylacetamide (Compound 78)

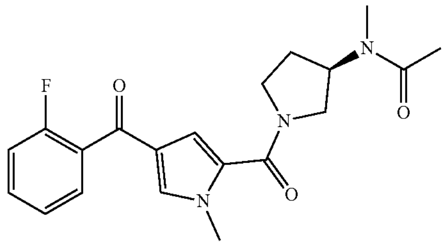 [SMILES: CC(=O)N(C)[C@@H]1CCN(C(=O)c2cc(C(=O)c3ccccc3F)cn2C)C1]

To a solution of 4-(2-fluorobenzoyl)-1-methyl-1H-pyrrole-2-carboxylic acid (0.20 g, 0.81 mmol) in anhydrous THF (6 mL) under argon atmosphere was added thionyl chloride (0.74 mL, 10.11 mmol) and stirred for 24 hours. The solvent was then removed under vacuum to dried and a solution of (R)—N-(pyrrolidine-3-yl) acetamide hydrochloride (0.19 g, 1.05 mmol) in anhydrous pyridine (4 mL) was immediately added to the crude solid under ice-bath and stirred for 10 min. The ice-bath was removed and stirred for 1 hour. Upon completion, the excess pyridine was removed under vacuum and the crude residue was extracted with ethyl acetate (4×100 mL) and washed with sat. $NaHCO_3$ (2×100 mL). The combined organic layers were dried over anhydrous $Na_2SO_4$, filtered, and concentrated in vacuo. The residue was purified by Buchi Pureflash chromatography over silica gel cartridge (40 g) with 95:5 dichloromethane/methanol to give (R)—N-(1-(4-(2-fluorobenzoyl)-1-methyl-1H-pyrrole-2-carbonyl) pyrrolidin-3-yl)-N-methylacetamide (0.15 g, 49%) dried under vacuum as a light yellow solid. $^1H$ NMR (400 MHZ, DMSO-$d_6$): δ 7.59 (m, 1H), 7.53 (dt, 1H, J=7.6, 1.6 Hz), 7.33 (m, 2H), 6.92 (d, 1H, J=1.2 Hz), 4.96 (m, 1H), 4.53 (bs, 1H), 3.76 (s, 3H), 3.68 (m, 3H), 2.89 (s, 3H), 2.08-1.90 (m, 5H). MS (ESI): Calcd. for $C_{20}H_{22}FN_3O_3$: 371, found 372 $(M)^+$ Example 15: Synthesis of (R)-2-((tert-butyldimethylsilyl)oxy)-4-((di-tert-butyl(isobutyl) silyl)oxy)-3,3-dimethyl-1-(1-methyl-1H-pyrrol-2-yl) butan-1-one (Compound 85)

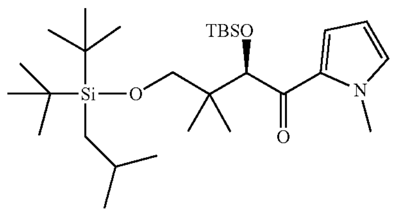 [SMILES: CC(C)C[Si](OCC(C)(C)[C@@H](O[Si](C)(C)C(C)(C)C)C(=O)c1cccn1C)(C(C)(C)C)C(C)(C)C]

To a solution of (R)-2-((tert-butyldimethylsilyl)oxy)-5-hydroxy-3,3-dimethyl-1-(1-methyl-1H-pyrrol-2-yl) pentan-1-one (0.25 g, 0.77 mmol), 4-(dimethylamino)pyridine (0.01 g, 0.08 mmol), and triethylamine (0.32 mL, 2.32 mmol) in anhydrous dioxane (4 mL) under argon atmosphere was added di-tert-butylisobutylsilyl triflate (0.46 g, 1.31 mmol) and heated to 65° C. for 3 days. Upon completion, the reaction was quenched with sat. $NaHCO_3$ (5 mL) and extracted with dichloromethane (3×50 mL) and washed with brine (2×50 mL). The combined organic layers were dried over anhydrous $Na_2SO_4$, filtered, and concentrated in vacuo. The residue was purified by Buchi Pureflash chromatography over pre-neutrilized silica gel cartridge (40 g) with 8:2 hexanes/ethyl acetate to give (R)-2-((tert-butyldimethylsilyl)oxy)-4-((di-tert-butyl(isobutyl) silyl)oxy)-3,3-dimethyl-1-(1-methyl-1H-pyrrol-2-yl) butan-1-one (0.37 g, 90%) dried under vacuum as a clear oil. $^1H$ NMR (400 MHZ, DMSO-d): δ 7.15 (d, 2H, J=3.2 Hz), 6.11 (t, 1H, J=3.2 Hz), 3.82 (s, 3H), 3.67 (dd, 2H, J=12.0, 9.2 Hz), 0.98 (s, 12H), 0.96-0.91 (m, 26H), 0.85 (s, 9H), 0.84 (s, 3H), 0.48 (d, 3H, J=6.8 Hz), −0.01 (s, 3H), −0.17 (s, 3H). MS (ESI): Calcd. for $C_{29}H_{57}NO_3Si_2$: 523, found 524 $(M+H)^+$ Example 16: Synthesis of (5-(2-fluorobenzoyl)-1-methyl-1H-pyrrol-2-yl) (8-oxa-2-azaspiro[4.5]decan-2-yl) methanone (Compound 33)

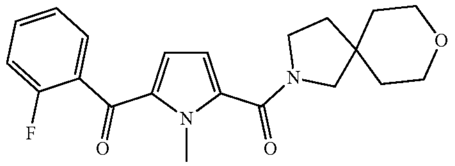 [SMILES: Cn1c(C(=O)c2ccccc2F)ccc1C(=O)N1CCC2(CCOCC2)C1]

To a solution of commercially available 5-(2-fluorobenzoyl)-1-methyl-1H-pyrrole-2-carboxylic acid (0.15 g, 0.61 mmol) in anhydrous THF (5 mL) under argon atmosphere was added thionyl chloride (0.55 mL, 7.58 mmol) and stirred for 24 hours. The solvent was then removed under vacuum to dried and a solution of 8-oxa-2-azaspiro[4.5]decane (0.11 g, 0.79 mmol) in anhydrous pyridine (3 mL) was immediately added to the crude solid under ice-bath and stirred for 10 min. The ice-bath was removed and stirred for 1 hour. Upon completion, the excess pyridine was removed under vacuum and the crude residue was extracted with 8:2 dichloromethane/isopropanol (3×50 mL) and washed with sat. $NaHCO_3$ (2×100 mL). The combined organic layers were dried over anhydrous $Na_2SO_4$, filtered, and concentrated in vacuo. The residue was purified by Buchi Pureflash chromatography over silica gel cartridge (40 g) with 8:2 hexanes/ethyl acetate to give (5-(2-fluorobenzoyl)-1-methyl-1H-pyrrol-2-yl) (8-oxa-2-azaspiro[4.5]decan-2-yl) methanone (0.16 g, 73%) dried under vacuum as a light yellow solid. $^1H$ NMR (400 MHZ, DMSO-$d_6$): δ 7.61 (m, 1H), 7.54 (m 1H), 7.33 (m, 2H), 6.53 (dd, 1H, J=9.2, 4.4 Hz), 6.47 (d, 1H, J=4.4 Hz), 4.00 (s, 3H), 3.64-3.57 (m, 6H), 3.38 (d, 2H, J=10.4 Hz), 1.84 (t, 2H, J=7.6 Hz), 1.80 (t, 2H, J=7.2 Hz), 1.55 (m, 2H), 1.46 (m, 2H). MS (ESI): Calcd. for $C_{21}H_{23}FN_2O_3$: 370, found 371 $(M)^+$ Example 17: Synthesis of N-(tert-butyl)-5-(2-fluorobenzoyl)-1-methyl-1H-pyrrole-2-carboxamide (Compound 43)

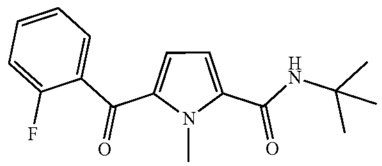 [SMILES: Cn1c(C(=O)NC(C)(C)C)ccc1C(=O)c1ccccc1F]

To a solution of commercially available 5-(2-fluorobenzoyl)-1-methyl-1H-pyrrole-2-carboxylic acid (0.15 g, 0.61 mmol) in anhydrous THF (5 mL) under argon atmosphere was added thionyl chloride (0.55 mL, 7.58 mmol) and stirred for 24 hours. The solvent was then removed under vacuum to dried and a solution of excess tert-butylamine (1.91 mL, 18.20 mmol) in anhydrous pyridine (2 mL) was immediately added to the crude solid under ice-bath and stirred for 10 min. The ice-bath was removed and stirred for 3 days. Upon completion, the excess pyridine was removed under vacuum and the crude residue was extracted with 8:2 dichloromethane/isopropanol (3×50 mL) and washed with sat. $NaHCO_3$ (2×100 mL). The combined organic layers were dried over anhydrous $Na_2SO_4$, filtered, and concentrated in vacuo. The residue was purified by Buchi Pureflash chromatography over silica gel cartridge (40 g) with 8:2 hexanes/ethyl acetate to give N-(tert-butyl)-5-(2-fluorobenzoyl)-1-methyl-1H-pyrrole-2-carboxamide (0.14 g, 74%) dried under vacuum as a yellow solid. $^1H$ NMR (400 MHZ, DMSO-$d_6$): δ 7.91 (s, 1H), 7.60 (m, 1H), 7.52 (dt, 1H, J=7.6, 2.0 Hz), 7.36-7.30 (m, 2H), 6.62 (d, 1H, J=4.4 Hz), 6.46 (dd, 1H, J=4.4, 1.2 Hz), 4.11 (s, 3H), 1.36 (s, 9H). MS (ESI): Calcd. for $C_{17}H_{19}FN_2O_3$: 302, found 303 $(M)^+$ Example 18: Synthesis of (R)-2-((tert-butyldimethylsilyl)oxy)-4-((di-tert-butyl(isobutyl) silyl)oxy)-3,3-dimethyl-1-(1-methyl-5-(2-phenylacetyl)-1H-pyrrol-2-yl) butan-1-one (Compound 87)

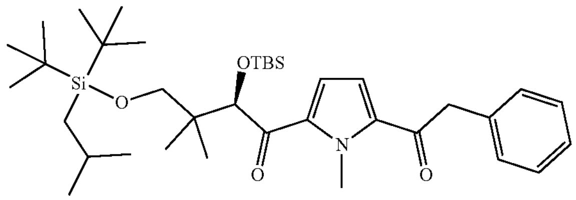 [SMILES: CC(C)C[Si](OCC(C)(C)[C@@H](O[Si](C)(C)C(C)(C)C)C(=O)c1ccc(C(=O)Cc2ccccc2)n1C)(C(C)(C)C)C(C)(C)C]

To a solution of (R)-2-((tert-butyldimethylsilyl)oxy)-4-((di-tert-butyl(isobutyl) silyl)oxy)-3,3-dimethyl-1-(1-methyl-1H-pyrrol-2-yl) butan-1-one (0.20 g, 0.38 mmol) in dichloroethane (4.0 mL) under argon atmosphere was added zinc oxide (0.02 g, 0.19 mmol) and followed by phenylacetyl chloride (0.09 g, 0.57 mmol). The mixtures were heated at 50° C. for 2 hours. The reaction was then quenched with sat. $NaHCO_3$ (20 mL) and extracted with ethyl acetate (3×25 mL) and washed with brine (20 mL). The combined organic layers were dried over anhydrous $Na_2SO_4$, filtered, and concentrated in vacuo. The crude residue was purified by Buchi Pureflash chromatography over silica gel cartridge (24 g) with 8:2 hexanes/ethyl acetate to give (R)-2-((tert-butyldimethylsilyl)oxy)-4-((di-tert-butyl(isobutyl) silyl) oxy)-3,3-dimethyl-1-(1-methyl-5-(2-phenylacetyl)-1H-pyrrol-2-yl) butan-1-one (0.05 g, 51%) dried under vacuum as an orange solid. MS (ESI): Calcd. for $C_{37}H_{63}NO_4Si_2$: 642, found 643 $(M+1)^+$

Example 19: Example of VNN1 Inhibitor Binding Assay

Test compounds were prepared as 111X stocks in 100% DMSO. $K_d$ values were determined using an 11-point 3-fold compound dilution series with three DMSO control points. All compounds for $K_d$ measurements were distributed by acoustic transfer (non-contact dispensing) in 100% DMSO. The compounds were then diluted directly into the assays such that the final concentration of DMSO was 0.9%. All reactions were performed in polypropylene 384-well plate. Each was a final volume of 0.02 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 μM non-biotinylated affinity ligand) and incubated at room temperature with shaking for 30 minutes. The kinase concentration in the eluates was measured by qPCR.

Binding constants were calculated with a standard dose-response curve using the Hill equation:

$$\text{Response} = \text{Background} + \frac{\text{Signal} - \text{Background}}{1 + \left(\frac{Kd^{Hill\,Slope}}{\text{Dose}^{Hill\,Slope}}\right)}$$

The Hill Slope was set to −1. Curves were fitted using a non-linear least square fit with the Levenberg-Marquardt algorithm. The binding data is summarized in Table 1 where A is less than 100 nM, B is 100 to 500 nM, and C is greater than 500 nM.

TABLE 1

Vanin-1 Binding constants

| Compound | Vanin Affinity (nM) |
|---|---|
| Compound 1 | B |
| Compound 2 | B |
| Compound 3 | C |
| Compound 22 | A |
| Compound 47 | C |
| Compound 76 | C |
| Compound 46 | C |
| Compound 25 | B |
| Compound 77 | A |
| Compound 78 | A |
| Compound 33 | A |
| Compound 43 | A |

Example 20: Permeability Experiments (Compound 1 & Compound 2 have High Permeability to be Used as Oral Therapeutics The permeability of compounds was evaluated with the parallel artificial membrane permeation assay (PAMPA) as an in vivo model of passive diffusion across a porous filter coated with a lipid/oil/lipid tri-layer artificial membrane. PAMPA experiments are carried out during the early drug discovery phase to screen oral absorption potential of drug compounds to eliminate poor performers and structure modification of discovery compounds to improve their in vivo diffusion characteristics. The test compounds were tested in parallel with positive controls, Diclofenac (published high permeability), Furosemide (published medium permeability), and Sulpiride (published low permeability). Donor solutions of test compound (300 μL, 20 μM in PBS/MeOH 90:10) were added to each well of the donor plate. 200 μL of PBS/MeOH 90:10 was added to each well of the acceptor plate. The acceptor plate was coupled with the donor plate and incubated for 5 hours at room temperature (RT) without agitation. In each plate, test compound was tested in triplicate. At the end of the incubation, test compound concentration in the initial donor solution, acceptor and the donor wells were determined using LC/MS/MS. Permeability of test compound was calculated based on the formula described in "Analytical Method". The PAMPA permeability classification criteria are categorized into three (3) classes with a high ($P_e \geq 1.5\times10^{-6}$ cm/s), medium ($1.5\times10^{-8} < P_e > 1.5\times10^{-6}$ cm/s), and low ($P_e < 1.5\times10^{-8}$ cm/s) permeability. Compound 1 and Compound 2 showed high permeability indicating high oral absorption potential (Table 2).

TABLE 2

PAMPA Permeability

| Compound | Permeability, $P_e$ (cm/s) | Classification |
|---|---|---|
| Compound 1 | $2.36 \times 10^{-5}$ | High |
| Compound 2 | $1.36 \times 10^{-5}$ | High |
| Diclofenac | $1.09 \times 10^{-5}$ | High |
| Furosemide | $5.86 \times 10^{-8}$ | Medium |
| Sulpiride | $3.92 \times 10^{-8}$ | Low/Medium |

Example 21: Cytochrome P450 Inhibition of VNN1 Inhibitors (VNN1 Inhibitors do not have an Effect on Drug-Drug Interactions, Evaluated by CYP-Direct Inhibition Assays)

Cytochrome P450 inhibition of a drug is a key factor in determining pharmacokinetic drug-drug interactions. The objective of this study is to evaluate the inhibition potential of VNN1 inhibitors on six (6) major human cytochrome P450 enzymes, including CYP1A2, CYP2C8, CYP2C9, CYP2C19, CYP2D6, and CYP3A4. Inhibition was determined by using a substrate cocktail and analyzing the rate of specific metabolites formation. The cytochrome P450 inhibition assay was developed using a cocktail consisting of six (6) probe substrates ethoxy-resorufin (CYP1A2), rosiglitazone (CYP2C8), diclofenac (CYP2C9), S-mephenytoin (CYP2C19), dextromethorphan (CYP2D6), and midazolam (CYP3A4). The cocktail was incubated in human liver microsome with NADPH regenerating system (NRS) in a shaking bath at 37±2° C. The formation of specific metabolites was monitored by LC/MS/MS. Test compound was added to the cocktail-liver microsome mixture at varying concentrations and its effect on cytochrome P450 activity was determined by analyzing the rate of specific metabolite formation. The percent inhibition was calculated and plotted with reference to the concentration, and the $IC_{50}$ value for inhibition was derived by fitting the data with a standard sigmoidal dose-response equation via MLA "Quest Graph™ ED50 Calculator." AAT Bioquest, Inc, 17 Sep. 2020, aatbio.com/tools/ed50-calculator. IC50 values were obtained only when the data fit in the curve, and if the % inhibition was less than 50% at 100 μM, then $IC_{50}$ will be >100 μM. The reliability of the inhibition assay was established by confirming the inhibition of known inhibitors on different P450 enzymes. The $IC_{50}$ is categorized into three classes with a high ($IC_{50}$<1 μM), medium (1<$IC_{50}$>10 μM), and low/no ($IC_{50}$>10 μM) risk potential. The $IC_{50}$ values of VNN1 inhibitors in all six CYP450 isozymes, 1A2, 2C8, 2C9, 2C19, 2D6, and 3A4 were summarized in Table 3. VNN1 inhibitors showed little or no inhibition on all six CYP450 isozymes with an $IC_{50}$ of more than 10 μM. Compound 1 and Compound 2 VNN1 inhibitors are unlikely to cause clinically important pharmacokinetic interactions with drugs metabolized by cytochrome P450 enzymes.

TABLE 3

In-Vitro $IC_{50}$ calculations of VNN1 Inhibitors

| Compound | CYP isozyme | $IC_{50}$ (μM) | Risk Classification |
|---|---|---|---|
| Compound 1 | 1A2 | >100 | Low/No |
| | 2C8 | >100 | Low/No |
| | 2C9 | >100 | Low/No |
| | 2C19 | 50.6 | Low/No |
| | 2D6 | >100 | Low/No |
| | 3A4 | >100 | Low/No |
| Compound 2 | 1A2 | >100 | Low/No |
| | 2C8 | 65.5 | Low/No |
| | 2C9 | 63.4 | Low/No |
| | 2C19 | 15.3 | Low/No |
| | 2D6 | 27.0 | Low/No |
| | 3A4 | 73.7 | Low/No |

Example 22: Cellular Assay for Anti-Inflammatory Properties of VNN1 Inhibitors; VNN1 Inhibitors have Potent Anti-Inflammatory Properties, Suppressing Key Pro-Inflammatory Cytokines Involved in the Pathogenesis of Multiple Autoimmune Diseases The anti-inflammatory properties of the four VNN1 inhibitors (Compound 1, Compound 2, Compound 3, and Compound 80) were evaluated in an immune cellular assay targeting key pro-inflammatory cytokines involved in the pathogenesis of multiple autoimmune disease.

Specifically, THP-1 human monocytes were grown in 6-well plates (RPMI 1640+10% FBS+1% P/S). After washing with PBS the THP-1 cells were differentiated into macrophages using 20 nM of phorbol 12-myristate 13-acetate (PMA) for 24 hrs. Compound 1, Compound 2, Compound 3, and Compound 80 (1 μM) were added into the macrophages, which are incubated for 4 hours before the addition of 100 ng/mL lipopolysaccharide (LPS) for either 4 or 24 hours. Next, the macrophages are collected via centrifugation at 1.2K rpm for 5 min and use their media to evaluate cytokine protein levels by using the Bio-rad Cytokine ELISA multiplex assay (cat. No M5000031YV). The supernatants from macrophages treated only with only LPS+PMA are collected and use as negative controls. All VNN1 inhibitors (Compound 1, Compound 2, Compound 3, and Compound 80) showed suppression of TNF-alpha (TNFA), interleukin 6 (IL6), interleukin 1beta (IL1B), MCP1 and interleukin 8 (IL8). Importantly, the VNN1 inhibitors Compound 1, Compound 2, Compound 3, and Compound 80 showed highly potent activity against IL6, TNFA and MCP1.

There are several therapeutics in the market or in development against the pro-inflammatory cytokines IL6, TNFA and MCP1 for use in Ulcerative Colitis, Crohn's Disease, Atopic Dermatitis, Psoriasis, Systemic Erythematosus Lupus, Atherosclerosis and Type 1 Diabetes, thus Compound 1, Compound 2, Compound 3, and Compound 80 have use as therapeutic for these diseases, since they inhibit simultaneously multiple pro-inflammatory signals.

Example 23: Example of Cellular Assay for Anti-Inflammatory Properties of VNN1 Inhibitors THP-1 cells were grown to confluence and plated in 6-well plates. PMA (25 nM) was added to the medium and replaced with non-PMA containing medium 24 hrs later. ATH compounds (1 μM) or vehicle (0.1% DMSO) were added and allowed to incubate. After 4 hrs LPS (50 ng/ml) was added without replacement of the medium and supernatants were collected after 4 and 24 hrs. Media were placed on ice for cytokine detection using ELISA (Quantikine, R&D Systems).

Figure 3:
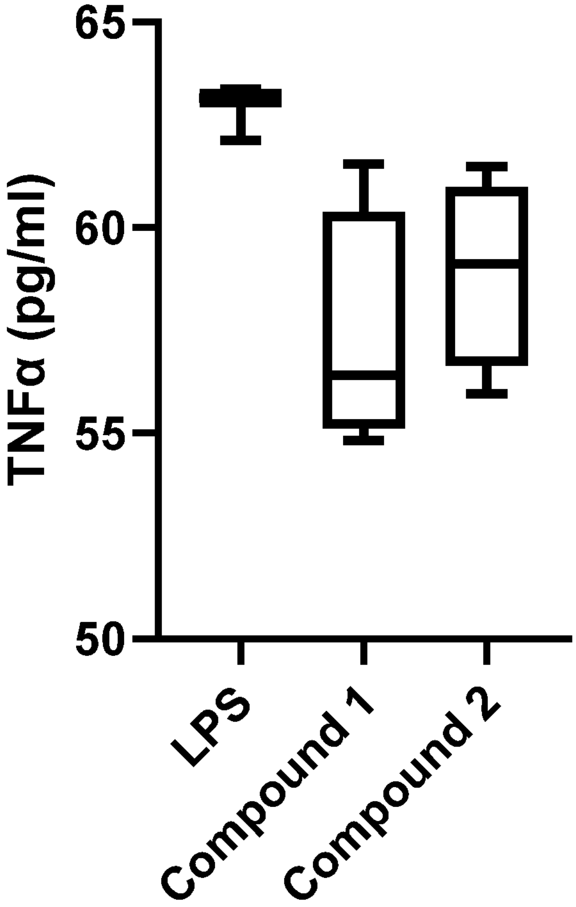
FIG. 3 data regarding vanin 1 (VNN1) inhibitors. The disclosed compounds show suppression of TNF-alpha (TNFA) expression after LPS (lipopolysaccharide) treatment, in THP-1 human monocytes ($p<0.05$).

VNN1 inhibitors Compound 1 and Compound 2 show suppression of TNF-alpha (TNFA) expression after LPS (lipopolysaccharide) treatment, in THP-1 human monocytes (FIG. 3, $p<0.05$ for both).

Example 24: Prophetic Example of Cytochrome P450 Inhibition of VNN1 Inhibitors Inhibition by Cytochrome P450 is determined using a substrate cocktail and analyzing the rate of specific metabolites formation outlined in Example 21. The following structures were tested: Compound 5, Compound 9, Compound 10, Compound 13, Compound 14, Compound 16, Compound 20, Compound 21, Compound 23, Compound 24, and Compound 25.

The $IC_{50}$ values of VNN1 Compound 5, Compound 9, Compound 10, Compound 13, Compound 14, Compound 16, Compound 20, Compound 21, Compound 23, Compound 24, and Compound 25 in all six CYP450 isozymes, 1A2, 2C8, 2C9, 2C19, 2D6, and 3A4 are summarized in Table 2. VNN1 inhibitors Compound 5, Compound 9, Compound 10, Compound 13, Compound 14, Compound 16, Compound 20, Compound 21, Compound 23, Compound 24, and Compound 25 show little or no inhibition on all six CYP450 isozymes with an $IC_{50}$ of more than 10 uM. VNN1 inhibitors Compound 5, Compound 9, Compound 10, Compound 13, Compound 14, Compound 16, Compound 20, Compound 21, Compound 23, Compound 24, and Compound 26 are unlikely to cause clinically important pharmacokinetic interactions with drugs metabolized by cytochrome P450 enzymes.

TABLE 4

| In-Vitro $IC_{50}$ calculations of VNN1 Inhibitors | | | |
|---|---|---|---|
| Compound | CYP isozyme | $IC_{50}$ (μM) | Risk Classification |
| Compound 5 | 1A2 | >100 | Low/No |
| | 2C8 | >100 | Low/No |
| | 2C9 | >100 | Low/No |
| | 2C19 | 60.3 | Low/No |
| | 2D6 | >100 | Low/No |
| | 3A4 | >100 | Low/No |
| Compound 9 | 1A2 | >100 | Low/No |
| | 2C8 | >100 | Low/No |
| | 2C9 | >100 | Low/No |
| | 2C19 | 67.2 | Low/No |
| | 2D6 | >100 | Low/No |
| | 3A4 | >100 | Low/No |
| Compound 10 | 1A2 | >100 | Low/No |
| | 2C8 | >100 | Low/No |
| | 2C9 | >100 | Low/No |
| | 2C19 | 62.6 | Low/No |
| | 2D6 | >100 | Low/No |
| | 3A4 | >100 | Low/No |
| Compound 13 | 1A2 | >100 | Low/No |
| | 2C8 | >100 | Low/No |
| | 2C9 | 71.9 | Low/No |
| | 2C19 | >100 | Low/No |
| | 2D6 | >100 | Low/No |
| | 3A4 | >100 | Low/No |
| Compound 14 | 1A2 | >100 | Low/No |
| | 2C8 | >100 | Low/No |
| | 2C9 | >100 | Low/No |
| | 2C19 | 58.3 | Low/No |
| | 2D6 | >100 | Low/No |
| | 3A4 | >100 | Low/No |
| Compound 16 | 1A2 | >100 | Low/No |
| | 2C8 | >100 | Low/No |
| | 2C9 | >100 | Low/No |
| | 2C19 | 55.2 | Low/No |
| | 2D6 | >100 | Low/No |
| | 3A4 | >100 | Low/No |
| Compound 20 | 1A2 | >100 | Low/No |
| | 2C8 | >100 | Low/No |
| | 2C9 | >100 | Low/No |
| | 2C19 | 71.3 | Low/No |
| | 2D6 | >100 | Low/No |
| | 3A4 | >100 | Low/No |
| Compound 21 | 1A2 | >100 | Low/No |
| | 2C8 | >100 | Low/No |
| | 2C9 | 61.0 | Low/No |
| | 2C19 | >100 | Low/No |
| | 2D6 | >100 | Low/No |
| | 3A4 | >100 | Low/No |
| Compound 26 | 1A2 | >100 | Low/No |
| | 2C8 | >100 | Low/No |
| | 2C9 | >100 | Low/No |
| | 2C19 | 59.2 | Low/No |
| | 2D6 | >100 | Low/No |
| | 3A4 | >100 | Low/No |
| Compound 23 | 1A2 | >100 | Low/No |
| | 2C8 | >100 | Low/No |
| | 2C9 | >100 | Low/No |
| | 2C19 | 80.9 | Low/No |
| | 2D6 | >100 | Low/No |
| | 3A4 | >100 | Low/No |
| Compound 24 | 1A2 | >100 | Low/No |
| | 2C8 | >100 | Low/No |
| | 2C9 | >100 | Low/No |
| | 2C19 | 75.3 | Low/No |
| | 2D6 | >100 | Low/No |
| | 3A4 | >100 | Low/No |

Example 25: Prophetic Example of Cellular Assay for Anti-Inflammatory Properties of VNN1 Inhibitors The anti-inflammatory properties of the VNN1 inhibitors Compound 5, Compound 9, Compound 10, Compound 13, Compound 14, Compound 16, Compound 20, Compound 21, Compound 26, Compound 23, and Compound 24 are evaluated using the immune cellular assay outlined in Example 6. Suppression of TNF-alpha (TNFA), interleukin 6 (IL6), interleukin 1beta (IL1B), MCP1 and interleukin 8 (IL8) is determined.

All VNN1 inhibitors (Compound 5, Compound 9, Compound 10, Compound 13, Compound 14, Compound 16, Compound 20, Compound 21, Compound 26, Compound 23, and Compound 24) show suppression of TNF-alpha (TNFA), interleukin 6 (IL6), interleukin 1beta (IL1B), MCP1 and interleukin 8 (IL8). Importantly, the VNN1 inhibitors show highly potent activity against IL6, TNFA and MCP1.

Example 26: Prophetic Example of VNN1 Inhibitor Binding Assay

Test compounds are prepared as 111X stocks in 100% DMSO. $K_d$ values are determined using an 11-point 3-fold compound dilution series with three DMSO control points. All compounds for $K_d$ measurements are distributed by acoustic transfer (non-contact dispensing) in 100% DMSO. The compounds are then diluted directly into the assays such that the final concentration of DMSO is 0.9%. All reactions performed in polypropylene 384-well plate. Each is a final volume of 0.02 ml. The assay plates are incubated at room temperature with shaking for 1 hour and the affinity beads are washed with wash buffer (1×PBS, 0.05% Tween 20). The beads are then re-suspended in elution buffer (1×PBS, 0.05% Tween 20, 0.5 μM non-biotinylated affinity ligand) and incubated at room temperature with shaking for 30 minutes. The kinase concentration in the eluates is measured by qPCR.

Binding constants are calculated with a standard dose-response curve using the Hill equation:

$$\text{Response} = \text{Background} + \frac{\text{Signal} - \text{Background}}{1 + \left(\frac{Kd^{\text{Hill Slope}}}{\text{Dose}^{\text{Hill Slope}}}\right)}$$

The Hill Slope was set to −1. Curves were fitted using a non-linear least square fit with the Levenberg-Marquardt algorithm. The binding data is summarized in Table 4 where A is less than 100 nM, B is 100 to 500 nM, and C is greater than 500 nM.

TABLE 5

| VNN1 Binding constants | |
|---|---|
| ID | $K_d$ (nM) |
| Compound 5 | A |
| Compound 9 | A |
| Compound 10 | A |
| Compound 13 | A |
| Compound 14 | A |
| Compound 16 | A |
| Compound 20 | A |
| Compound 21 | A |
| Compound 26 | A |
| Compound 23 | A |
| Compound 24 | A |
| Compound 27 | A |

Example 27: Prophetic Example of In Vivo Anti-Inflammatory Efficacy of VNN1 Inhibitors Vanin-1 gene expression was upregulated in biopsies of patients with inflammatory bowel disease (IBD), especially those with ulcerative colitis (UC). In the 2,4,6-trinitrobenzene sulfonic acid (TNBS)-induced colitis mouse model Vanin-1 deficiency protects these animals from the development of colitis. Our data presented herein demonstrate that addition of Vanin-1 inhibitors Compound 1 and Compound 2 to THP-1 human monocytes significantly inhibits TNFα release in response to the potent inflammatory inducer LPS.

C57BL/6 mice (20-22 grams) are fed ad lib and assigned to 4 different groups (n=8/group). After a 72 hr acclimation period the test group groups receive 25 mg/kg of test compound PO (gavage) in vehicle daily. A control group receives vehicle alone. After 24 hrs, mice are weighed and TNBS is injected intra-colonicaly using 5 cm of polyethylene (¼ inch) tubing. Mice are then treated with the test compounds and weighed daily for 4 days. Mice are sacrificed on day 4 and clinical score is assessed. Intestinal tissue for and blood are also collected. Tissues are either flash frozen and kept in −80° C. for RNA and protein isolation or placed in 10% formalin solution for future histological analysis. Blood is spun at 5K rpm for 5 min and serum is collected and kept at −20° C. for multiplex cytokine analysis.

Combined with the central role of TNFα in Vanin-1 pathophysiology, the data above are strongly predictive of a beneficial effect of the Vanin-1 inhibitors disclosed herein in animal models of colitis and subsequently in the amelioration of inflammatory responses in IBD patients. The efficacy data is summarized in Table 6 below where A is strong inhibition, B is moderate inhibition and C is no inhibition.

TABLE 6

| Compound | Vannin-1 Affinity (nM) |
|---|---|
| Compound 1 | A |
| Compound 2 | B |
| Compound 6 | A |
| Compound 80 | B |
| Compound 8 | B |
| Compound 60 | A |
| Compound 34 | A |
| Compound 45 | A |
| Compound 52 | B |
| Compound 53 | A |
| Compound 59 | A |
| Compound 68 | A |
| Compound 72 | A |
| Compound 11 | B |

Example 28: Prophetic Example of Treating IBD Patients

This is a prophetic example. A VNN1 inhibitor as disclosed in any of Examples 19 to 27 is used to treat patients with Ulcerative Colitis and Crohn's Disease patients with active disease, who were sensitive or refractory to previous anti-TNFA treatments. The inhibitor is administered orally as a capsule at a dose of 50-200 mg daily for twelve weeks. After the completion of the treatment, the patients have both clinical and histological improvement, assessed by Mayo or CDAI clinical score, endoscopic appearance, and histological evaluation.

Example 29: Prophetic Example of Treating Cancer Patients

This is a prophetic example. A VNN1 inhibitor as disclosed in any of Examples 19 to 27 is used to treat patients with colon cancer, liver cancer, pancreatic cancer, gastric cancer, esophageal cancer, prostate cancer, breast cancer, cholangiocarcinomas, sarcomas, or acute myeloid leukemia. The inhibitor is administered orally as a capsule at a dose of 50-200 mg daily in patients with or without chemotherapy. After the completion of the treatment, the patients have clinical improvement, characterized by increased survival after prognosis.

What is claimed is:

1. A compound, or a pharmaceutically acceptable salt thereof, having a structure represented by Formula I:

(I)

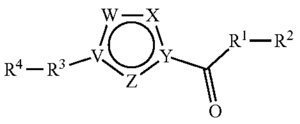

wherein:

V, W, X, Y, and Z are each independently selected from the group consisting of C, C($R^5$), N, and $NR^6$ and at least one instance of V, W, X, Y, and Zis N or $NR^6$ with the remaining variables being C or C($R^5$);

$R^1$ is selected from the group consisting of optionally substituted $C_{1-3}$ alkylene, optionally substituted 3-12 membered heterocyclyl, —$NR^7$—, or $R^1$ is not present;

$R^2$ is selected from the group consisting of —H, alkyl,

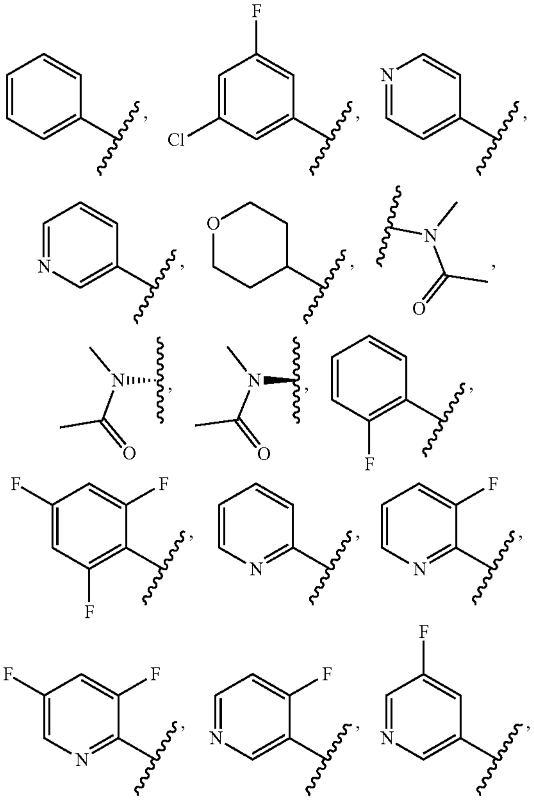

-continued

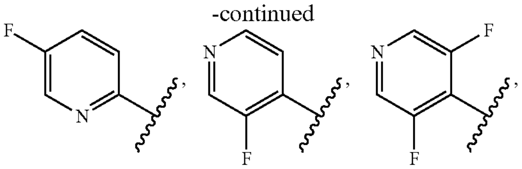

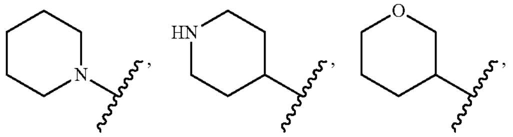

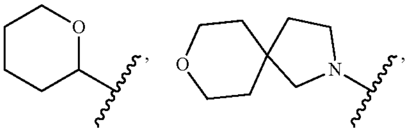

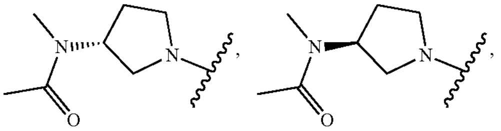

and

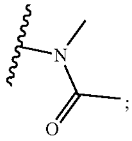

;

and $R^3$ is selected from the group consisting of optionally substituted $C_{1-3}$ alkylene, —$NR^7$—, —C(═O)—, —C(═O)NH—, and —C(═O)$NR^7$—, or $R^3$ is not present;

$R^4$ is selected from the group consisting of

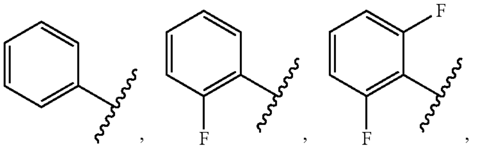

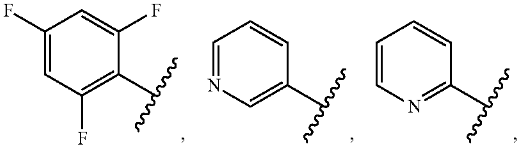

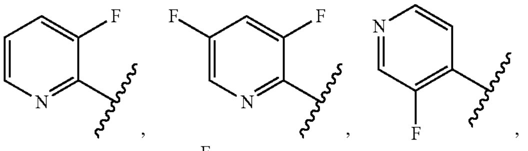

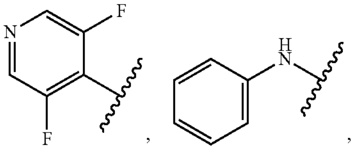

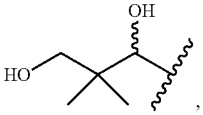

, and

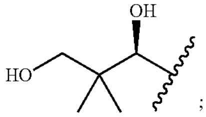

;

and each instance of $R^5$, $R^6$ and $R^7$, where present, is independently selected from the group consisting of —H, halogen, hydroxy, $C_{1-6}$ alkyl, $C_1$-$C_6$ alkoxy, $C_{1-6}$ haloalkyl, optionally substituted $C_{6-10}$ aryl, optionally substituted $C_{6-10}$ benzyl, and optionally substituted $C_{3-7}$ carbocyclyl;

wherein when W is $NR^6$, $R^4$ is selected from the group consisting of

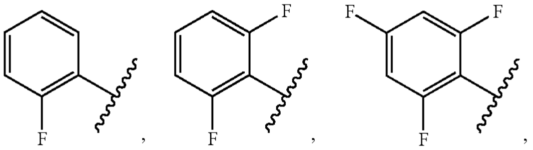

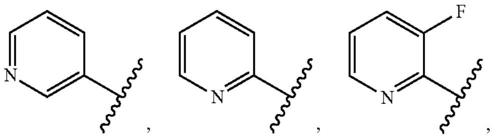

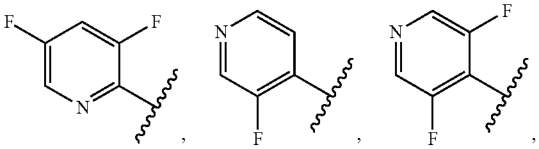

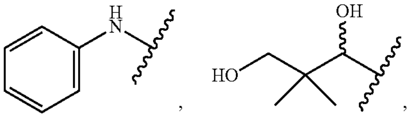

, and

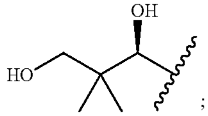

;

and wherein when X is $NR^6$, $R^2$ is selected from the group consisting of —H, alkyl,

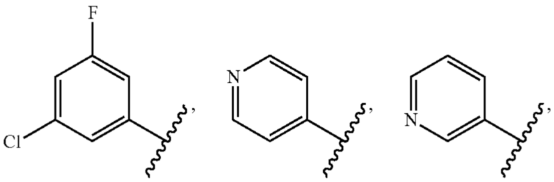

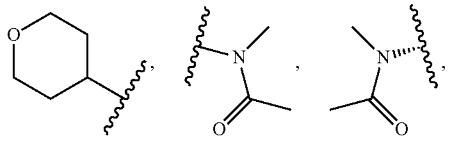

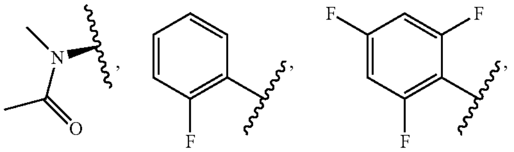

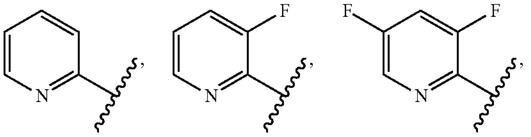

-continued

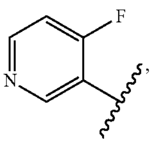,
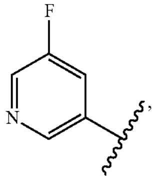,
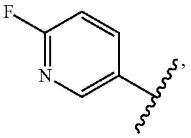,
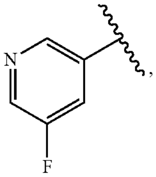,
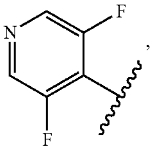,
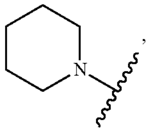,
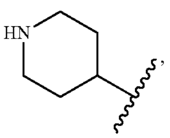,
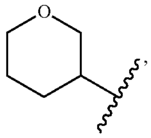,
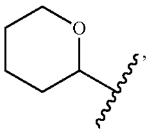,
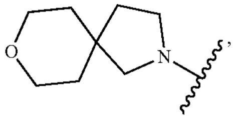,
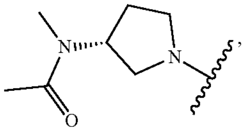,
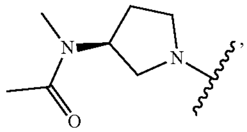, and
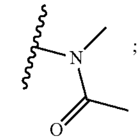;

and $R^4$ is selected from the group consisting of

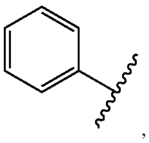,
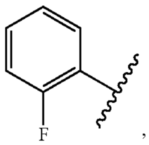,
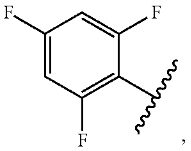,
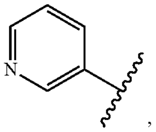,
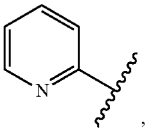,
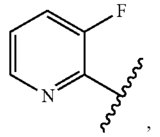,
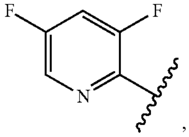,
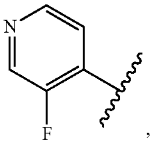,
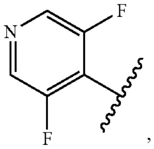,
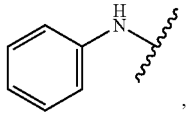,
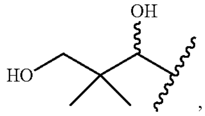, and
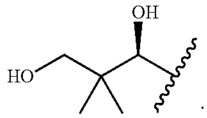.

2. The compound of claim 1, wherein the structure of Formula (I) is further represented by a formula selected from any one of Formulae (Ia), (Ib), (Ic), (Id), or (Ie):

(Ia)

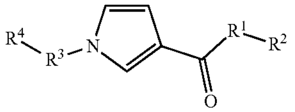

(Ib)

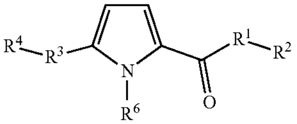

(Ic)

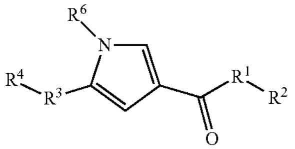

(Id)

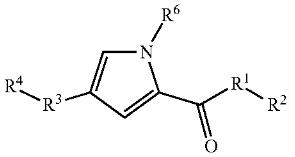

(Ie)

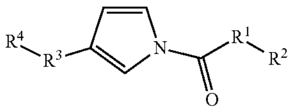

3. The compound of claim 1, wherein $R^1$ is selected from the group consisting of —NH—, —$CH_2$—, —C(H)$R^8$, —$CH_2C(H)R^8$—, —$C(R^8)_2$, or $R^1$ is not present, wherein each instance of $R^8$, where present, is independently selected from the group consisting of halogen, hydroxy, optionally substituted $C_{1-6}$ alkyl, optionally substituted $C_1$-$C_6$ alkoxy, optionally substituted $C_{1-6}$ haloalkyl, optionally substituted $C_{6-10}$ aryl, optionally substituted $C_{6-10}$ aralkyl, optionally substituted $C_{6-10}$ haloaralkyl, and optionally substituted $C_{3-7}$ carbocyclyl.

4. The compound of claim 1, wherein $R^2$ is selected from the group consisting of:

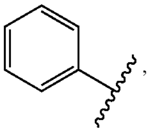,
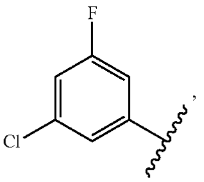,
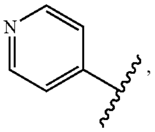,
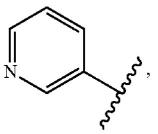,
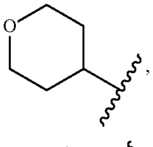,
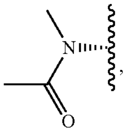, and
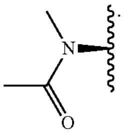.

5. The compound of claim 1, wherein $R^3$ is —$C(R^6)_2$—, —C(=O)—, or —C(O)$NR^6$—, wherein each instance of $R^6$, where present, is independently selected from the group consisting of —H, halogen, hydroxy, $C_{1-6}$ alkyl, $C_1$-$C_6$ alkoxy, $C_{1-6}$ haloalkyl, and $C_{6-10}$ aryl.

6. The compound of claim 1, wherein $R^3$ is selected from the group consisting of —$CH_2$— and —C(=O)—.

7. The compound of claim 1, wherein $R^3$ is selected from the group consisting of —$CH_2$—, —C(=O)—, and —C(=O)NH—.

8. The compound of claim 1, wherein $R^4$ is selected from the group consisting of:

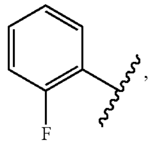, 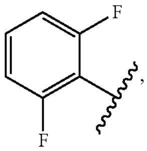, 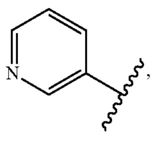,

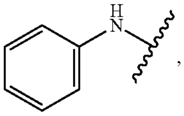, and 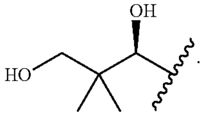.

9. The compound of claim 1, wherein, when any one or more of $R^1$ or $R^3$ is optionally substituted, one or more optional substitutions of $R^1$ or $R^3$ are independently selected from the group consisting of halogen, hydroxy, $C_{1-6}$ alkyl, $C_{1-6}$ alkoxy, aryl, and heteroaryl.

10. The compound of claim 1, wherein the structure of Formula I is further represented by a formula selected from any one of Formulae Ia2 or Ib2

(Ia2)

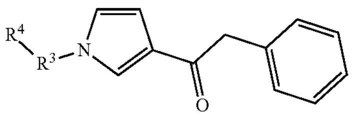

(Ib2)

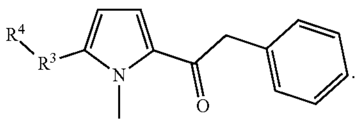

11. The compound of claim 1, wherein $R^4$ is selected from the group consisting of:

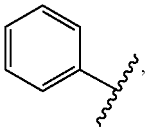, 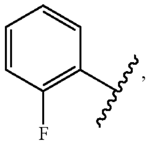, 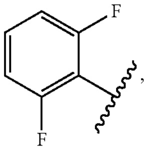,

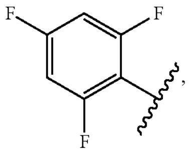, 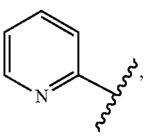, 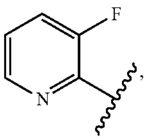,

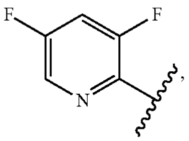, 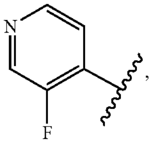, and 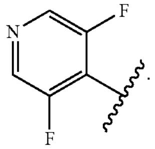.

12. The compound of claim 1, wherein the structure of Formula I is further represented by a formula selected from any one of Formulae Ia5 or Ib5:

Ia5

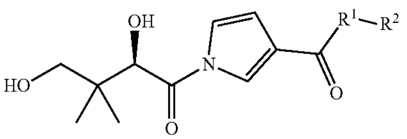

Ib5

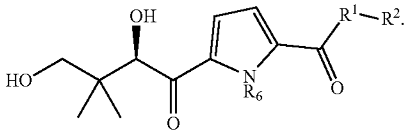

wherein:

$R^1$ is —$CH_2$— or a single bond; and $R^2$ is selected from the group consisting of optionally substituted $C_{6-10}$ aryl, optionally substituted 6 membered heteroaryl, and optionally substituted 6-10 membered heterocyclyl; and $R^6$ is selected from the group consisting of —H, $C_{1-6}$ alkyl, $C_{1-6}$ haloalkyl, and $C_{6-10}$ aryl.

13. The compound of claim 12, wherein $R^2$ is selected from the group consisting of:

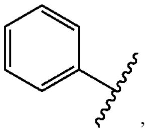, 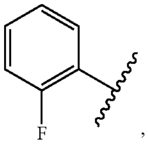, 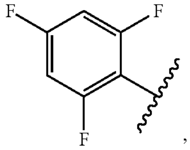,

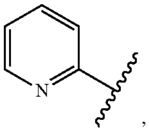, 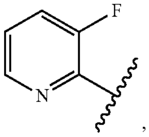, 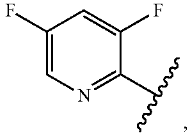,

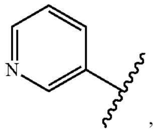, 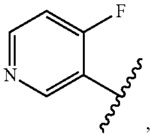, 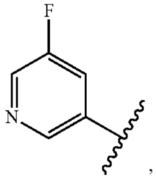,

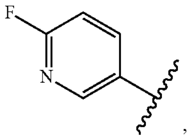, 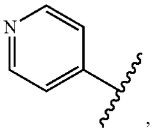, 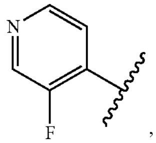,

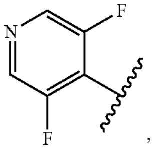, 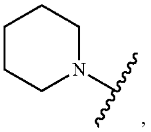, 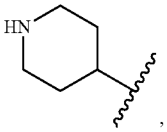,

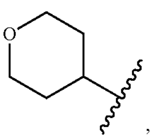, 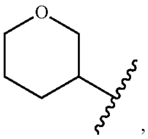, 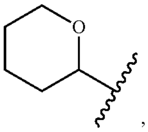, and

-continued
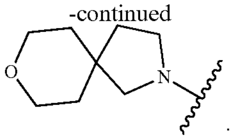
.
14. The compound of claim 1, wherein the structure of Formula I is further represented by a formula selected from any one of the following compounds:
Compound 1
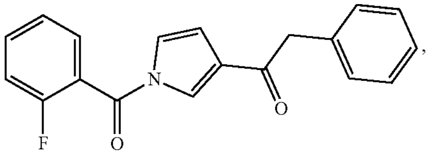
Compound 2
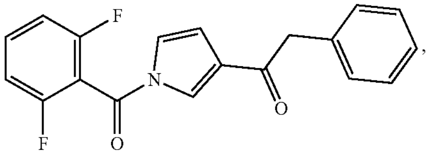
Compound 3
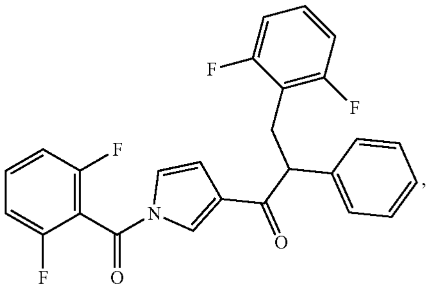
Compound 4
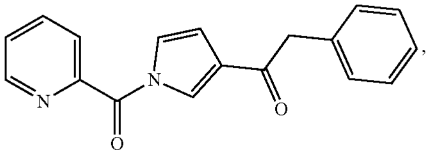
Compound 5
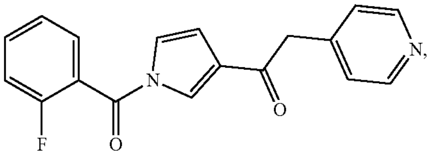
Compound 6
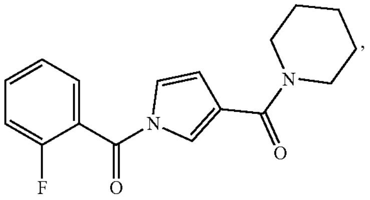
Compound 7
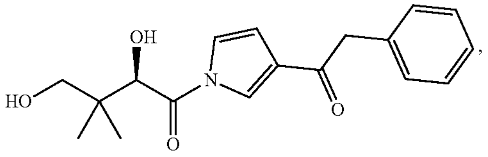
-continued
Compound 8
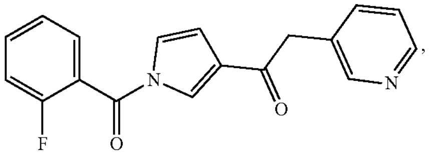
Compound 9
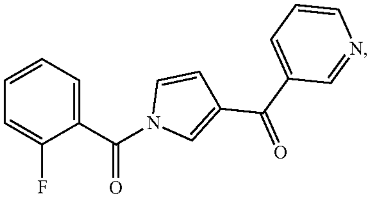
Compound 10
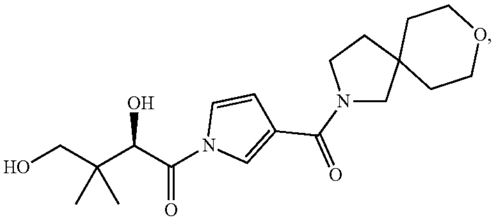
Compound 11
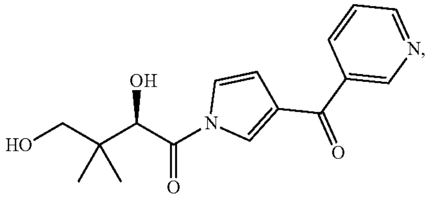
Compound 12
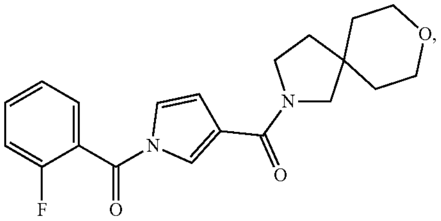
Compound 13
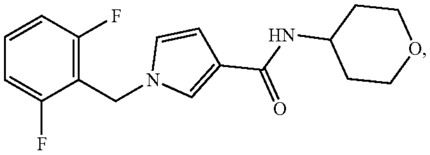
Compound 14
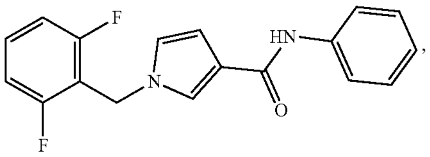
Compound 15
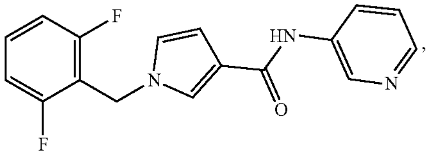

-continued
Compound 16
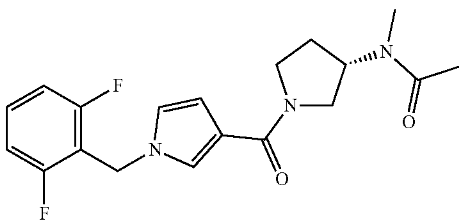,
Compound 17
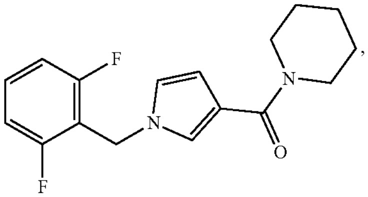,
Compound 18
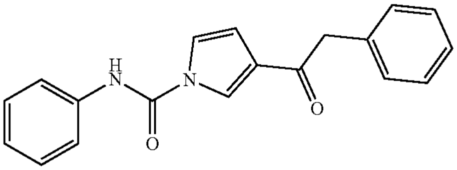,
Compound 19
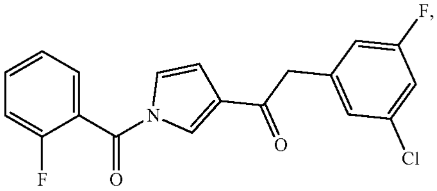,
Compound 20
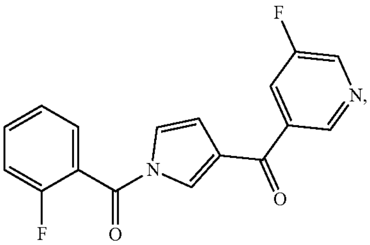,
Compound 21
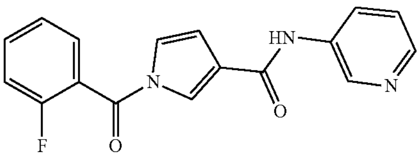,
Compound 22
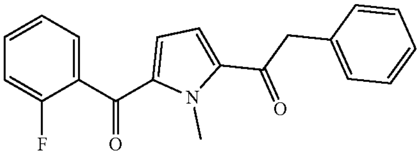,
Compound 23
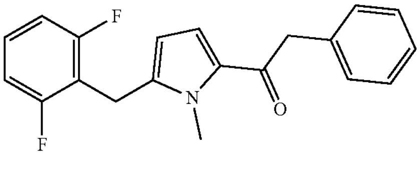,
-continued
Compound 24
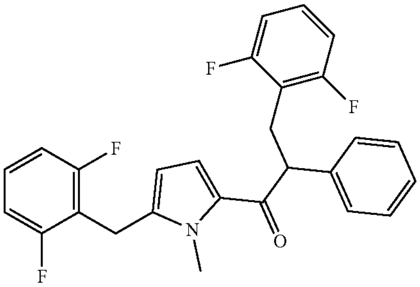,
Compound 25
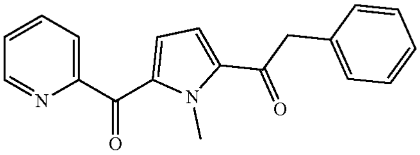,
Compound 26
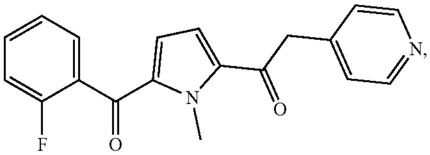,
Compound 27
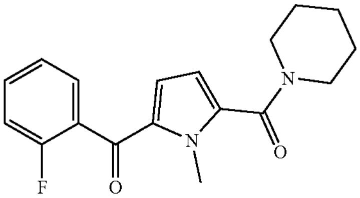,
Compound 28
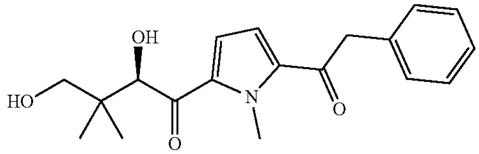,
Compound 29
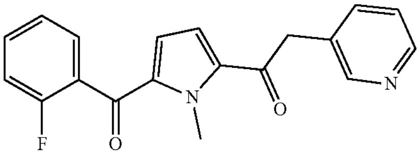,
Compound 30
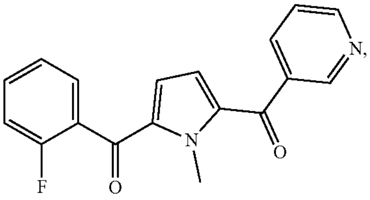,
Compound 31
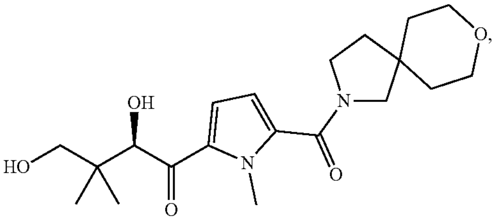, -continued
Compound 32
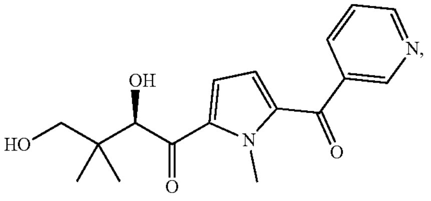
Compound 33
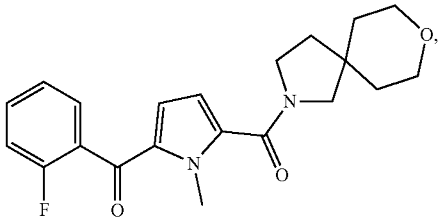
Compound 34
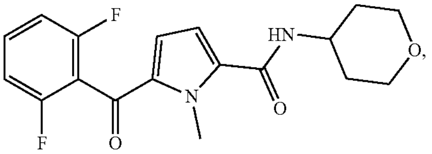
Compound 35
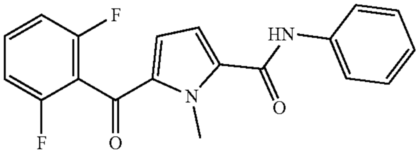
Compound 36
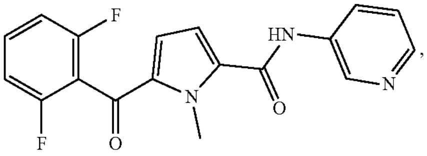
Compound 37
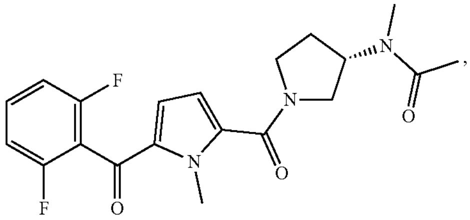
Compound 38
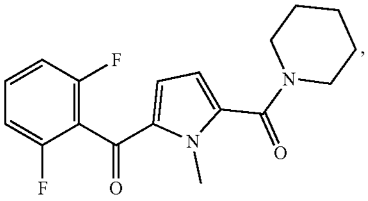
Compound 39
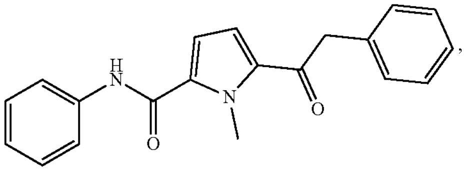
-continued
Compound 40
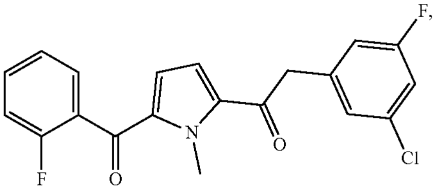
Compound 41
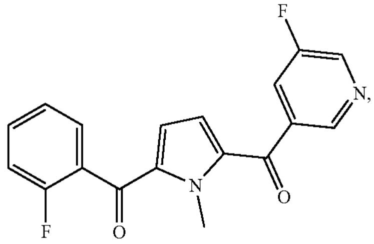
Compound 42
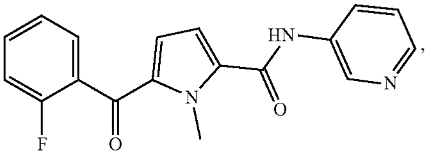
Compound 43
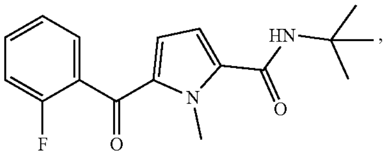
Compound 44
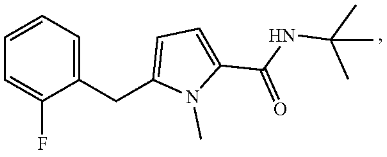
Compound 45
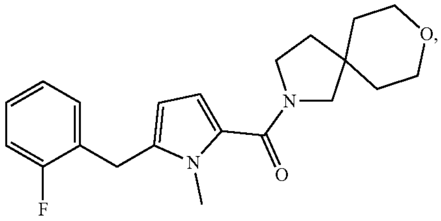
Compound 46
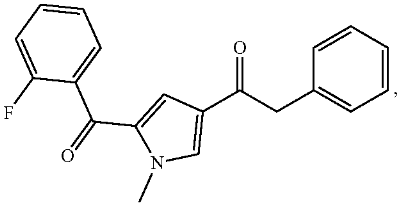
Compound 47
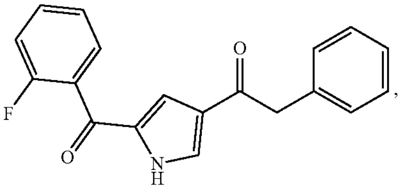

-continued
Compound 48
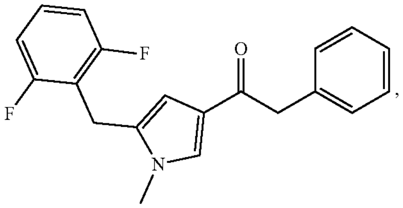
Compound 49
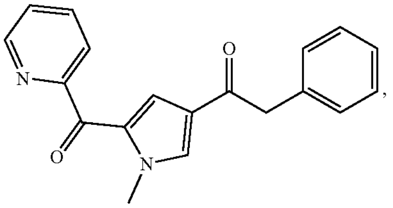
Compound 50
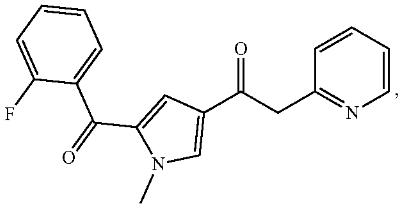
Compound 51
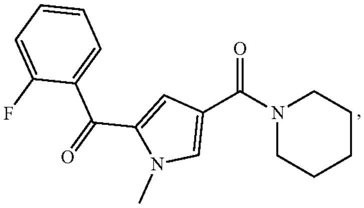
Compound 52
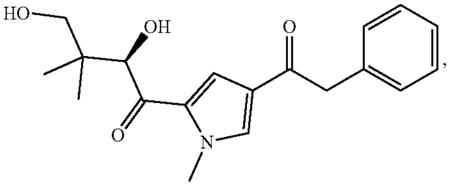
Compound 53
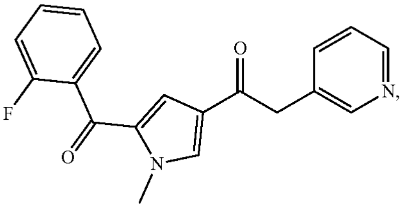
Compound 54
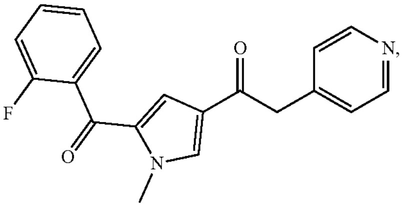
-continued
Compound 55
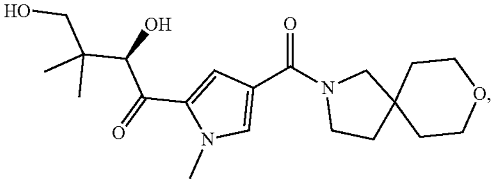
Compound 56
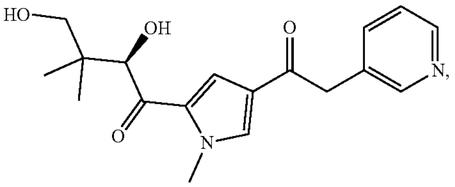
Compound 57
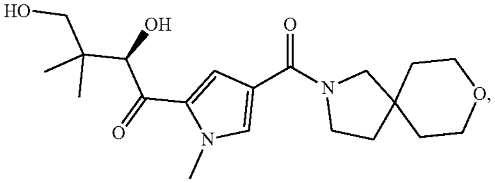
Compound 58
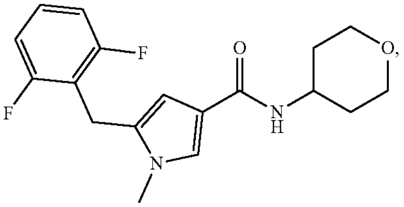
Compound 59
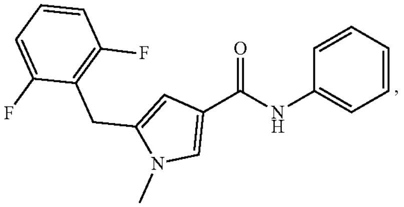
Compound 60
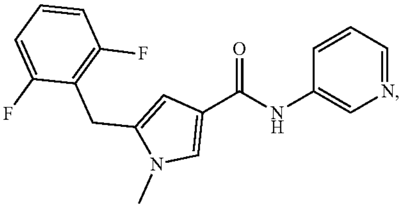
Compound 61
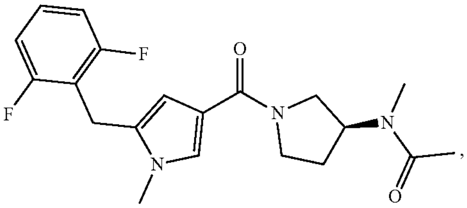

-continued
Compound 62
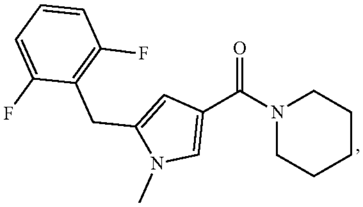
Compound 64
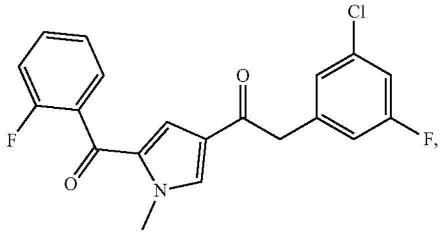
Compound 65
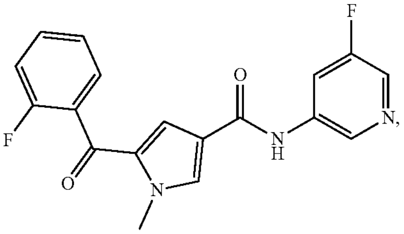
Compound 66
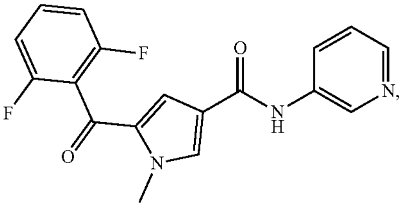
Compound 67
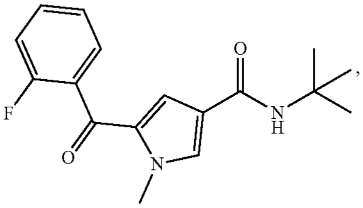
Compound 68
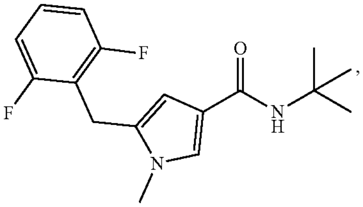
Compound 69
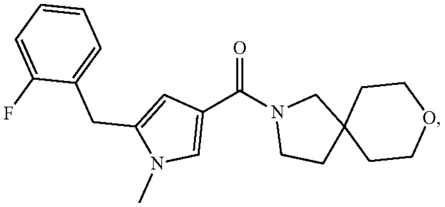
-continued
Compound 70
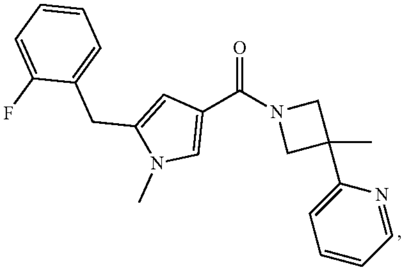
Compound 71
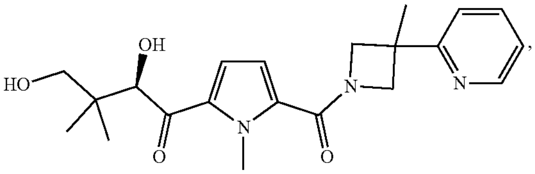
Compound 72
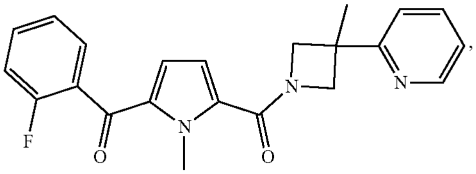
Compound 73
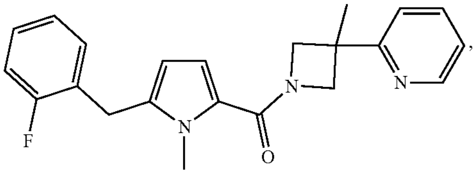
Compound 74
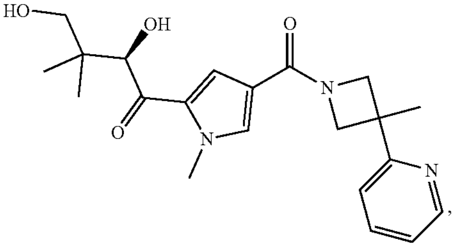
Compound 75
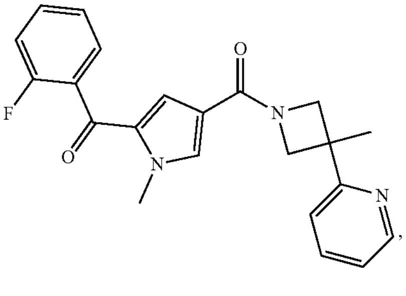

-continued
Compound 77
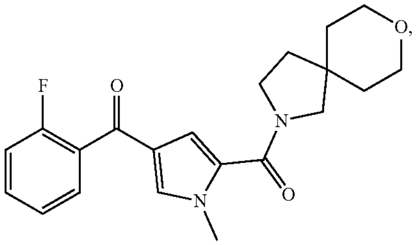
Compound 78
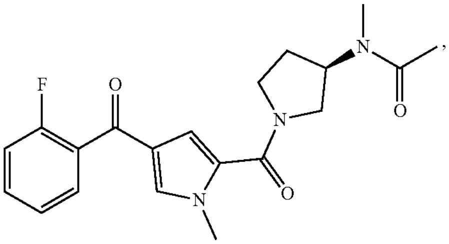
Compound 79
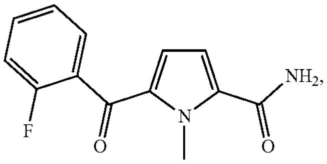
and
Compound 81
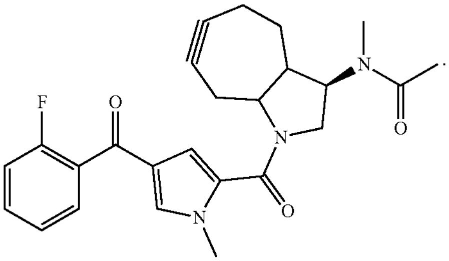
15. The compound of claim 1, or a pharmaceutically acceptable salt thereof, wherein the structure of Formula I is further represented by a structure selected from:
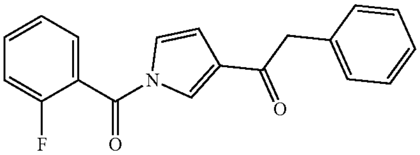
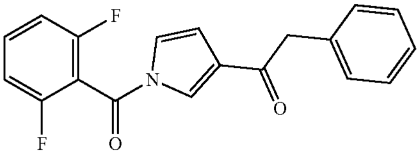
-continued
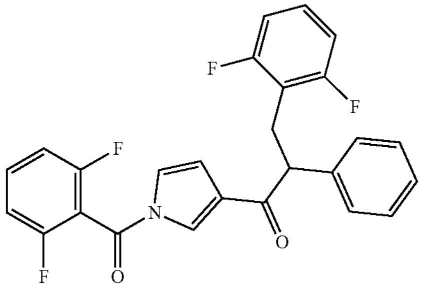
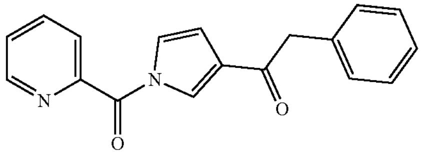
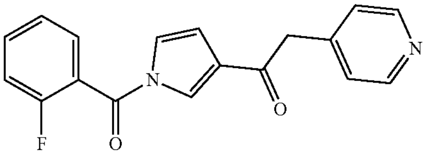
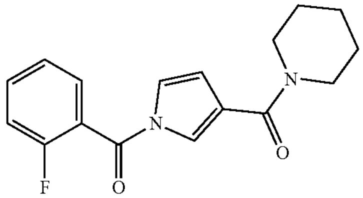
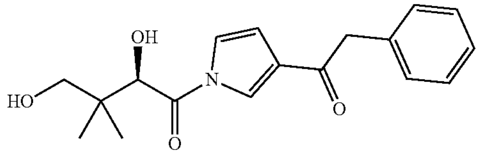
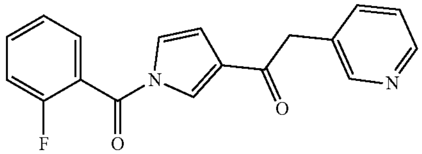
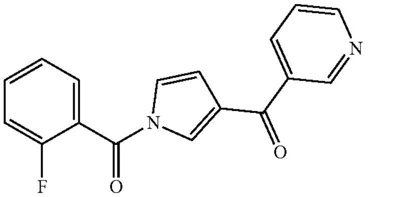
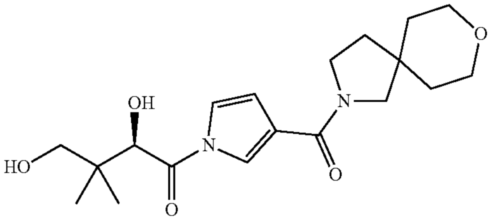
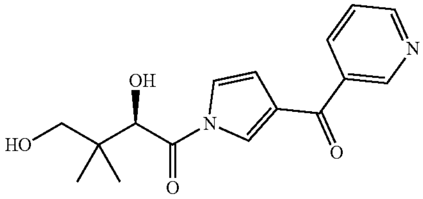

-continued
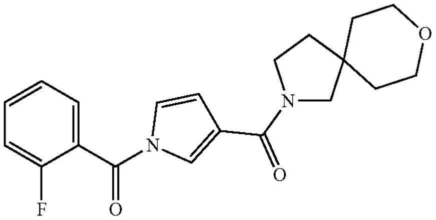
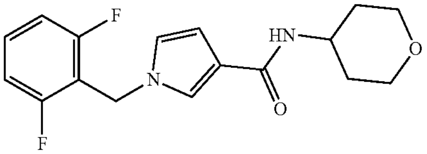
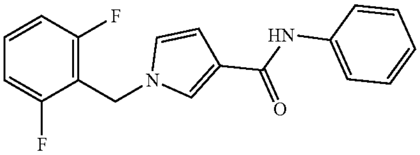
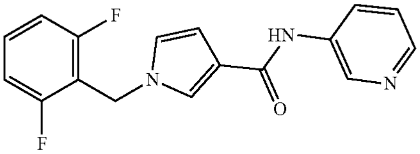
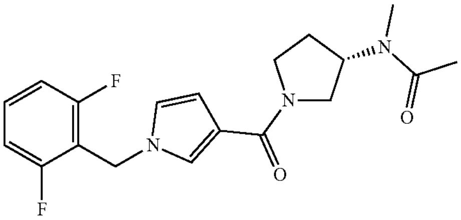
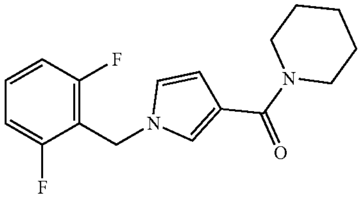
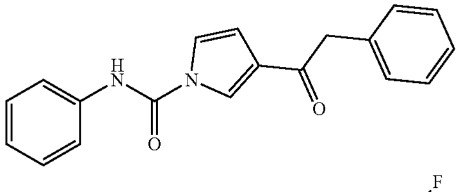
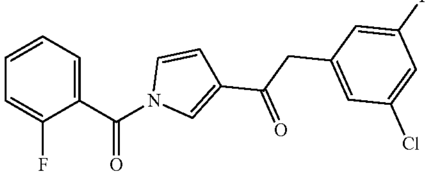
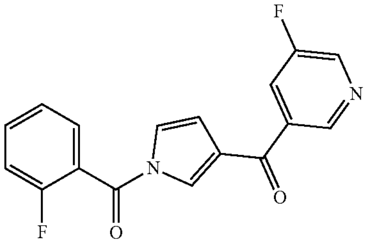
-continued
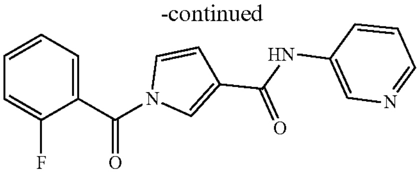
16. The compound of claim 1, or a pharmaceutically acceptable salt thereof, wherein the structure of Formula I is further represented by a structure selected from:
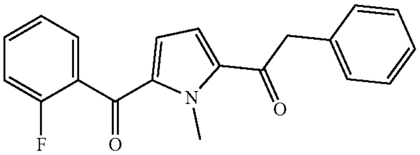
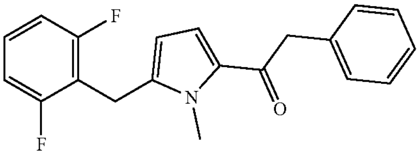
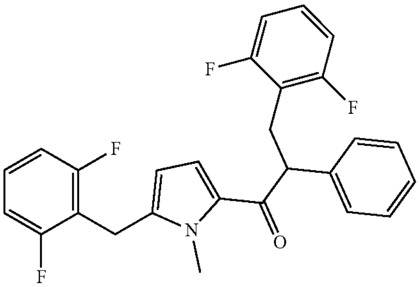
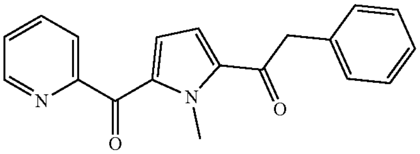
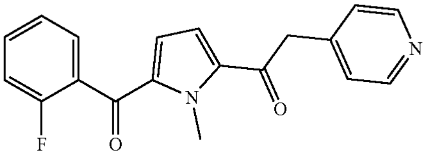
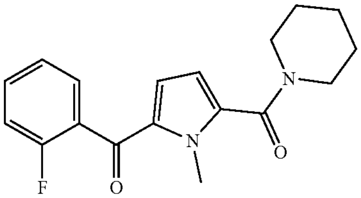
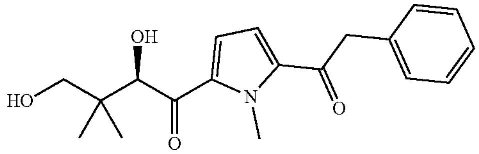
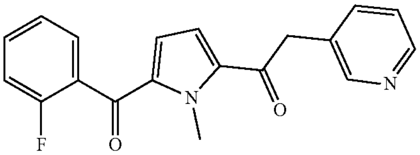

-continued

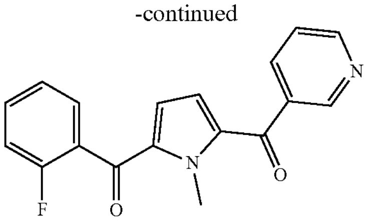

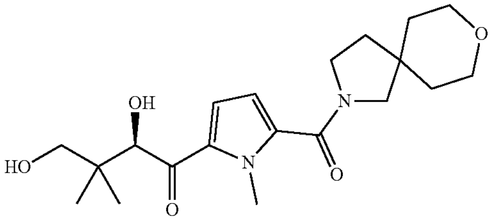

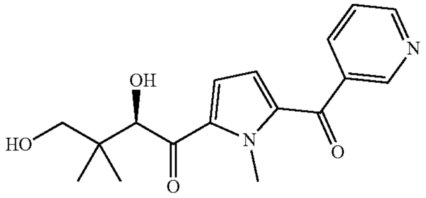

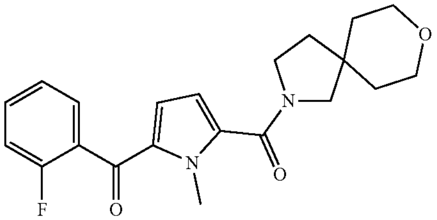

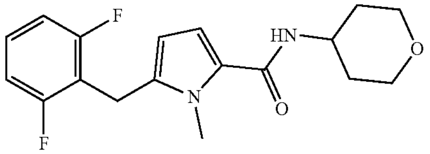

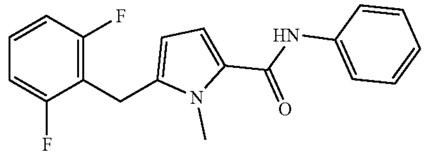

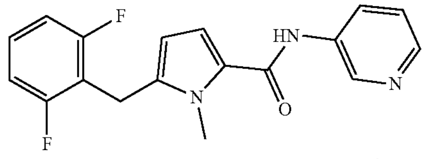

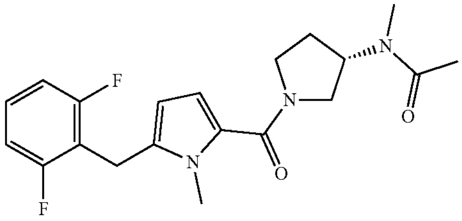

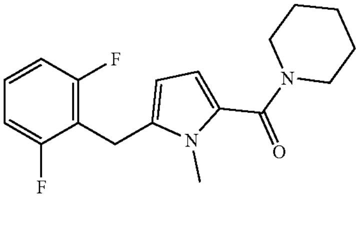

-continued

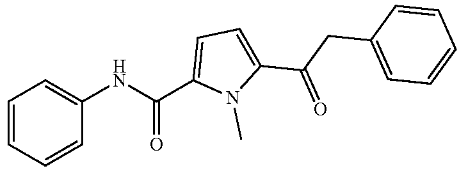

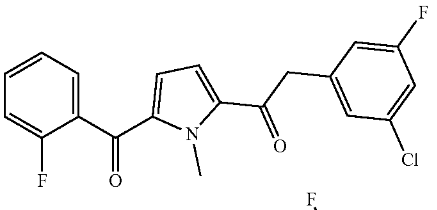

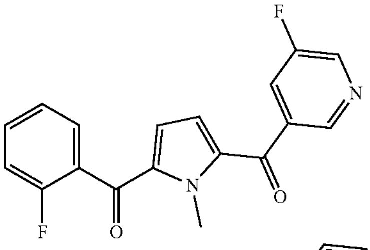

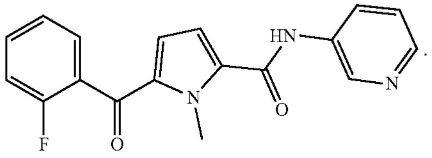

17. A method of treating a VNN1 mediated condition comprising administering to a subject requiring treatment a compound of claim 1.

18. A method of manufacturing a compound as disclosed in claim 1, the method comprising functionalizing a pyrrole starting material with one or more substituents.

19. A compound, or a pharmaceutically acceptable salt thereof, having a structure represented by Formula I:

(I)

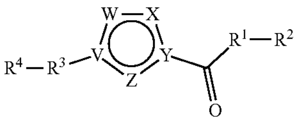

wherein:

V, W, X, Y, and Z are each independently selected from the group consisting of C, C($R^5$), N, and $NR^6$ and at least one instance of V, W, X, Y, and Zis N or $NR^6$ with the remaining variables being C or C($R^5$);

$R^1$ is selected from the group consisting of:

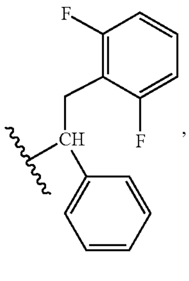 , 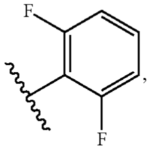 , 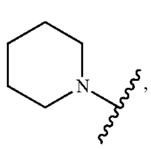 ,

-continued

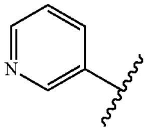,
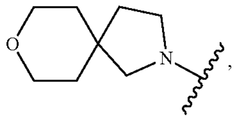,
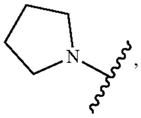, and 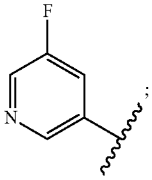;

$R^2$ is either not present or is selected from the group consisting of-H, —OH, optionally substituted alkyl, optionally substituted N-amido, optionally substituted $C_{6-10}$ aryl, 5-10 optionally substituted heteroaryl, optionally substituted $C_{6-10}$ aryl, optionally substituted 5-10 membered heteroaryl, optionally substituted 3-10 membered carbocyclyl, and optionally substituted 3-12 membered heterocyclyl, or $R^2$ is not present; $R^3$ is selected from the group consisting of optionally substituted $C_{1-3}$ alkylene, —$NR^7$, —C(—O)—, —C(═O)NH—, and —C(═O) $NR^7$—, or $R^3$ is not present;

$R^4$ is selected from the group consisting of optionally substituted $C_{6-10}$ aryl, optionally substituted 5-10 membered heteroaryl, optionally substituted 3-10 membered heterocyclyl, and optionally substituted $C_{1-6}$ alkyl, or $R^4$ is not present; and each instance of $R^5$, $R^6$ and $R^7$, where present, is independently selected from the group consisting of —H, halogen, hydroxy, $C_{1-6}$ alkyl, $C_1$-$C_6$ alkoxy, $C_{1-6}$ haloalkyl, optionally substituted $C_{6-10}$ aryl, optionally substituted $C_{6-10}$ benzyl, and optionally substituted $C_{3-7}$ carbocyclyl.

20. A compound, or a pharmaceutically acceptable salt thereof, having a structure represented by Formula I:

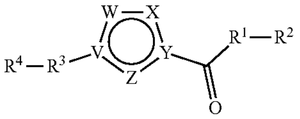

(I)

wherein:

V, W, X, Y, and Z are each independently selected from the group consisting of C, C($R^5$), N, and $NR^6$ and at least one instance of V, W, X, Y, and Z is N or $NR^6$ with the remaining variables being C or C($R^5$);

$R^1$ is selected from the group consisting of optionally substituted $C_{1-3}$ alkylene, optionally substituted 3-12 membered heterocyclyl, —$NR^7$—, or $R^1$ is not present;

$R^2$ is an optionally substituted N-amido represented by:

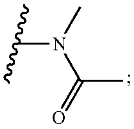 [SMILES: *N(C)C(C)=O];

$R^3$ is selected from the group consisting of optionally substituted $C_{1-3}$ alkylene, —$NR^7$—, —C(═O)—, —C(═O)NH—, and —C(═O) $NR^7$—, or $R^3$ is not present;

$R^4$ is selected from the group consisting of optionally substituted $C_{6-10}$ aryl, optionally substituted 5-10 membered heteroaryl, optionally substituted 3-10 membered heterocyclyl, and optionally substituted $C_{1-6}$ alkyl, or $R^4$ is not present; and each instance of $R^5$, $R^6$ and $R^7$, where present, is independently selected from the group consisting of —H, halogen, hydroxy, $C_{1-6}$ alkyl, $C_1$-$C_6$ alkoxy, $C_{1-6}$ haloalkyl, optionally substituted $C_{6-10}$ aryl, optionally substituted $C_{6-10}$ benzyl, and optionally substituted $C_{3-7}$ carbocyclyl.

* * * * *